US007737134B2

(12) United States Patent
Romo et al.

(10) Patent No.: US 7,737,134 B2
(45) Date of Patent: Jun. 15, 2010

(54) ANTICANCER AGENTS AND USE

(75) Inventors: Daniel Romo, College Station, TX (US); Jun Liu, Clarksville, MD (US); Nam Song Choi, Chenonam (KR); Zonggao Shi, Columbia, MO (US); Woon-Kai Low, Baltimore, MD (US); Yongjun Dang, Baltimore, MD (US); Tilman Schneider-Poetsch, Erfstadt (DE)

(73) Assignees: The Texas A & M University System, College Station, TX (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/544,474

(22) Filed: Oct. 6, 2006

(65) Prior Publication Data

US 2007/0149581 A1      Jun. 28, 2007

Related U.S. Application Data

(63) Continuation-in-part of application No. 10/388,257, filed on Mar. 13, 2003, now Pat. No. 7,230,021.

(60) Provisional application No. 60/724,200, filed on Oct. 6, 2005, provisional application No. 60/364,347, filed on Mar. 13, 2002.

(51) Int. Cl.
   *A01N 43/00*    (2006.01)
   *A61K 31/33*    (2006.01)
   *C07D 513/00*   (2006.01)
(52) U.S. Cl. ...................................... 514/183; 540/455
(58) Field of Classification Search ................... None
   See application file for complete search history.

(56) References Cited

U.S. PATENT DOCUMENTS

| 4,548,481 A | 10/1985 | Yamada |
| 4,729,996 A | 3/1988 | Wright et al. |
| 4,737,510 A | 4/1988 | Rinehart, Jr. |
| 4,808,590 A | 2/1989 | Higa et al. |
| 6,057,333 A | 5/2000 | Gunaskera et al. |
| 7,230,021 B2 * | 6/2007 | Romo et al. ............... 514/368 |

FOREIGN PATENT DOCUMENTS

| EP | 0 647 645 A1 | 4/1995 |
| JP | 6321955 A | 11/1994 |
| WO | WO 03/077862 | * 9/2003 |

OTHER PUBLICATIONS

Giuseppe et al. Expert Opinion on Therapeutic Patents, 1997, 7(4), 307-323.*
Northcote et al. Tetrahedron Letters, 1991, 32(44), 6411-14.*
"Lung diseases, fungal", http://www.nlm.nih.gov/cgi/mesh/2008/MB_cgi?mode=&index=7836&field=all&HM=&ll=&PA=&form=&input=, accessed Jun. 19, 2008.*
Dermatomycoses, http://www.nlm.nih.gov/cgi/mesh/2008/MB_cgi?mode=&index=3723&field=all&HM=&ll=&PA=&form=&input=, accessed Jun. 19, 2008.*
Pattenden, G., et al., The Intramolecular Stille Reaction in Some Target Natural Product Syntheses, Journal of Organometallic Chemistry 653, (2002) 261-268, Nottingham, UK.
Hehre W., et al., Self-Consistent Molecular Orbital Methods. XII. Further Extensions of Gaussian-Type Basis Sets for Use in Molecular Orbital Studies of Organic Molecules, J. Chem. Phys., 56:2257-2261 (1972).
Inanaga J., et al., A. Rapid Esterification by Means of Mixed Anhydride and Its Application to Large-ring Lactonization, Chem. Soc. Japan, 52:1989-1993 (1979).
Franci M., et al., Self-Consistent Molecular Orbital Methods. XIII. A Polarization-Type Basis Set for Second-Row Elements, J. Chem. Phys 77:3654-3665 (1982).
Northcote P., et al., Pateamine: A Potent Cytotoxin From the New Zealand Marine Sponge, *Mycale* Sp., Tetrahedron Letters, vol. 32, No. 44, pp. 6411-6414 (1991).
Farina V., et al., Large Rate Accelerations in the Stile Reaction with Tri-2-furylphosphine and Triphenylarsine as Palladium Ligands: Mechanistic and Synthetic Implications, J. Am. Chem. Soc. 1991, 113, 9585-9595.
Becke, A., A New Mixing of Hartree-Fock and Local Density-Functional Theories, J. Chem. Phys. 98:1372-1377 (1993).
Becke, A., Density-Functional Thermochemistry. III. The Role of Exact Exchange, J. Chem. Phys. 98:5648-5652 (1993).
Aguilar, E., et al., Reinvestigation of a Modified Hantzch Thiazole Synthesis, Tetrahedron Letters, vol. 35, No. 16, pp. 2473-2476 (1994).
Su., B., et al. JNK Is Involved in Signal Integration During Costimulation of T Lymphocytes, Cell, vol. 77, 727-736 (1994).
Dong, Q., et al., Reductive Cleavage of TROC Groups Under Neutral Conditions with Cadmium-Lead Couple, Tetrahedron Letters, vol. 36, No. 32, pp. 5681-5682 (1995).
Hung, D., et al., Synthesis of Discodermolides Useful for Investigating Microtubule Binding and Stabilization, J. Am. Chem. Soc. 1996, 118, 11054-11080.

(Continued)

*Primary Examiner*—James O Wilson
*Assistant Examiner*—Noble Jarrell
(74) *Attorney, Agent, or Firm*—Christensen O'Connor Johnson Kindness PLLC

(57) ABSTRACT

Provided herein are compositions, all related stereoisomers as well as pharmaceutically acceptable salts provided as simplified analogs of pateamine A, in which the analogs generally are devoid of the C3-amino and C5-methyl groups, also referred to as desmethyl, desamino-pateamine A. Suitable analogs provide anticancer and antiproliferative effects in vivo and in vitro by a novel drug mechanism of action described herein for pateamine A, including inhibition of eIF4A-dependent translation initiation. As with pateamine A, as described herein, suitable analogs cause cell cycle arrest or induce apoptosis in transformed cells. However, toxicity of such compounds to slow growing normal cells is low. In addition, such analogs, like pateamine A, target translation initiation factors and are useful as anticancer and antiproliferative agents in subjects in need thereof. Moreover, the analogs, like pateamine A, are valuable molecular probes for evaluation of eukaryotic translation initiation and as lead compounds for development of improved anticancer agents.

27 Claims, 17 Drawing Sheets

OTHER PUBLICATIONS

Hung, D., et al., Understanding and Controlling the Cell Cycle With Natural Products, Chemistry & Biology, Aug. 1996, 3:623-639.

Rzasa, R., et al., Total Synthesis of the Novel, Immunosuppressive Agent (−)-Pateamine A from *Mycale* sp. Employing a B-Lactam-Based Macrocyclization, J. Am. Chem. Soc. 1998, 120, 591-592.

Remuinan, M., et al., Total Synthesis of (−)-Pateamine, a Novel Polyene Bis-Macrolide with Immunosuppressive Activity From the Sponge *Mycale* sp., Tetrahedron Letters 41 (2000) 7367-7371.

Romo, D., et al., Total Synthesis and Immunisuppressive Activity of (−)-Pateamine A and Related Compounds: Implementation of B-Lactam-Based Macrocyclization, J. Am. Chem. Soc. 1998, 120, 12237-12254.

Newman, D., et al., The Influence of Natural Products Upon Drug Discovery, Nat. Prod. Rep., 2000, 17, 215-234.

Hood, K., et al., Induction of Apoptosis by the Marine Sponge (*Mycale*) Metabolites Mycalamide A and Pateamine, Apoptosis, vol. 6, No. 3, pp. 207-219 (2001).

Cvetkovic, R., et al., ET-743, Drugs 2002: 62 (8): 1185-1192.

English Translation of Official Action mailed Sep. 4, 2009, in corresponding Application No. JP 2003-575916 filed Mar. 13, 2003.

Romo, D., et al., "Total Synthesis and Immunosuppressive Activity of (−)-Pateamine A and Related Compounds: Implementation of β-Lactam-Based Macrocyclization," J. Am. Chem. Soc. 120:12237-12254, 1998.

Rzasa, R.M., "Total Synthesis of the Novel, Immunosuppressive Agent (−)-Pateamine A from *Mycale* sp. Employing a β-Lactam-Based Macrocyclization," J.Am. Chem. Soc. 120:591-592, 1998.

* cited by examiner

1: R = H, Pateamine A (Native Pateamine A)
2: R = Boc (BoxPateamine A)

3: Des-mythl, des-amino PatA
(DMDA PatA)

Scheme 1. a) HOCH$_2$CCl$_3$, SOCl$_2$, benzene, reflux, 5 h, 61%; b) Br$_2$, CCl$_4$, CHCl$_3$, 0 °C, 3h, 36%; c) i) 2,6-lut., CH$_2$Cl$_2$, 25 °C, 12 h ii) TFAA, py., Hünig's base, 0→25 °C, 3 h, 64% (2 steps); d) TBAF, 20 mol% AcOH, THF, -20 °C, 1 h, 96% (10); 25 °C, 12 h, 75% (13); e) PPh$_3$, DIAD, THF, -20 °C, 2 h, 71%; f) 10% Cd/Pb, THF/1M NH$_4$OAc, 25 °C, 2 h, 99%; g) 2,4,6-trichlorobenzoyl chloride, Et$_3$N, DMAP, toluene, THF (0.001 M), 25 °C, 2 h, 92%; h) Pd(CaCO$_3$)/Pb, H$_2$, MeOH, 25 °C, 12 h, 80%; i) 10 mol% [Pd$_2$dba$_3$·CHCl$_3$:AsPPh$_3$=1:8], 17, THF, 25 °C, 2 h, 49%.

Scheme 2. a. PPh₃, DIAD, THF, -20 °C, 2h, 71% b. i) HF·py. THF, 25 °C, 24h, 86% ii) Et₄NCN, CH₂Cl₂, 25 °C, 5h, 65% c. Pd(CaCO₃)/Pb, H₂, MeOH, 12h, 99% d. 10 mol% [Pd₂dba₃·CHCl₃ : AsPPh₃ = 1 : 8], THF, 25 °C, 10-18h,11-76% e. i) 20% TFA, CH₂Cl₂, 0 °C, 15h, 95% ii) PhCOCl or (CF₃CO)₂O, DMAP, py., CH₂Cl₂, 25 °C, 5h, 99%.

Scheme 3. a. Ag$_2$O, MeI, CH$_3$CN, reflux, 9 h, 25%; b. i) TsCl, py., CH$_2$Cl$_2$ 0 °C, 8 h, 65% ii) dimethyl amine (g), THF, -78 °C, 6 h, 85%.

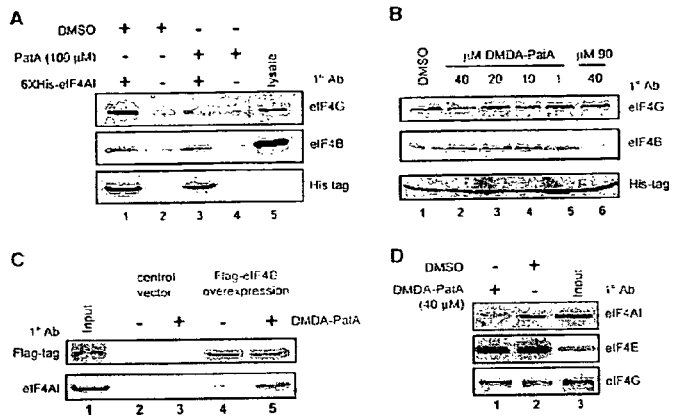
FIGURE 8
FIGURE 10
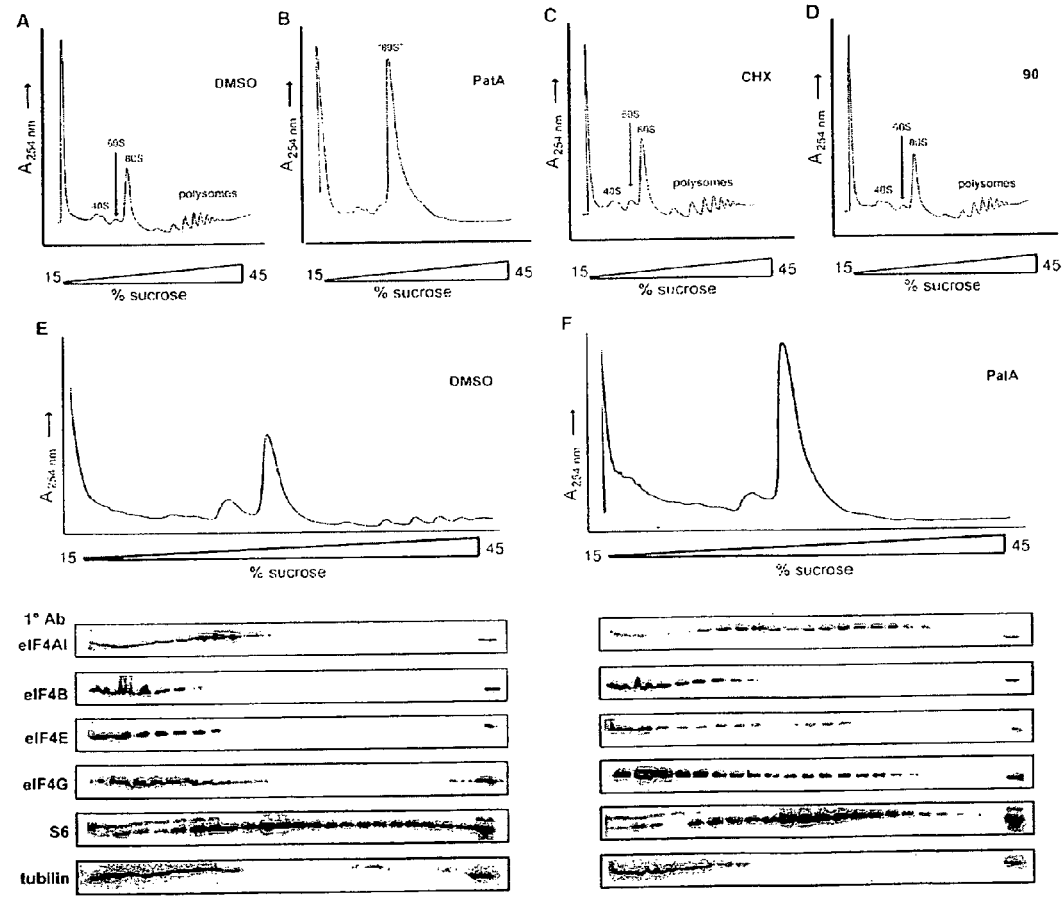

FIGURE 12

|  | IC$_{50}$ (nM) [$^3$H]-thymidine incorporation | | | | | |
|---|---|---|---|---|---|---|
|  | HaCaT | std dev | RKO | std dev | Hela | std dev |
| PatA | 0.42 | 0.03 | 0.38 | 0.02 | 0.72 | 0.08 |
| DMDA-PatA | 0.91 | 0.12 | 1.17 | 0.04 | 4.54 | 0.36 |
| 90 | NE (100 nM) | | NE (100 nM) | | NE (100 nM) | |

(a) K₂CO₃, DMF, 25 °C (78%); (b) Pd₂dba₃, AsPh₃, THF, 25 °C (29%).

ANTICANCER AGENTS AND USE

CROSS-REFERENCES TO RELATED APPLICATIONS

This application claims the benefit of U.S. Provisional Application No. 60/724,200, filed on Oct. 6, 2005, and is a continuation in part of U.S. patent application Ser. No. 10/388,257, filed on Mar. 13, 2003, now issued as U.S. Pat. No. 7,230,021, which claims the benefit of U.S. Provisional Application No. 60/364,347, filed on Mar. 13, 2002, each of which are incorporated herein by reference.

STATEMENT REGARDING FEDERALLY SPONSORED RESEARCH OR DEVELOPMENT

This invention was made with government support under grant number 5R01GM052964-07 awarded by the National Institutes of Health. The government has certain rights in the invention.

BACKGROUND OF THE INVENTION

Pateamine A (patA) was first isolated from the marine sponge Mycale found off the shores of New Zealand. The natural form bears a thiazole and an E,Z-dienoate within a 19-membered macrocycle and a trienylamine side chain. Two additional pateamines, pateamines B and C, were also isolated. Their structures differ from pateamine A only in the nature of the terminal group of the trienylamine side chain. The basic structure for these three isolated natural forms is shown below.

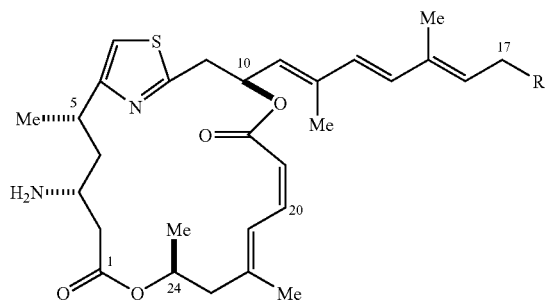

Pateamine A: R = NMe$_2$
B: R = NHMe
C: R = N(O)Me$_2$

Isolated pateamine A (native pateamine A) is a novel marine product that promises to be quite useful as a biochemical probe and which displays potent immunosuppressive properties with low cytotoxicity. In MLR (mixed lymphocyte reaction) assay, IC$_{50}$=2.6 nM while the LCV (lymphocyte viability assay)/MLR ratio is >1000. In comparing native pateamine A to cyclosporin A in a mouse skin graft rejection assay, native pateamine A resulted in a 15-day survival period as opposed to cyclosporin A having only a 10-day survival of the skin graft. Additionally, at high doses, toxicity was at 17% in these studies. For other dose levels, there was no toxicity. All doses were active.

It has also been found that native pateamine A specifically inhibits an intracellular step of the T-cell receptor signal transduction pathway leading to IL-2 transcription. Two syntheses of native pateamine A have been reported. The utility of these molecules as an immunosuppressant or immunostimulant is severely restricted because the molecule lacks stability. Additionally, natural sources of the molecule are limited. Thus, continuous development of synthetic pateamine derivatives having the same or lower toxicity, potent activity and increased stability is required.

Potent activity of native pateamine A in a mixed lymphocyte reaction and also in a mouse skin graft rejection assay have been observed. Native pateamine A originally showed activity in a mixed lymphocyte reaction, (IC$_{50}$ 2.6 nM) and in the mouse skin graft rejection assay. Native pateamine A was found to be more potent than cyclosporin A with only low toxicity at high doses but all doses were active. Native pateamine A may also inhibit a specific intracellular signaling pathway involved in T cell receptor-mediated IL-2 production. In addition to its effect on TCR signaling pathway, native pateamine A has been found to induce apoptosis in certain mammalian cell lines, especially those that are transformed with the oncogene Ras.

Analysis of native pateamine A structure reveals a rigid eastern half (C6-C24) including the thiazole, dienoate, and the triene sidechain, due to extended conjugation, and a more flexible western half (C1-C5). Furthermore, C3-Boc-PatA was found to have only 3-4 fold lower activity than native pateamine A.

Natural products have proven to be extremely useful as probes of biological processes. Examples include the immunosuppressive, microbial secondary metabolites, cyclosporin A, FK506, and rapamycin. Marine organisms have also been a rich source of bioactive compounds, which are proving useful as drug leads and biological probes. For example, bryostatin, epithilone, discodermolide and ecteinascidin show great potential as anti-cancer agents and have revealed novel biological mechanisms of action.

Immunomodulators are useful for treating systemic autoimmune diseases, such as lupus erythematosus and diabetes, as well as immunodeficiency diseases. Immunomodulators are also useful for immunotherapy of cancer or to prevent rejections of foreign organs or other tissues in transplants, e.g., kidney, heart, or bone marrow. Examples of immunomodulators include: FK506, muramylic acid dipeptide derivatives, levamisole, niridazole, oxysuran, flagyl, and others from the groups of interferons, interleukins, leukotrienes, corticosteroids, and cyclosporins. Many of these compounds, however, have undesirable side effects and/or high toxicity in a subject in need thereof. New immunomodulator compounds are, therefore, needed to provide a wider range of immunomodulator function for specific areas with a minimum of undesirable side effects.

Unfortunately, many immunomodulators available currently have undesirable side effects and/or high toxicity and are often difficult to synthesize in pharmacologically effective amounts. What is needed is one or more immunomodulative compounds that may be synthetically produced in effective amounts and provide a broad spectrum of activity (e.g., immunomodulator function) with increased stability and with less undesirable side effects.

BRIEF SUMMARY OF THE INVENTION

As described, compositions provided herein overcome many limitations found with native pateamine A by having more potent activity, improved stability and the same or lower toxicity. In addition, novel actions of the native protein and its analogs as described herein provide useful means for identifying anticancer and antiproliferative agents, targeting molecules for inhibition of translation initiation, identifying probes for eukaryotic translation initiation, and creating improved immunomulating compounds.

Described herein include compositions, all related stereoisomers as well as pharmaceutically acceptable salts provided as simplified analogs of pateamine A, in which the analogs generally are devoid of the C3-amino and C5-methyl groups, also referred to as desmethyl, desamino-pateamine A. Suitable analogs provide anticancer and antiproliferative effects in vivo and in vitro by a novel mechanism of action as described herein for pateamine A and its analogs, including inhibition of eIF4A-dependent translation initiation. As with pateamine A, as described herein, suitable analogs cause cell cycle arrest or induce apoptosis in transformed cells. However, toxicity of such compounds to slow growing normal cells is low. In addition, such analogs, like pateamine A, target translation initiation factors and are useful as anticancer and antiproliferative agents in subjects in need thereof. Moreover, the analogs, like pateamine A, are valuable molecular probes for evaluation of eukaryotic translation initiation and as lead compounds for development of improved anticancer agents.

In one form, described herein include compositions as summarized below (Formula I):

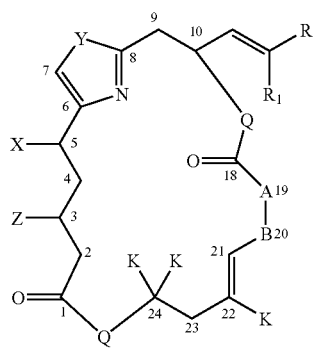

and its pharmaceutically acceptable salts, wherein:

A-B is ethane, (K) and (Z)-ethene, (K) and (Z)-substituted ethene, or ethyne,

K is hydrogen or C1-C3 alkyl,

Q is NH or O,

X is hydrogen, hydroxy, alkoxy, alkyl, aminocarbonyl, amino, alkylamino, dialkylamino, or alkoxycarbonylamino, Y is S, NH, or O, Z is hydrogen, hydroxy, aminocarbonyl, alkylamino, dialkylamino or alkoxycarbonylamino, but not t-butoxycarbonylamino when $R_4$ is dimethylamino, $R_1$ is hydrogen or C1-C3 alkyl, and R is selected from the following:
(a) Alkene of the formula:

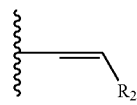

wherein $R_2$ is selected from alkyl, alkylhydroxy, alkylalkoxy, alkylamino, alkylaminoalkyl, or alkylaminodialkyl;

(b) Alkenylaryl of the formula:

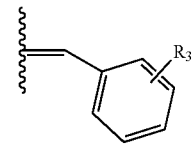

wherein $R_3$ is selected from hydrogen, alkyl, alkenyl, alkynyl, hydroxy, alkoxy, amino, alkylamino, dialkylamino, trifluoromethane, or fluoro;

(c) Methyldienylpentyl of the formula:

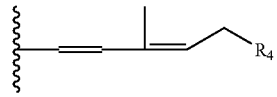

wherein $R_4$ is selected from hydrogen, alkyl, alkenyl, alkynyl, hydroxy, alkoxy, amino, alkylamino, or dialkylamino; and (d) Methylalkenylpentyl of the formula:

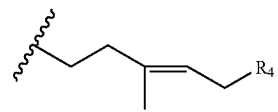

wherein $R_4$ is selected from hydrogen, alkyl, alkenyl, alkynyl, hydroxy, alkoxy, amino, alkylamino, or dialkylamino.

Such compositions include compounds with a general formula provided below:

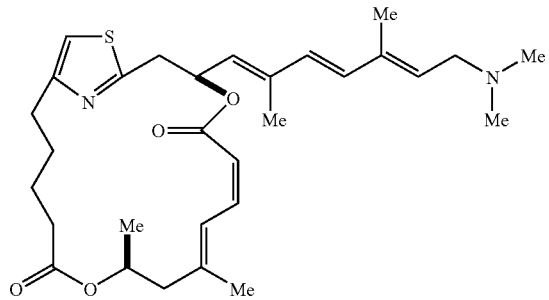

3: Des-methyl, des-amino PatA
(DMDAPatA)

and their pharmaceutically accepted salts.

Further described herein include pharmaceutical compositions, methods of making and methods of use, such as for therapeutic treatment of a subject in need thereof. Such pharmaceutical compositions are generally useful as immunoregulators, immunomodulators and anti-proliferative or anti-cancer agents due to their breadth of activity, including anti-tumor, anti-fungal and anti-cancer properties. Such compositions are useful in graft versus host rejection therapy, autoimmune diseases, chemotherapy and/or treatment of infectious diseases.

Analogs and derivatives of PatA inhibit translation through a novel mechanism and serve as valuable molecular probes for eukaryotic translation initiation and as lead compounds for the development of new and improved anticancer agents.

Such analogs and derivatives as provided herein are useful in providing one or more assays and kits for the detection and/or high throughput screening of compounds or binding products and/or targets of pateamine A. For example by immobilization of a tagged pateamine A or a tagged analog of pateamine A (e,g., biotinylated pateamine A or B-patA) on a substrate surface (coated or uncoated with another compound), additional competitive compounds may be identified that bind pateamine A or its analogs. A secondary labeled target (e.g., eIF4A) is introduced and in the absence of additional compounds that bind pateamine A or its analogs, the target remains bound to B-patA.

Similar assays and kits are provided to further identify interactions between molecules involved in translation initiation (e.g., interaction between eIF4A and eIF4G) and in mechanisms of stress granule production by PatA and its analogs5) Use of PatA and DMDA-PatA in a series of cancer cells (see table), including but not limited to leukemia, colon, cervical, breast and other cancers.

Compositions as described herein are suitable compounds for inhibition of angiogenesis and treatment of cancers, such as breast cancer and those relying on bcr-Abel oncogenes.

Those skilled in the art will further appreciate the above-noted features and advantages of the invention together with other important aspects thereof upon reading the detailed description that follows in conjunction with the drawings.

BRIEF DESCRIPTION OF THE DRAWINGS

For more complete understanding of the features and advantages of the present invention, reference is now made to a description of the invention along with accompanying figures, wherein:

FIGS. 8A-D depict pateamine A effects on the affinity of eIF4A for associated proteins showing (A-B) 6XHis-eIF4AI captured proteins from HeLa lysates treated as indicated identified by SDS-PAGE and immunoblotting with indicated antibodies, (C) co-immunoprecipitation of eIF4AI from 293T cell lysate with transiently overexpressed Flag-tagged eIF4B, and (D) proteins captured by m$^7$GTP-Sepharose resin in the presence of DMDA-PatA or DMSO were visualized by immunoblotting with indicated antibodies;

FIGS. 10A-F depict disruption of cellular (poly)ribosome profile and redistribution of translation initiation factors under PatA treatment, wherein (A-D) polyribosome profiles determined from 293T cells after 30 min treatment with (A) DMSO, (B) 100 nM PatA, (C) 100 μg/ml CHX, D: 100 nM analog 90, and (E-F) polyribosome profiles determined from HeLa cells after 1 h treatment with (E) DMSO, or (F) 20 nM PatA;

FIG. 12 is a table depicting inhibition of cell proliferation by pateamine A and DMDA-PatA;

DETAILED DESCRIPTION OF THE INVENTION

Figure 1:
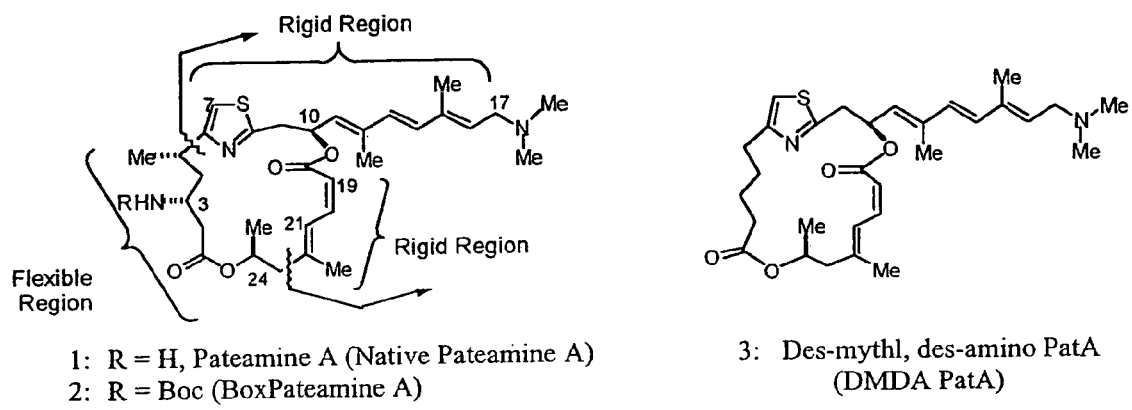
FIG. 1 shows chemical structures of native pateamineA, boc pateamine A and DMDA PatA.

Although making and using various embodiments are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

Described herein are compositions that include simplified PatA derivatives (e.g., desmethyl, desamino PatA, DMDA PatA, 3 as shown in FIG. 1) was prepared by employing a convergent Hantzsch coupling strategy via total synthesis of the molecule. This derivative was prepared in 10 fewer synthetic steps relative to native pateamine A and was found to exhibit equal to greater potency ($IC_{50}$ 0.81±0.27 nM) in inhibition of IL-2 production relative to native pateamine A ($IC_{50}$ 4.01±0.94 nM). In addition, as a means to find more stable derivatives and gain further insights into structure-activity relationships, PatA derivatives have been synthesized and studied in the IL-2 reporter gene assay. Many of these derivatives displayed lower potency but marked stability relative to the natural product and provide further insights into the nature of the binding domain required for activity.

A hypothesis was developed regarding a potential binding and scaffolding domain in the immunosuppressive marine natural product, pateamine A ("native pateamine A"). Premised on preliminary biological and molecular modeling studies, an analysis of the native pateamine A structure was prepared. A simplified derivative. DMDA PatA, devoid of the C3-amino and C5-methyl groups was found to have greater potency than native pateamine A in the IL-2 reporter gene assay. As evidenced in the analysis, the sector of the molecule (C1-C5) serves as a scaffold for the remaining conformationally rigid sectors (C6-C24) of the molecule including the thiazole, the dienoate, and the triene sidechain. This result is reminiscent of similar receptor binding proposals put forth in early studies of other cyclic peptide and macrocyclic immunosuppressive natural products, namely cyclosporin A, FK506, and rapamycin. However, in those cases, the domains were renamed effector and binding domains because these natural products were found to bind two cellular proteins acting as a molecular glue.

Importantly, the synthesis of this derivative (14 versus 24 steps from crotyl alcohol; longest linear sequence) is greatly simplified relative to PatA (1 as shown in FIG. 1), native pateamine A. As previously observed, C3-amino acylated derivatives retain activity in the IL-2 reporter gene assay. In addition, a subtle interplay between the dienoate sector (C18-C22) and the triene sidechain was revealed when dienoate versus enynoate-containg macrocycles were compared. The importance of macrocycle conformation and sidechain functionality in binding of native pateamine A to its putative cellular receptor is evidenced.

A representative composition as described herein is Formula I as set out below.

(I)

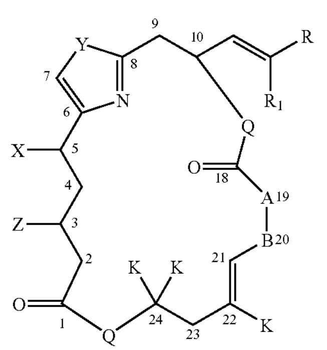

and its pharmaceutically acceptable salts, wherein

A-B is ethane, (F) and (Z)-ethene, (F) and (Z)-substituted ethene, or ethyne,

K is hydrogen or C1-C3 alkyl,

Q is NH or O,

X is hydrogen, hydroxy, alkoxy, alkyl, aminocarbonyl, amino, alkylamino, dialkylamino, or alkoxycarbonylamino;

Y is S, NH, or O,

Z is hydrogen, hydroxy, aminocarbonyl, alkylamino, dialkylamino or alkoxycarbonylamino, but not t-butoxycarbonylamino when $R_4$ is dimethylamino, $R_1$ is hydrogen or C1-C3 alkyl, and R is selected from the following:

(a) Alkene of the formula:

wherein $R_2$ is selected from alkyl, alkylhydroxy, alkylalkoxy, alkylamino, alkylaminoalkyl, or alkylaminodialkyl;

(b) Alkenylaryl of the formula:

wherein $R_3$ is selected from hydrogen, alkyl, alkenyl, alkynyl, hydroxy, alkoxy, amino, alkylamino, dialkylamino, trifluoromethane, or fluoro;

(c) Methyldienylpentyl of the formula:

wherein $R_4$ is selected from hydrogen, alkyl, alkenyl, alkynyl, hydroxy, alkoxy, amino, alkylamino, or dialkylamino; and (d) Methylalkenylpentyl of the formula:

wherein $R_4$ is selected from hydrogen, alkyl, alkenyl, alkynyl, hydroxy, alkoxy, amino, alkylamino, or dialkylamino.

In addition, described herein includes compositions with a formula:

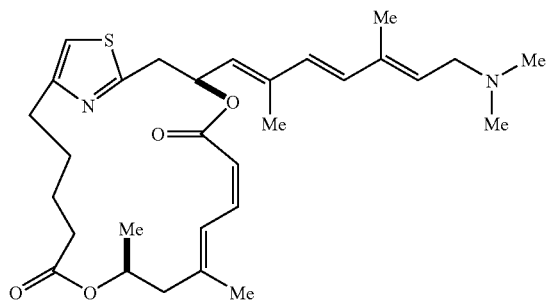

3: Des-methyl, des-amino PatA
(DMDAPatA)

and their pharmaceutically accepted salts.

Another embodiment comprises compositions having a formula:

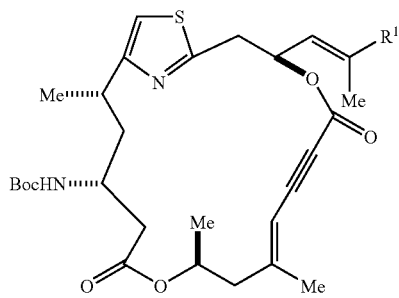

also represented as a Boc enyne macrocycle, and their pharmaceutically accepted salts, wherein $R^1$ is selected from the following:

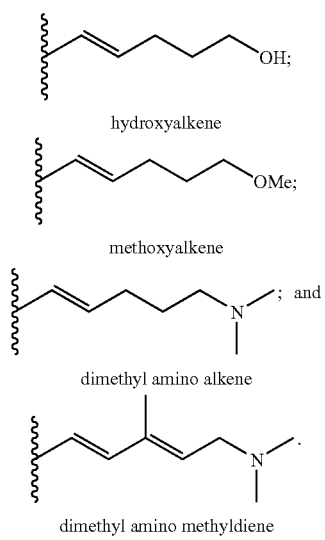

hydroxyalkene methoxyalkene

; and dimethyl amino alkene

.

dimethyl amino methyldiene

Another embodiment comprises compositions having a formula:

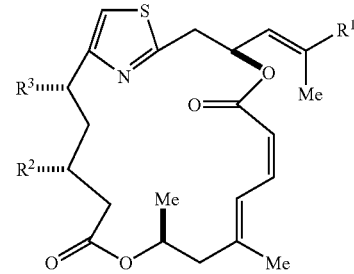

also represented as a diene macrocycle, and its pharmaceutically accepted salts, wherein $R^1$ is selected from hydroxyalkene, methoxyalkene, dimethyl amino alkene and dimethyl amino methyldiene; $R^2$ is selected from amino, t-butoxycarbonylamino, hydrogen, phenoxycarbonylamino, and tri-fluromethylacetamide; and $R^3$ is selected from methyl and hydrogen. Examples of some preferred combinations are set out in TABLE 1 below, wherein the following abbreviations are used: $NH_2$ is amino, NHBoc is t-butoxycarbonylamino, H is hydrogen, NHC(O)OPh is phenoxycarbonylamino, NHC(O)$CF_3$ is tri-fluromethylacetamide, and Me is methyl.

TABLE 1

| $R^1$ | $R^2$ | $R^3$ |
|---|---|---|
| (dimethylamino methyldiene) | $NH_2$ | Me |
| (dimethylamino methyldiene) | NHBoc | Me |
| (dimethylamino methyldiene) | H | H |
| (hydroxyalkene) | NHBoc | Me |
| (methoxyalkene) | NHBoc | Me |
| (dimethyl amino alkene) | NHBoc | Me |
| (dimethyl amino alkene) | NHC(O)OPh | Me |

TABLE 1-continued

| R¹ | R² | R³ |
|---|---|---|
| 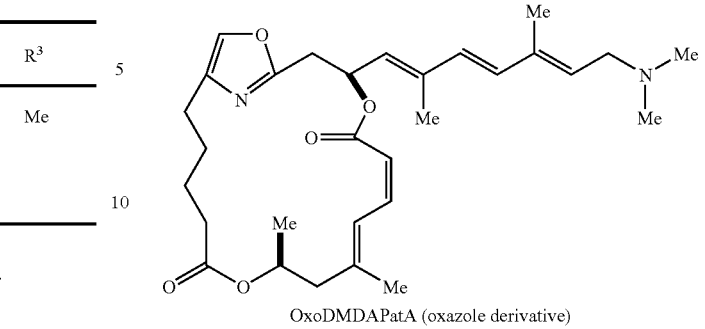 | NHC(O)CF₃ | Me |

Additional embodiments are represented below.

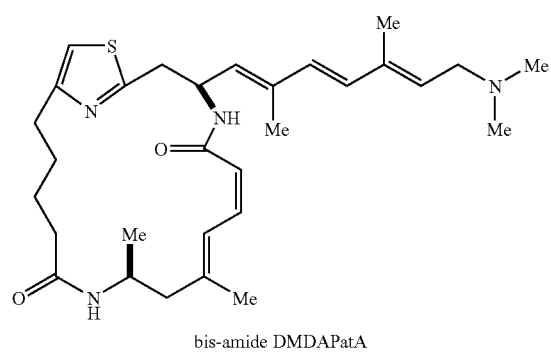
bis-amide DMDAPatA

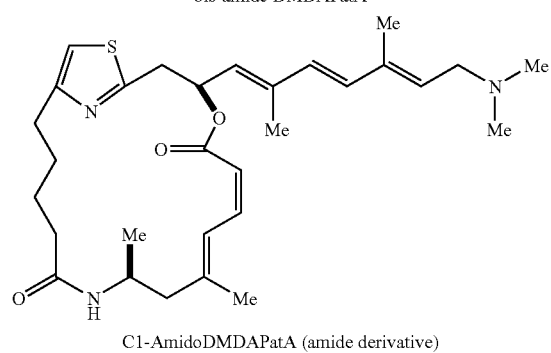
C1-AmidoDMDAPatA (amide derivative)

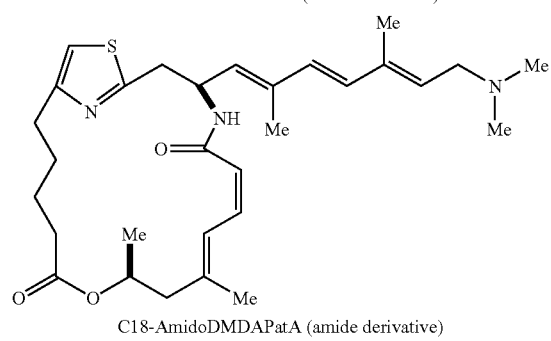
C18-AmidoDMDAPatA (amide derivative)

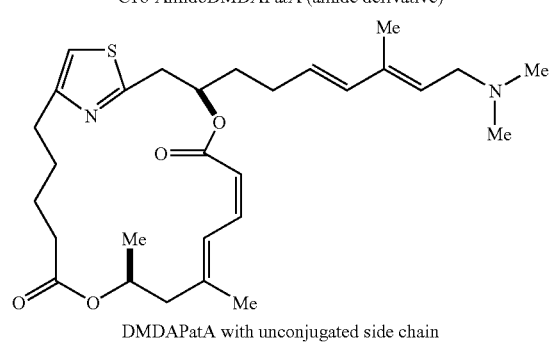
DMDAPatA with unconjugated side chain

OxoDMDAPatA (oxazole derivative)

AminoDMDAPatA (imidazole derivative)

Truncated PatA

C24-Methyl DMDAPatA (methylated derivative): X, Y = O
C24-Methyl C1-Amido DMDAPatA (methylated derivative): X = NH or NR, Y = O
C24-Methyl C18-Amido DMDAPatA (methylated derivative): X = O; Y = NH or NR
C24-Methyl C1, C-18-BisAmido DMDAPatA (methylated derivative): X, Y = NH or NR (where R = alkyl or aryl)

and their pharmaceutically accepted salts.

Compositions described herein also include labeled derivatives of PatA, such as biotinylated derivatives of PatA, and methods of making, wherein such methods generally comprise the steps of:

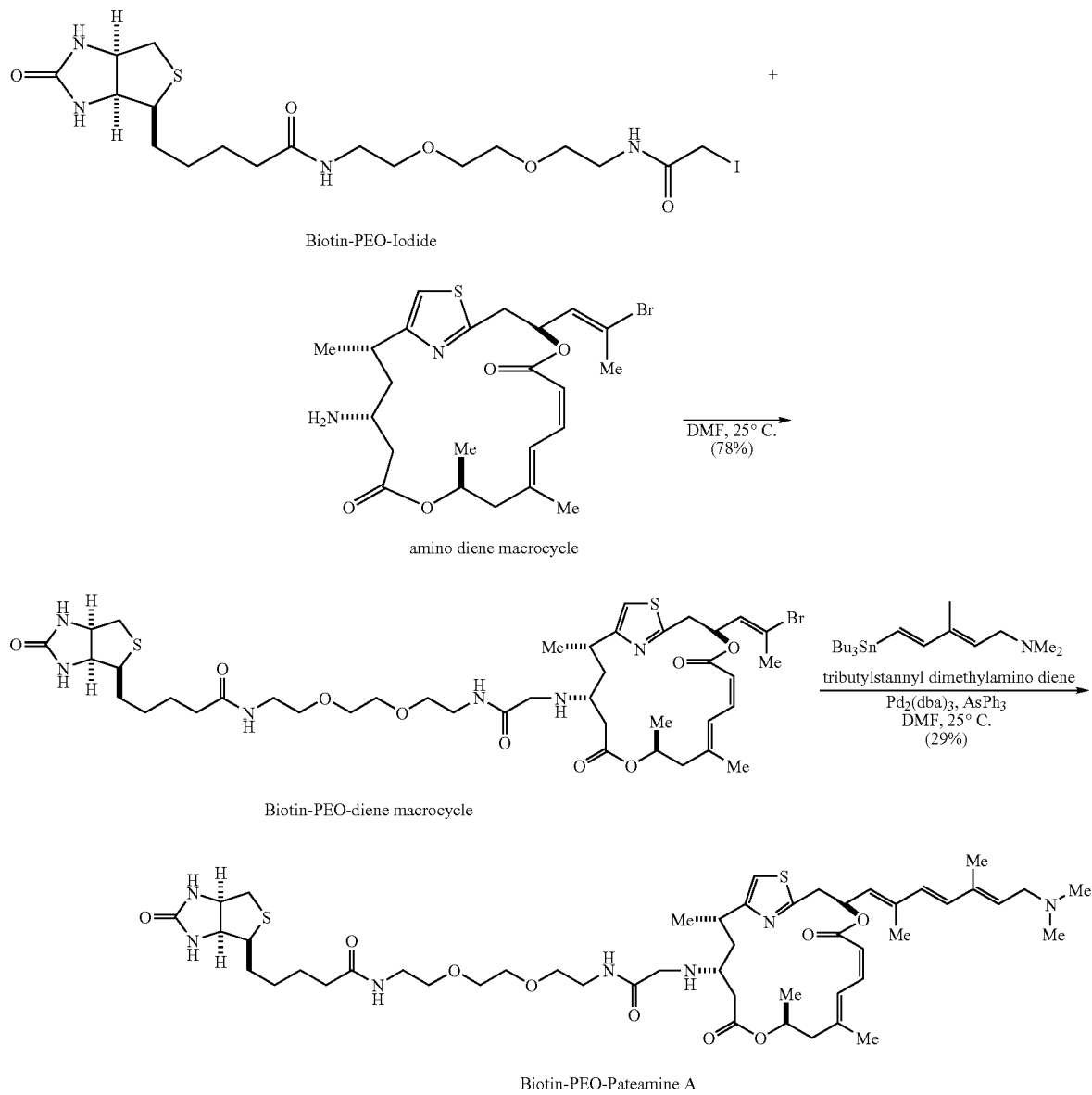

Biotin-PEO-Iodide amino diene macrocycle

Biotin-PEO-diene macrocycle

Biotin-PEO-Pateamine A

Native pateamine A consists of separate binding (C6-C24) and scaffolding (C1-C5) domains. Molecular modeling studies and the total synthesis and biological analysis of a simplified derivative, devoid of the C3-amino and C5-methyl groups (DMDA PatA) is herein provided. The synthesis of DMDA PatA incorporates a convergency-building strategy involving a Hantzsch thiazlole coupling. In addition, the synthesis and biological testing of other pateamine A derivatives are provided having improved stability as compared to the native pateamine A structure. In particular, stabilization of the acid sensitive triallylic acetate moiety (i.e. C10 position) is provided in such derivatives.

Molecular Modeling Studies of Native Pateamine A and DMDA PatA. The presence of binding and scaffolding domains in native pateamine A were verified using molecular mechanics/dynamics (MM/MD) calculations. Simulated annealing was used to determine the conformational space of native pateamine A. An overlay of the 100 structures obtained from the simulated annealing, in which the C11-C16 segment of the triene moiety is overlaid, shows a "mushroom" structure. From the 100 structures, 13 unique conformers (Table 1) were identified within 3 kcal/mol of the lowest energy conformer. Extensive NMR studies of native pateamine A by the Munro and Blunt groups revealed a key cross-ring nOe in $CDCl_3$ between $H_{C3}$ and $HC_{C21}$ (see FIG. 1 for numbering scheme), indicating that these two hydrogen atoms should be less than approximately 3 Å of one another. Robert, G. C. K., Ed.; Osford Univ. Press, 1993, Ch. 10. The MM/MD calculations gave conformers that had $H_{C3}$—$H_{C21}$ distances ranging from 3.2 to 7.1 Å, and a distance of 4.3 Å for the lowest energy conformation.

To obtain better energetics and refined structures, the 13 unique conformations determined at the MM/MD level of theory, were optimized at the DFT level of theory using the B3LYP functional. Frequency calculations were performed to obtain free energies and ensure that each structure had zero imaginary frequencies. TABLE 2 lists the CVFF relative energies (ΔE(0K)) and $H_{C3}$—$H_{C21}$ bond distances, and B3LYP relative free energies (ΔG°) and $H_{C3}$—$H_{C21}$ bond distances for the 13 unique conformers.

TABLE 2

Energetics (kcal/mol) and $H_{C3}$-$H_{C21}$ bond distances (Å) for the 12 Unique PatA (DMDA PatA) conformers at the CVFF and B3LYP levels of theory.

| | CVFF | | B3LYP[a] | |
|---|---|---|---|---|
| Conformer | ΔE (0K) (kcal/mol) | $H_{C3}$-$H_{C21}$ Distance (Å) | ΔG° (kcal/mol) | $H_{C3}$-$H_{C21}$ Distance (Å) |
| A | 0.0 | 4.34 | 9.0 (7.9) | 4.96 (4.83) |
| B | 0.3 | 4.24 | 8.1 | 4.92 |
| C | 0.4 | 3.23 | 4.8 | 3.28 |
| D | 0.8 | 6.09 | 10.1 | 6.10 |
| E | 1.3 | 3.94 | 0.0 (0.0) | 4.52 (4.37) |
| F | 1.4 | 6.17 | 13.0 | 5.99 |
| G | 1.4 | 3.24 | 3.3 (2.3) | 3.30 (3.26) |
| H | 2.0 | 3.78 | 3.3 | 3.57 |
| I | 2.0 | 3.75 | 9.3 | 3.37 |
| J | 2.1 | 3.22 | 7.5 | 3.50 |
| K | 2.5 | 3.78 | 8.2 | 3.43 |
| L | 2.8 | 5.72 | 4.6 | 5.81 |
| M | 2.8 | 3.79 | 3.2 | 3.54 |

[a]Values in parenthesis are for the corresponding DMDA PatA conformer;
CVFF is Consistent Valence Force Field;
DFT is Density Functional Theory;
B3LYP is Becke three parameter hybrid exchange functional and the Lee-Yang-Parr correlation functional.

A large discrepancy between the CVFF and B3LYP energies with an underestimation of the difference in conformational energy by CVFF is evident. While CVFF energies were quite different from B3LYP, the structures were similar. An overlay of the 13 B3LYP optimized conformations was made. Inspection of the overlay revealed two basic conformations: 1) lower energy extended structures, leaving the majority of the triene moiety exposed and 2) higher energy conformations having the macrocycle folded over the triene moiety. DFT is known to underestimate van der Waal interactions; therefore, the $H_{C3}$—$H_{C21}$ distance appeared to be underestimated.

The lowest energy conformer identified at the B3LYP level, $H_{C3}$—$H_{C21}$, has a distance of 4.5 Å, longer than anticipated in light of the cross-ring nOe. Another conformer has only 3.3 kcal/mol higher in energy than the lowest energy conformer having an $H_{C3}$—$H_{C21}$ distance of 3.3 Å, in much better agreement with the cross-ring nOe.

Of the 13 conformations studied, four have an $H_{C3}$—$H_{C21}$ distance less than 4 Å, and within 5 kcal/mol of the lowest energy conformer. An overlay of conformations are within 5 kcal/mol of the lowest energy conformer and have an $H_{C3}$—$H_{C21}$ distance consistent with the NMR data. As shown in FIG. 1, the extended conformations differ primarily in the C1-C5 region, indicating a flexible region, while the thiazole, triene, and dienoate regions (C6-C22) are relatively rigid in nature. The thiazole has two conformations that are approximately 180 degrees from each other i.e. simultaneous rotation around C5-C6 and C8-C9. Therefore, the relative position of the plane containing the thiazole ring atoms in these conformations changes very little, but the nitrogen and sulfur atoms exchange positions.

Simulated annealing was also used to investigate the conformational space of DMDA PatA. An overlay of the 100 structures obtained from the simulated annealing, in which the C11-C16 segment of the triene moiety is overlaid, shows a "mushroom" structure similar to that found for native pateamine A. Due to the computational cost of the B3LYP calculations and the similar results obtained from the CVFF calculations, only three conformations (A, E, and G) were optimized at the B3LYP level of theory for DMDA PatA. The relative free energies for DMDA PatA are similar to those found for native pateamine A (TABLE 2) with the difference in free energy between conformations being about 1 kcal/mol less than that for native pateamine A. An overlay of the lowest energy conformer of native pateamine A and the corresponding DMDA PatA conformer was used. In addition, an overlay of the lowest energy conformer that also satisfies the nOe constraint for native pateamine A and the corresponding DMDA PatA conformer was used. As can be seen by this analysis, native pateamine A and DMDA PatA have similar structures and energetics using similar minimization parameters.

These structural studies, in combination with the previously reported potent biological activity of acylated C3-amine derivatives (e.g. 2, R=Boc), suggested the presence of possible separate binding (C6-C24) and scaffolding (C1-C5) domains in the native pateamine A structure. Romo, D. et al. J. Am. Chem. Soc. 1998, 120, 12237-12254. Many protein ligands are known to change conformations on binding to their receptors or alternatively, the binding event leads to a more defined conformation. Rosen, M. K et al., Bio. Med. Chem. Lett. 1992, 2, 747-753. The preliminary biological data and the modeling described above, allows synthesis of a simplified PatA derivatives including DMDA PatA that are devoid of the C3-amino and C5-methyl groups.

Figure 2:
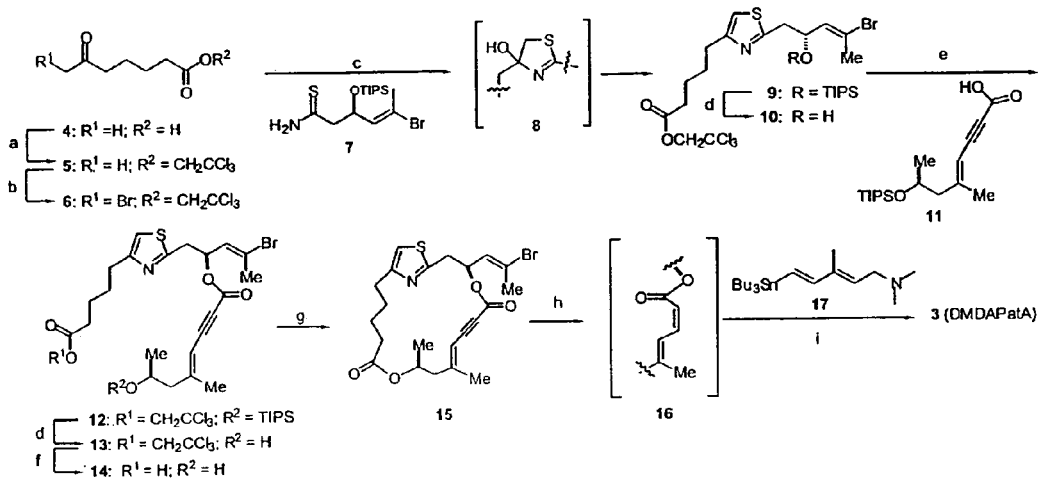
FIG. 2 depicts the synthesis of DMDA PatA using Scheme 1.

Synthesis of PatA Derivatives. For the synthesis of DMDA PatA 3, a more convergent strategy to the C1-12 thiazole-containing fragment employing a Hantzsch coupling reaction (FIG. 2, Scheme 1). Pattenden made use of a related-strategy in the synthesis of native pateamine A. Remuinan, M. J. et al. Tetrahedron Lett. 2000, 41, 7367-7371. As shown in FIG. 2, the synthesis of the requisite bromoketone 6 commenced with esterification and bromination of 6-oxoheptanoic acid (4). Hantzsch thiazole coupling between this bromoketone and the previously described thioamide 7 using modified Meyers' conditions provided thiazole 9 in good overall yield (64%). Romo, D., et al., J. Am. Chem. Soc. 1998, 120, 12237-12254; Aguilar, E.; Meyers, A. I. Tetrahedron Lett. 1994, 35, 2473-2476. A critical prerequisite for optimal yields in this coupling was purification of the intermediate thiazoline 8 prior to the dehydration step in contrast to our previous applications of this reaction, in which this process could be performed in a single pot. Romo, D., et al., J. Am. Chem. Soc. 1998, 120, 12237-12254. Deprotection of the TIPS ether followed by a Mitsunobu coupling with the TIPS protected version of the previously described enyne acid 11 gave the macrocyclic precursor 12. Id. Deprotection of the TIPS ether and trichloroethyl ester of diester 12 followed by Yamaguchi macrocyclization gave macrocycle 15. Dong, Q., et al., Tetrahedron Lett. 1995, 36, 5681-5682; Inanaga, J., et al., Chem. Soc. Japan 1979, 52, 1989-1993. Subsequent Lindlar reduction gave E,Z-diene 16 and Stille coupling with the previously described dienyl stannane 17 gave DM DAPatA (3) in 11 steps from thioamide 7. Id., see also, Farina, V.; Krishnan, B. J. Am. Chem. Soc. 1991, 113, 9585-9595.

Figure 3:
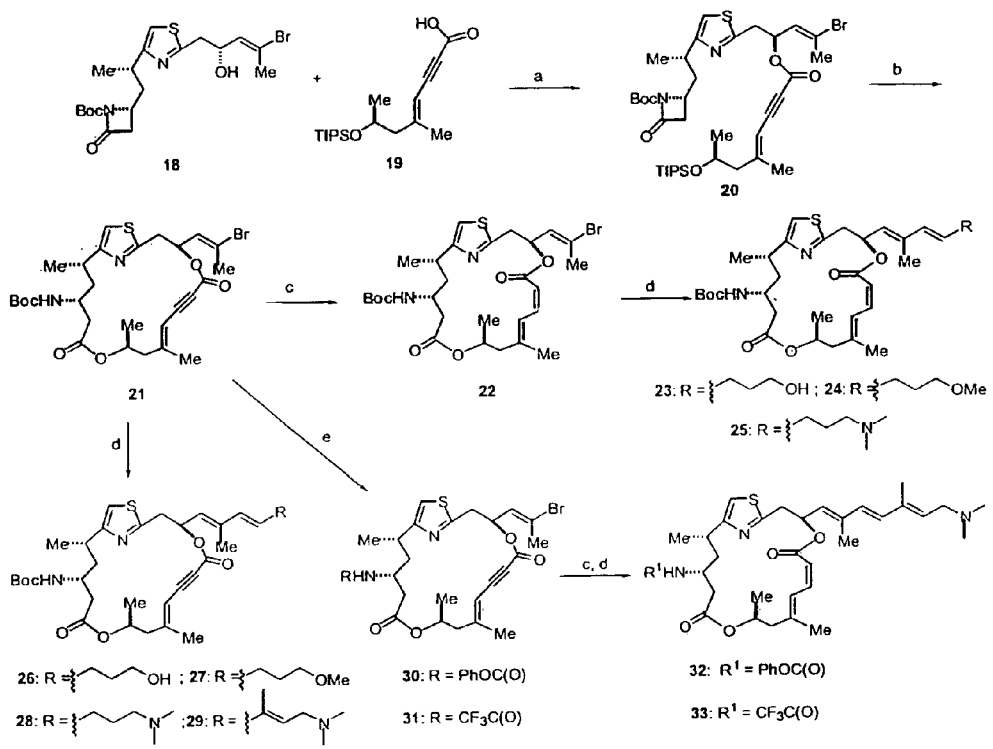
FIG. 3 shows the synthesis of additional PatA derivatives using Scheme 2.

The synthesis of additional PatA derivatives with only minor structural variations began with the previously described β-lactam 18 (FIG. 3, Scheme 2). The synthesis of all derivatives in this series mirrored that previously reported for the total synthesis of native pateamine A. Romo, D., et al., J. Am. Chem. Soc. 1998, 120, 12237-12254. Introduction of side chain via a Stille coupling reaction as the final step in the synthesis is preferred partly to the polarity introduced by the tertiary amine, but primarily due to the instability associated with the triallylic ester moiety.

Figure 4:
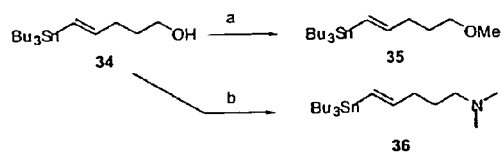
FIG. 4 shows the required stannanes for side chain-modified PatA derivatives using Scheme 3.

Derivatives 23-25 and 26-28 were prepared to determine the structural flexibility tolerated on the sidechain of PatA and also to improve stability of the acid labile triallylic acetate moiety by removal of one unsaturation. For this purpose, the required stannanes for sidechain-modified PatA derivatives were prepared by standard conditions and stannylcupration was performed as described previously for vinyl stannane 17 (FIG. 4, Scheme 3). Romo, D., et al., J. Am. Chem. Soc. 1998, 120, 12237-12254. The C3-Boc protecting group had previously been found to have a minor effect on activity (2-3 fold decrease in activity), therefore for ease of handling, this group was retained in all derivatives. PatA derivatives bearing a dienyl alcohol (23 and 26) and a dienyl methyl ether (26 and 27) were synthesized. In addition, derivative 25 bearing the identical side-chain found in PatA with the exception of one unsaturation and the C16 methyl group was prepared. The effect of a more rigid macrocycle (i.e. enyne vs dienoate) on biological activity was investigated by synthesis of enynes 26-29. These derivatives were readily prepared by omission of the Lindlar reduction step (FIG. 3, Scheme 2).

Due to the aforementioned activity of C3-Boc PatA, two additional C3-amino derivatives were prepared with the expectation that they should have similar potency. In this regard, the C3-phenyl carbamate 32 and the C3-trifluoroacetamide 33 were synthesized by deprotection of Boc-macrocycle 21 followed by acylation to give macrocycles 30 and 31. Subsequent Lindlar reduction and Stille reaction gave the C3-acylated derivatives 32 and 33.

The ability of these derivatives to inhibit T cell receptor-mediated IL-2 production was analyzed using an IL-2 reporter gene assay. In this assay, a plasmid encoding a reporter gene (luciferase) under the control of the IL-2 promoter was first introduced into Jurkat T cells by transfection. The transfected Jurkat T cells are then stimulated with two pharmacological agents, phorbol myristyl acetate (PMA), which activates protein kinase C, and inonmycin, which allows calcium ion to enter T cells to activate calmodulin and calcineurin. Together, PMA and ionomycin recapitulate T cell receptor signaling, leading to the activation of the luciferase reporter gene by activating the IL-2 promoter. The ability of PatA and its analogs to block T cell receptor-mediated IL-2 expression was measured by their effects on this reporter gene assay. Su, B., et a., Cell 1994, 77, 727-736.

Most derivatives were in general less potent than native pateamine A, PatA (1). As expected, the C3-phenyl carbamate derivative 32 was found to have comparable activity (~15 nM) to BocPatA (2, 16-17 nM). However, the reduced activity of the trifluoroacetamide 33 (~303 nM) may be due to the increased polarity of this substituent leading to poorer cell permeability. However, a possible trend was observed upon comparison of dienoate macrocyclic (23-25) versus enynoate macrocyclic (26-29) derivatives. Enyne derivatives having an a more rigid macrocycle than the natural product and bearing oxygen rather than nitrogen at the terminus of the side chain (i.e. 26 and 27) were found to have activities in the IL-2 reporter gene assay ranging from 55-335 nM. However, enyne derivatives (i.e. 28 and 29) with side chains more closely resembling the natural product (i.e. amino end groups) had no activity. Furthermore, the dienoate derivatives (i.e. 23 and 24) having macrocycle conformations similar to the natural product but bearing oxygen rather than nitrogen at the terminus of the side chain had very low activity. However, once nitrogen is introduced into the sidechain, as in derivative 25, activity is restored (328 nM). Thus, it would appear that an oxygenated side-chain compensates for the change in macrocycle conformation that occurs upon introduction of an enyne. However, oxygen rather than nitrogen on the side chain leads to low activity when coupled to the natural dienoate-containing macrocycle. It is imaginable that changes in the conformation of the macrocycle results in a reorientation of the sidechain that cannot be accommodated by the protein receptor. However, replacement of a charged tertiary amino group with a neutral and smaller hydroxyl or methoxy groups allows for the binding of the derivative with these two structural alterations.

The derivative providing direct support for the binding/scaffolding hypothesis is DMDA PatA 3. This derivative displayed similar to greater potency ($IC_{50}$ 0.8±0.3 nM) relative to natural pateamine PatA ($IC_{50}$ 4.0±0.9 nM) in its ability to inhibit expression of the IL-2 reporter gene in stimulated Jurkat T cells. The hypothesis that the C1-C5 segment of native pateamine A does not interact directly with its putative cellular receptor but may serve as a scaffold to define and maintain the macrocyclic conformation is supported in accordance with the results above. Importantly, DMDA PatA 3 is more stable than native pateamine A (stable in $CDCl_3$ for 3-4 weeks at 25° C.). Native pateamine A decomposes in $CDCl_3$ at 25° C. in <10 minutes.

TABLE 3

IL-2 reporter gene assay (transfected Jurkat cells) activity of pateamine A and derivatives.

| cmpd. | $R^1$ | $IC_{50}$ (nM) | cmpd. | $R^1$ | $R^2$ | $R^3$ | $IC_{50}$ (nM) |
|---|---|---|---|---|---|---|---|
| 26 | (chain with OH) | 335 ± 183 | Pat A(1) | (chain with N) | | $NH_2$ | Me | 4.01 ± 0.938 |

TABLE 3-continued

IL-2 reporter gene assay (transfected Jurkat cells) activity of pateamine A and derivatives.

| cmpd. | $R^1$ | $IC_{50}$ (nM) | cmpd. | $R^1$ | $R^2$ | $R^3$ | $IC_{50}$ (nM) |
|---|---|---|---|---|---|---|---|
| 27 | (CH₂)-OMe chain | 55.1 ± 15.5 | 3 | branched N(Me)₂ chain | H | H | 0.808 ± 0.274 |
| 28 | chain-N(Me)₂ | NA[a] | 23 | chain-OH | NHBoc | Me | >1000[b] |
| 29 | branched chain-N(Me)₂ | NA[a] | 24 | chain-OMe | NHBoc | Me | >1000[b] |
| | | | 25 | chain-N(Me)₂ | NHBoc | Me | 328 ± 119 |
| | | | 32 | chain-N(Me)₂ | NHC(O)OPh | Me | 15.4 ± 6.05 |
| | | | 33 | chain-N(Me)₂ | NHC(O)CF₃ | Me | 303 ± 93.2 |

[a]Not active.
[b]Inhibition activity was observed, but it did not reach 50% even with the highest concentration tested.
[c]It should be noted that the $IC_{50}$ value for PatA in this particular assay is ten fold higher than that previously reported. It seems that Jurkat cells appear to vary in their sensitivity to PatA, depending in part on the number of passages they have undergone. All $IC_{50}$ values listed in this table were determined using the same population of Jurkat T cells.

As provided herein, pharmaceutically acceptable salts of Formula I where they can be formed are described. Pharmaceutically acceptable salts may be formed from Formula B compounds and a pharmaceutically acceptable organic or inorganic acid including, but not limited to hydrochloric acid, sulfuric acid, phosphoric acid, acetic acid, maleic acid, fumaric acid, toluenesulfonic acid, benzoic acid, succinic acid and the like. Such salts may be formed during or after the synthesis of the compound of Formula I.

In general, a pharmaceutically acceptable salt as described herein may be administered with a pharmaceutically acceptable carrier to an animal or a human. In order to obtain systemic immune suppression, injection of the compound in a liquid carrier such as saline may prove suitable. For local effects, topical administration in an ointment or cream may have better function. All carriers should be chosen so as not to counteract the desired effects of the compound (immunosuppression or immunostimulation). Additionally, carriers should be chosen to promote the stability of the compound. In both in vitro and in vivo applications, more than one compound of Formula I may be combined with another compound of Formula I or a different compound altogether to achieve multiple effects or a synergistic effect.

Immunosuppressive compounds of Formula I may be used to prevent long-term or short-term transplant rejection. Immunostimulant compounds may be used to counter autoimmune diseases, provide chemotherapy or other cancer treatments and to fight infections, including fungal infections.

The active compounds disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent; such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

Example 1

Synthesis of Biotin-PEO-Macrocycle

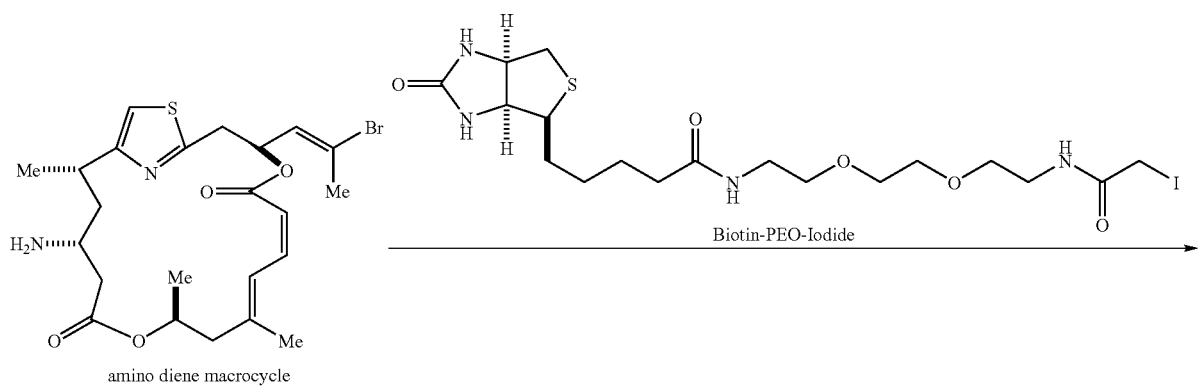

amino diene macrocycle

-continued

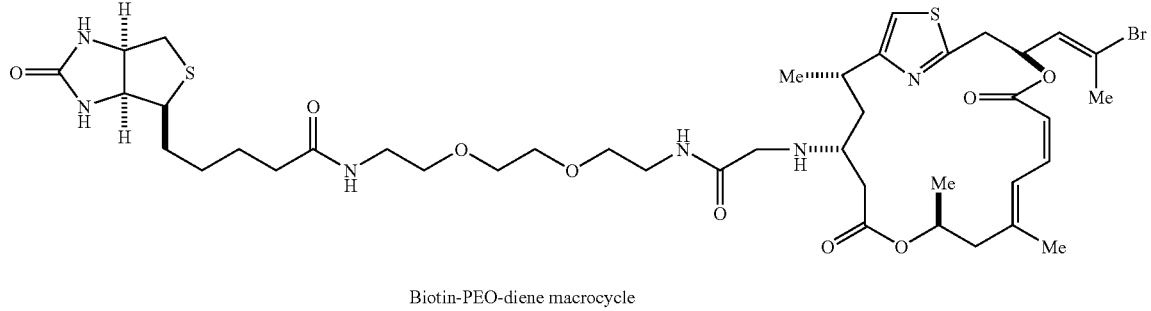

Biotin-PEO-diene macrocycle

To a stirred solution of amino diene macrocycle (6 mg, 0.0117 mmol) in DMF were added biotin-PEO-iodide (6.3 mg, 0.017 mmol) and K$_2$CO$_3$ (3.2 mg, 0.0234 mmol). After 15 h, an additional amount of biotin-PEO-iodide (6.3 mg, 0.0117 mmol) was added. The resulting solution was stirred at 25° C. for 16 h and concentrated in vacuo. Purification of the residue by directly loading on a flash column containing SiO$_2$ and eluting with EtOAc:n-Hex.:Et$_3$N (45:52:8) to CHCl$_3$:MeOH (9:1) gave 8.5 mg (78%) of biotin-PEO-diene macrocycle as a pale yellowish oil: $^1$H-NMR (500 MHz, CDCl$_3$) δ 7.69 (t, J=6 Hz, 1H), 7.01 (d, J=7.2 Hz, 1H), 6.77 (s, 1H), 6.72 (dd, J=6.6, 7.2 Hz, 1H), 6.52 (br s, 1H), 6.01 (dt, J=2, 9.5 Hz), 5.94 (d, J=9.5 Hz, 1H), 5.79 (br s, 2H), 5.42 (d, J=6.6 Hz, 1H), 5.12 (br s, 1H), 5.08-5.04 (m, 1H), 4.51-4.48 (m, 1H), 4.33-4.30 (m, 1H), 3.61-2.84 (m, 15H), 2.45 (s, 3H), 2.33-1.21 (m, 18H), 1.99 (s, 5H), 1.80 (s, 3H); MS (ESI) m/z 927 [M+H]$^+$.

Example 2

Biotin-PEO-Pateamine A

To a flask charged with Pd$_2$dba$_3$●CHCl$_3$ (1.7 mg, 0.0016 mmol) and triphenyl arsine (4.1 mg, 0.013 mmol) was added 0.1 mL of degassed THF (by several freeze/thaw cycles). The final concentration of this palladium catalyst stock solution was 0.031 M. To a solution of Biotin-PEO-diene macrocycle (7 mg, 0.0075 mmol) and tributylstannyl dimethyl amino diene (9.3 mg, 0.0225 mmol) in 0.1 ml of THF was added 0.024 mL of palladium catalyst. The resulting solution was stirred at 25° C. for 14 h and concentrated in vacuo. Purification of the residue by directly loading on a C18 reverse phase chromatography eluting with H$_2$O:CH$_3$CN:AcOH:Et$_3$N (65:35:3 mmol:1.5 mmol) gave 2.1 mg of biotin-PEO-pateamine A as a pale yellowish oil. The residue was loaded on an amino cartridge pre-equilibrated with MeOH and eluted with MeOH to give 2.1 mg (29%) of biotin-PEO-pateamine A as a pale yellowish oil: $^1$H-NMR (500MHz, benzene-d6) δ 7.78 (br t, 1H), 6.67-6.60 (m, 1H), 6.53 (s, 1H), 6.51 (dd, J=12, 6.5 Hz, 1H), 6.37 (br s, 1H), 6.28 (d, J=16 Hz, 1H), 6.18 (d, J=16 Hz, 1H), 5.66 (br t, 1H), 5.61 (d, J=12 Hz, 1H), 5.46 (d, J=9 Hz, 1H), 5.04-4.98 (m, 1H), 4.80 (br s, 1H), 3.06-2.07 (m, 22H), 2.07 (s, 6H), 1.93-0.78 (m, 12H), 1.84 (s, 3H), 1.75 (s, 3H), 1.66 (s, 3H), 1.51 (s, 3H), 1.31 (d, J=6.5 Hz, 3H), 1.01 (d, J=6.5 Hz, 3H); HRMS (ESI) Calcd for C$_{49}$H$_{75}$N$_7$O$_9$S$_2$ [M+H]: 970.5145 Found: 970.5135

Example 3

Molecular Modeling Details

Molecular mechanics and dynamics calculations were performed using the OFF (Open Force Field) program with CVFF 950 (Consistent Valence Force Field) as implemented in Cerius 4.6 (Accelrys, Inc., San Diego, Calif.). Simulated annealing was carried out for 280.0 ps, over a temperature range of 300-500 K, using the Nosé temperature thermostat, a relaxation time of 0.1 ps, and a time step of 0.001 ps. After each annealing step, the structure was minimized, leading to 100 minimized structures. A dielectric constant of 86.75 was used to simulate bulk solvation in water. A rigid body least squares fit algorithm (as implemented in Cerius 4.6) was used to overlay the 100 structures obtained from the simulated annealing and the 16 B3LYP optimized structures. The carbons belonging to the triene region were the only atoms used in the least squares fit. After all molecules were overlayed, a visual inspection of the 24 structures within 3 kcal/mol of the lowest energy structure was used to extract 13 unique conformations of the flexible ring portion of the molecule. Full geometry optimizations (gas phase) and frequency calculations were performed for the 13 unique conformations using Density Functional Theory (DFT) with the Becke three parameter hybrid exchange functional and the Lee-Yang-Parr correlation functional (B3LYP) as implemented in the Gaussian 98 suite of programs. Parr, R. G.; Yang, W. Density-functional theory of atoms and molecules Oxford Univeristy Press, Oxford, 1989; Becke, A. D.; Phys. Rev. A. 1988, 38, 3098; Becke, A. D. J. Chem. Phys. 1993, 98, 1372; Becke, A. D. J. Chem. Phys. 1993, 98, 5648; Lee, C., et al., Physical Review B 1988, 37, 785; Gaussian 98 (Rev. A.9), Frisch, M. J.; Trucks, G. W.; et al.; Gaussian, Inc., Pittsburgh Pa., 1998. A double-ζ quality basis set was used to describe C, N, O, and H (6-31 G) and a double-ζ quality basis set with a polarization function was used to describe S (6-31 G*). Hehre, W. J., et al., J. Chem. Phys. 1982, 77, 3654.

Example 4

Trichloroethyl ester 5

To a stirred solution of 6-oxoheptanoic acid (2.0 g, 12.58 mmol) in benzene (40 mL) was added trichloroethanol (1.08 mL, 11.32 mmol) and $SOCl_2$ (1.1 mL, 15.1 mmol). The solution was refluxed for 8 h and then evaporated and diluted with 30 mL of EtOAc. The layers were separated and the aqueous layer was extracted with EtOAc. The combined organic layers were washed with brine, dried over $MgSO_4$ and concentrated in vacuo. Purification of the residue by flash column chromatography on $SiO_2$ eluting with EtOAc:hexanes (20:80) gave 2.1 g (61%) of ester 5 as a light yellow oil: H NMR (300 MHz, $CDCl_3$) δ 4.71 (s, 2H), 2.46-2.42 (m, 4H), 2.11 (s, 3H), 1.65-1.62 (m, 4H); C NMR (75 MHz, $CDCl_3$) δ 208.4, 171.8, 95.6, 74.1, 43.2, 33.8, 30.1, 24.3, 23.2; IR (neat) 2956, 1762, 1720 $cm^{-1}$.

Example 5

α-Bromoketo Ester 6

To a cooled (0° C.), stirred solution of 6-oxoheptanoic ester (1.00 g, 3.62 mmol) in $CHCl_3$ (20 mL) was slowly added bromine (0.20 mL, 3.98 mmol) in $CCl_4$ over a 1 h period and the solution was stirred at 0° C. for 3 h. The reaction mixture was diluted with 30 mL of $CH_2Cl_2$. The organic layer was washed with satd. aqueous $NaHCO_3$ solution, brine, and then dried over $MgSO_4$ and concentrated in vacuo. Rapid purification of the residue by flash column chromatography on $SiO_2$ eluting with EtOAc:hexanes (10:90) gave 465 mg (36%) of α-bromoester 6 as a yellow oil: H NMR (300 MHz, $CDCl_3$) δ 4.78 (s, 2H), 3.92 (s, 2H), 2.79-2.72 (m, 2H), 2.59-2.48 (m, 2H), 1.81-1.71 (m, 4H)); C NMR (75 MHz, $CDCl_3$) δ 201.7, 171.7, 95.2, 74.1, 39.4, 34.4, 33.8, 24.2, 23.2; IR (neat) 2934, 1753, 1710 $cm^{-1}$; HRMS (ESI) Calcd for $C_9H_{12}BrCl_3O_3$ [M+H]: 376.8903 Found: 376.8901. Schreiber, S. L.; Hung, D. T.; Jamison, T. F. Chem. Biol. 1996, 3, 623-639.

Example 6

Thiazole 9

To a cooled (−5° C.), stirred solution of α-bromoketo ester 6 (354 mg, 1.0 mmol) in $CH_2Cl_2$ (20 mL) was added 2,6-lutidine (0.232 mL, 2.0 mmol) and thioamide 7 (380 mg, 1.0 mmol). The solution was stirred at 25° C. for 12 h and then diluted with 30 mL of $CH_2Cl_2$. The organic layer was washed with brine, dried over $MgSO_4$ and concentrated in vacuo. Rapid purification of the residue by flash column chromatography on $SiO_2$ eluting with EtOAc:hexanes (20:80) gave 528 mg of the intermediate thiazoline 8 as a colorless oil and as a mixture of diastereomers which was used directly in the next step. Some spectral data is provided: H NMR (300 MHz, $CDCl_3$) δ 5.91 (dt, J=1.8, 9 Hz, 1H), 4.82-4.77 (m, 1H), 4.77 (s, 2H), 3.29 (s, 2H), 2.91-2.81 (m, 2H), 2.72 (ddd, J=7.2, 8.7, 14.1, 1H), 2.53 (t, J=7.5 Hz, 2H), 2.29 (s, 2H), 1.89 (t, J=9.3 Hz, 2H), 1.78 (t, J=7.2 Hz, 2H), 1.63-1.48 (m, 4H); C NMR (75 MHz, $CDCl_3$) δ 172.1, 134.9, 108.5, 74.1, 68.9, 68.6, 43.6, 43.5, 43.4, 43.2, 40.9, 34.1, 25.2, 24.7, 23.7, 18.3. 18.1, 12.5. To a cooled (0° C.), stirred solution of thiazoline (528 mg, 0.807 mmol) in $CH_2Cl_2$ (10 mL) was added Hünig's base (1.26 mL, 7.26 mmol), pyridine (200 μL, 2.42 mmol) and TFAA (341 μL, 2.42 mmol) and the solution was stirred at 25° C. for 3 h and then diluted with 30 mL of $CH_2Cl_2$. The organic layer was washed with satd. aqueous $NaHCO_3$, brine, dried over $MgSO_4$ and concentrated in vacuo. Purification of the residue by flash column chromatography on $SiO_2$ eluting with EtOAc:hexanes (20:80) gave 405 mg (80%) of thiazole 9 as a yellow oil: H NMR (300 MHz, $CDCl_3$) δ 6.78 (s, 1H), 5.89 (dd, J=0.6, 8.7 Hz, 1H), 4.80 (dt, J=6.0, 9.0 Hz, 1H), 4.76 (s, 2H), 3.25 (dd, J=6.3, 14.1 Hz, 1H), 3.13 (dd, J=6.3, 14.1 Hz, 1H), 2.80-2.75 (m, 2H), 2.54-2.50 (m, 2H), 2.11 (s, 3H), 1.85-1.72 (m, 4H), 1.04 (s, 21H); C NMR (75 MHz, $CDCl_3$) δ 172.1, 165.4, 156.6, 135.1, 121.5, 113.4, 95.2, 74.1, 70.3, 42.2, 33.9, 31.3, 28.8, 24.5, 24.2, 18.2, 12.5; HRMS (ESI) Calcd for $C_{24}H_{40}BrCl_3NO_3SSi$ [M+H]: 634.0717 Found: 634.0748.

Example 7

Thiazole Enyne 12

To a cooled (−20° C.), stirred solution of thiazole 8 (53 mg, 3.62 mmol) in THF (1.0 mL) was added 0.20 mL of 1M TBAF (0.20 mmol) buffered with 20 mol % AcOH and the solution was stirred at −20° C. for 3 h. The reaction mixture was diluted with 10 mL of $CH_2Cl_2$. The organic layer was washed with satd. aq. $NaHCO_3$, brine, dried over $MgSO_4$ and concentrated in vacuo. Crude purification of the residue by flash column chromatography on $SiO_2$ eluting with EtOAc:hexanes (20:80→50:50) gave 38 mg of alcohol 10 as a light yellow oil which was used directly in the next step. To a solution of DIAD (0.032 mL, 0.167 mmol) in THF (0.5 mL) was added $PPh_3$ (35 mg, 0.1336 mmol) as a solid and the solution was stirred at ambient temperature for 30 min. The resulting heterogeneous mixture was cooled (−20° C.) and the solution of acid (30 mg, 0.0935 mmol) in THF (0.2 mL) was added. After 20 min, a solution of alcohol (32 mg, 0.0668 mmol) in THF (0.2 mL) was added and stirring was continued for 1 h. The reaction was quenched by addition of 2 mL pH 7 buffer followed by warming to 25° C. and diluting with 20 mL of EtOAc. The layers were separated and the aqueous layer was extracted with EtOAc. The combined organic layers were washed with brine, dried over $Na_2SO_4$ and concentrated in vacuo. Purification of the residue by flash column chromatography on $SiO_2$ eluting with EtOAc:hexanes (10:90) gave 37 mg (71%) of thiazole enyne 12 as a light yellow oil: $^1$H NMR (300 MHz, $CDCl_3$) δ 6.77 (s, 1H), 5.87 (dd, J=1.2, 9.6 Hz, 1H), 5.79-5.72 (m, 1H), 5.38 (d, J=1.2 Hz, 1H), 4.71 (s, 2H), 4.13-4.07 (m, 1H), 3.36 (dd, J=6.9, 14.7 Hz, 1H), 3.24 (dd, J=6.9, 14.7 Hz, 1H), 2.74 (t, J=6.9 Hz, 1H), 2.48 (t, J=6.9 Hz, 2H), 2.39 (dd, J=5.4, 14.7 Hz, 1H), 2.23 (dd, J=5.4, 14.7 Hz, 1H), 2.26 (d, J=1.2 Hz, 1H), 1.99 (d, J=1.5 Hz, 3H), 1.77-1.69 (m, 4H), 1.24-1.22 (m, 2H), 1.11 (d, J=6.3 Hz, 3H), 1.03 (s, 21H); HRMS (ESI) Calcd for $C_{33}H_{50}BrCl_3NO_5SSi$ [M+H]: 784.1428 Found: 784.1434.

Example 8

Alcohol 13

To a stirred solution of silylether (30 mg, 0.038 mmol) in THF (0.5 mL) was added 20 mol % AcOH/TBAF (0.095 mL, 0.095 mmol). The resulting solution was stirred at 25° C. for 12 h. The reaction mixture was diluted with 10 mL of $CH_2Cl_2$. The combined organic layers were washed with satd. aqueous $NaHCO_3$, brine, dried over $MgSO_4$ and concentrated in vacuo. Purification of the residue by flash column chromatography on $SiO_2$ eluting with EtOAc:hexanes (50:50) gave 18 mg (75%) of alcohol 13 as a pale yellow oil: H NMR (500 MHz, $CDCl_3$) δ 6.84 (s, 1H), 5.92 (dd, J=1.2, 6.9 Hz, 1H), 5.86-5.79 (m, 1H), 5.48 (s, 1H), 4.77 (s, 2H), 4.07-4.01 (m, 1H), 3.43 (dd, J=6.9, 14.7 Hz, 1H), 3.29 (dd, J=6.9, 14.7 Hz, 1H), 2.81 (t, J=6.6 Hz, 2H), 2.54 (t, J=6.9 Hz, 1H), 2.32 (d, J=1.5 Hz, 3H), 2.07 (d, J=1.2 Hz, 3H), 1.80-1.76 (m, 4H), 1.26 (d, J=6.3 Hz, 3H); C NMR (125 MHz, $CDCl_3$) δ 172.1, 171.4, 163.7, 158.5, 156.9, 153.2, 128.6, 128.1, 113.8, 105.2, 85.6, 83.7, 74.1, 71.6, 65.9, 48.9, 38.0, 33.9, 31.2, 28.7, 24.5, 23.6, 20.7, 14.4; HRMS (ESI) Calcd for $C_{24}H_{39}BrCl_3NO_5S$ [M+H]: 628.0094 Found: 628.0073.

Example 9

Macrocycle 15

To a stirred solution of alcohol 13 (10 mg, 0.0158 mmol) in THF (0.2 mL) and 1M $NH_4OAc$ (0.2 mL) was added 10% Cd/Pd couple (5.0 mg) The resulting solution was stirred at 25° C. for 2 h. The reaction mixture was diluted with 10 mL of EtOAc and then filtered through a celite pad. The organic layer was washed with brine, dried over $MgSO_4$ and concentrated in vacuo. The crude hydroxy acid 14 was submitted directly to macrocyclization conditions without purification. To a cooled (0° C.) stirred solution of hydroxy acid 14 (8 mg, 0.016 mmol) in THF (0.5 mL) was added $Et_3N$ (13 μL, 0.096 mmol) and 2,4,6-trichlorobenzoyl chloride (12.5 μL, 0.08 mmol). The resulting solution was stirred at 0° C. for 20 min and then added to a solution of DMAP (19.5 mg, 0.16 mmol) in toluene (8 mL) at 25° C. and stirred for 2 h. The reaction mixture was diluted with 10 mL of EtOAc. The organic layer was washed with brine, dried over $MgSO_4$ and concentrated in vacuo. Purification of the residue by flash column chromatography on $SiO_2$ eluting with EtOAc:hexanes (30:70) gave 7.0 mg (92%, 2 steps) of macrocycle 15 as a pale yellow oil: H NMR (300 MHz, $CDCl_3$) δ 6.82 (s, 1H), 6.06 (dd, J=1.2, 9.3 Hz, 1H), 5.93-5.86 (m, 1H), 5.35 (s, 1H), 5.33-5.26 (m, 1H), 3.34 (br d, J=7.5 Hz, 2H), 2.81-2.61 (m, 2H), 2.46-2.39 (m, 1H), 2.43 (d, J=1.5 Hz, 3H), 2.30 (d, J=6.9 Hz, 2H), 1.96 (d, J=1.2 Hz, 3H), 1.90-1.68 (m, 3H), 1.57-1.45 (m, 3H), 1.28 (d, J=6.3 Hz, 3H); HRMS (ESI) Calcd for $C_{22}H_{27}BrCl_3NO_4S$ [M+H]: 480.0844 Found: 480.0760.

Example 10

DMDA PatA (3)

A slurry of $Pd/CaCO_3$ poisoned with Pb (5.0 mg) and macrocycle 15 (5.0 mg, 0.0104 mmol) in 0.3 mL of MeOH was evacuated under water aspirator pressure and purged with $H_2$. After stirring at 25° C. for 12 h under 1 atm of $H_2$, the reaction was filtered through Celite, concentrated in vacuo. Passage through a plug of $SiO_2$ eluting with EtOAc:hexanes (50:50) gave 4.6 mg (92%) of E,Z-macrocycle 16 as a colorless oil: H NMR (300 MHz, $CDCl_3$) δ 7.02 (d, J=11.7 Hz, 1H), 6.72 (s, 1H), 6.71 (dd, J=11.7 Hz, 1H), 6.08 (dt, J=4.5, 16.5 Hz, 1H), 5.97 (dq, J=1.2, 9.6 Hz, 1H), 5.36 (d, J=11.7 Hz, 1H), 5.23-5.12 (m, 1H), 3.27-3.14 (m, 2H), 2.93-2.83 (m, 1H), 2.60 (ddd, J=4.5, 10.5, 1.4 Hz, 1H), 2.53-2.47 (m, 1H), 2.51 (s, 3H), 2.41-2.13 (m, 4H), 1.86 (s, 3H), 1.77-1.61 (m, 2H), 1.44-1.29 (m, 2H), 1.27 (d, J=6.6 Hz, 3H). This material was directly used in the next reaction without further purification. To a flask charged with $Pd_2dba_3$●$CHCl_3$ (1.7 mg, 0.0016 mmol) and triphenyl arsine (4.1 mg, 0.013 mmol) was added 0.1 mL of degassed THF prepared by several freeze/thaw cycles. The final concentration of this palladium catalyst stock solution was ~0.031 M. To a solution of macrocycle 16 (4.0 mg, 0.0083 mmol) and stannane 17 (7.0 mg, 0.0166 mmol) in 0.1 mL of THF was added 0.027 mL (0.000837 mmol, 10 mol %) of palladium catalyst stock solution. The resulting solution was stirred at 25° C. for 2 h and concentrated in vacuo. Purification of the residue by flash column chromatography on $SiO_2$ eluting with EtOAc:hexanes:$Et_3N$ (45:52:8) gave 2.1 mg (49%) of DMDAPatA (3) as a pale yellow oil: H NMR (500 MHz, $C_6D_6$) δ 7.47 (d, J=12.0 Hz, 1H), 6.71 (app dt, J=5.0, 9.0 Hz, 1H), 6.45 (app t, J=11.5 Hz, 1H), 6.32 (d, J=16.0 Hz, 1H), 6.21 (d, J=16.0 Hz, 1H), 6.17 (s, 1H), 5.69 (t, J=7 Hz, 1H), 5.55 (d, J=11.5 Hz, 1H), 5.49 (d, J=9.0 Hz, 1H), 5.19-5.11 (m, 1H), 3.08-3.01 (m, 2H), 2.91 (d, J=6.5 Hz, 2H), 2.78 (dt, J=4.5, 14.0 Hz, 1H), 2.48-2.42 (m, 1H), 2.33 (ddd, J=4.0, 10.0, 14.5 Hz, 1H), 2.11 (s, 6H), 2.16-2.03 (m, 2H), 1.90 (d, J=1.0 Hz, 3H), 1.71 (2, 3H), 1.64-1.61 (m, 1H), 1.56-1.43 (m, 2H), 1.54 (s, 3H), 0.96-0.81 (m, 2H), 0.95 (d, J=6.5 Hz, 3H); HRMS (ESI) Calcd for $C_{30}H_{43}N_2O_4S$ [M+H]: 527.2944 Found: 527.2927.

Additional derivatives include positioning a label or identifiable tag on DMDA PatA. Such tags may be colorimetric, fluorescent, radioactive, as examples; however, the tags may also be antibodies, fatty acids, amino acids, peptides, and other organic or inorganic compounds capable of being recognized or detected. An example includes a biotin derivative of pateamine A, synthesized as further shown and described herein. Typically a suitable 1,3-dioxin-4-one is selectively brominated to yield α-bromoketone. Subsequent chemistry is similar to that described-herein for DMDA PatA, with a difference that planned macrocyclization via thermolysis of the dioxinone ultimately provides β-keto DMDA PatA that serves as a novel precursor for a labeled derivative, such as a biotin-PatA conjugate, a representative example of which is shown below. In addition, synthesis of a Pateamine A derivative bearing a hydrazone moiety with a terminal alkyne present allows for exploration of "click" chemistry with a number of substituted azides.

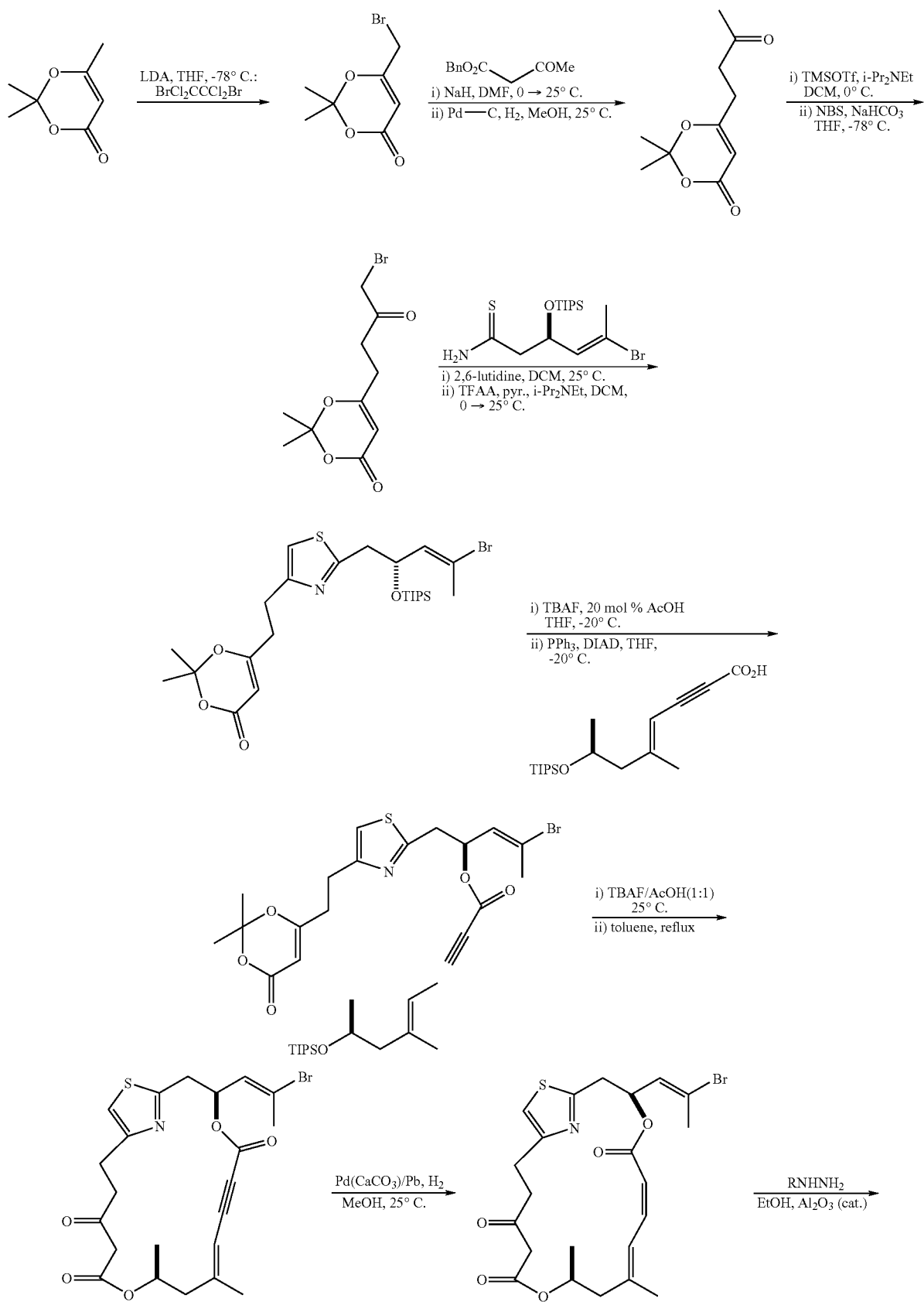

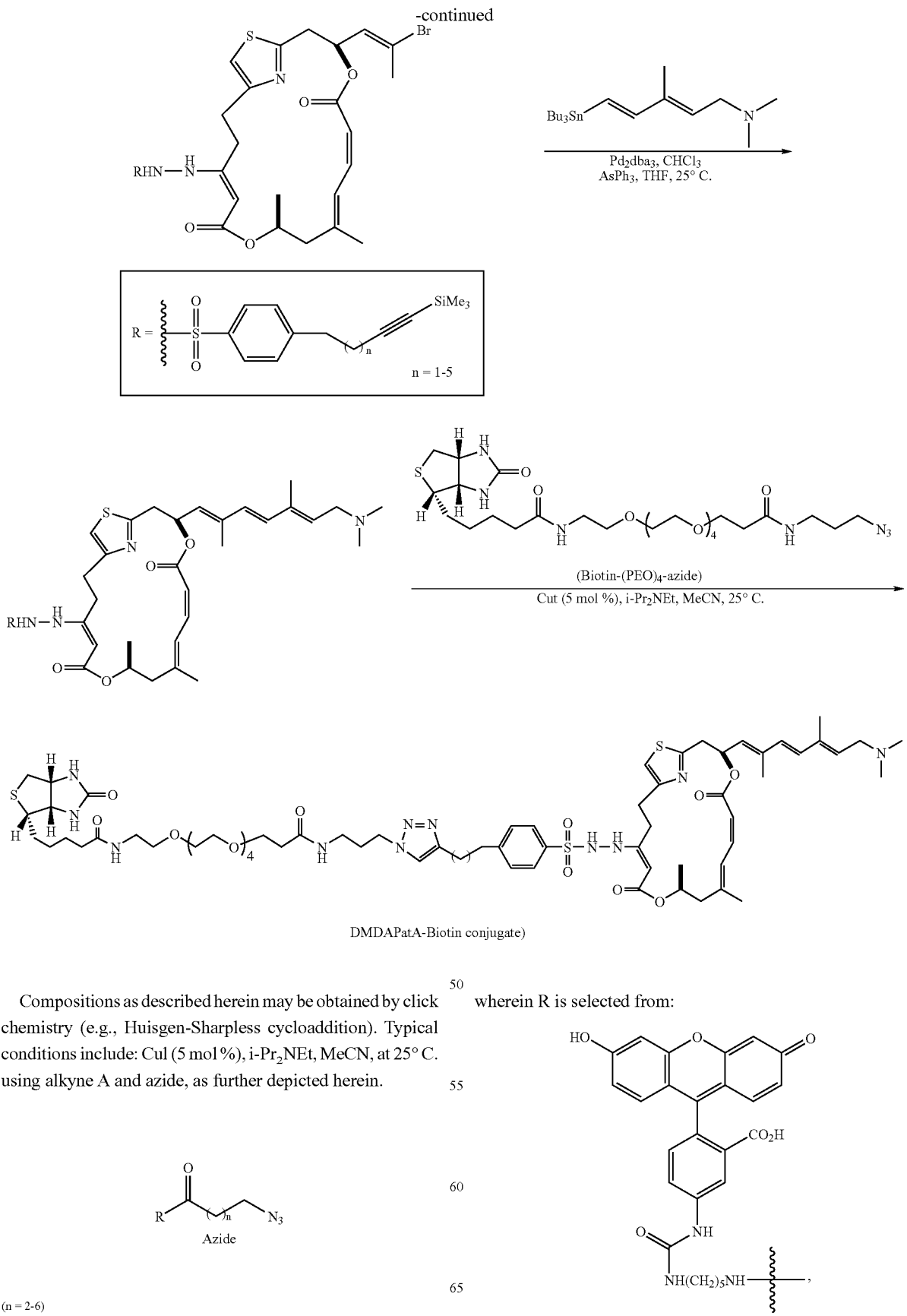
Compositions as described herein may be obtained by click chemistry (e.g., Huisgen-Sharpless cycloaddition). Typical conditions include: CuI (5 mol %), i-Pr₂NEt, MeCN, at 25° C. using alkyne A and azide, as further depicted herein.
wherein R is selected from:

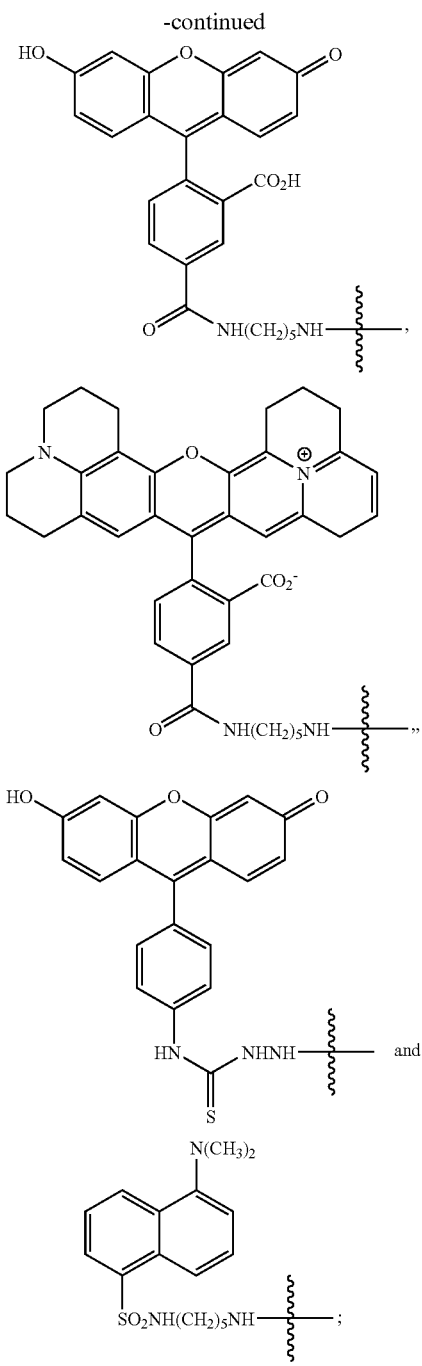

Still other derivatives include dihydro DMDAPatA using a saturated acid as a coupling partner in the Mitsunobu. The desired acid may be accessed through Negishi type cross coupling with known vinyl iodide. The synthesis proceeds as previously described for DMDAPatA.

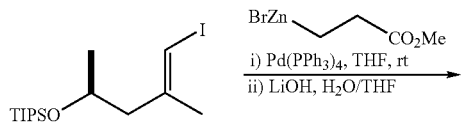

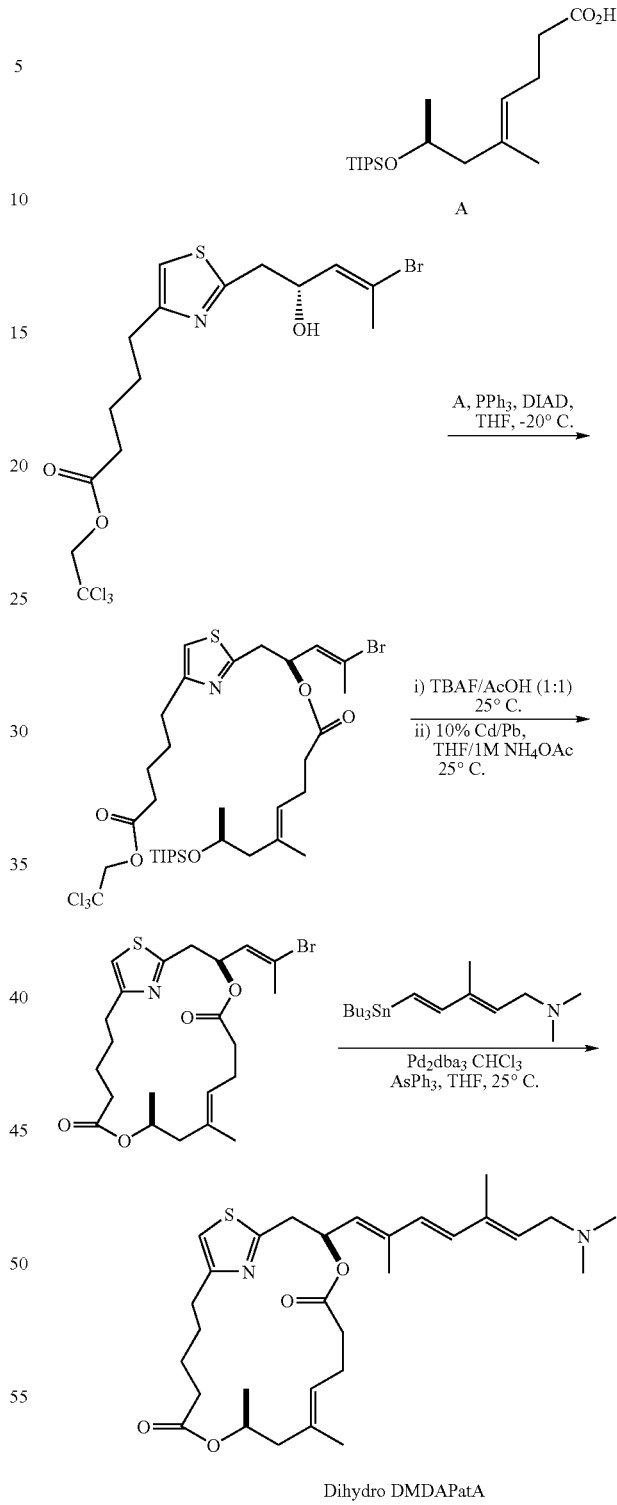

Other suitable compositions include derivatives of DMDAPatA devoid of one methyl group on the trienyl sidechain. The synthesis of such derivatives employ a dienyl-stannane and the same macrocycle as used for the total synthesis of DMDAPatA. A representative example is shown below including all pharmaceutically accepted salts.

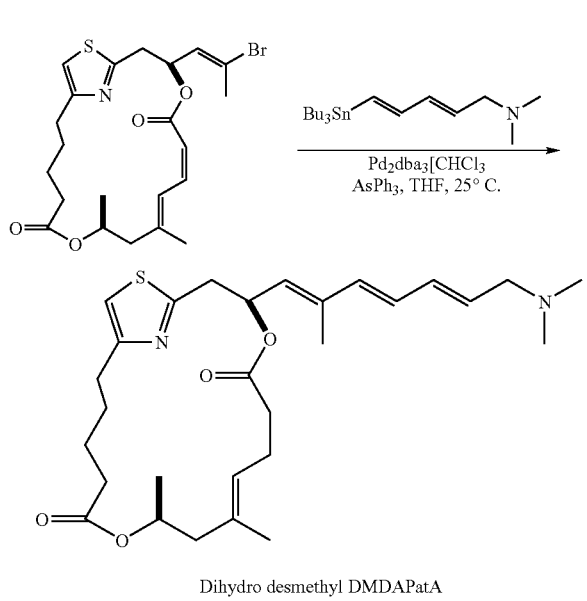

Dihydro desmethyl DMDAPatA

Still other compositions include derivatives of α-amino des-methyl PatA and their pharmaceutically accepted salts that may be prepared as shown herein.

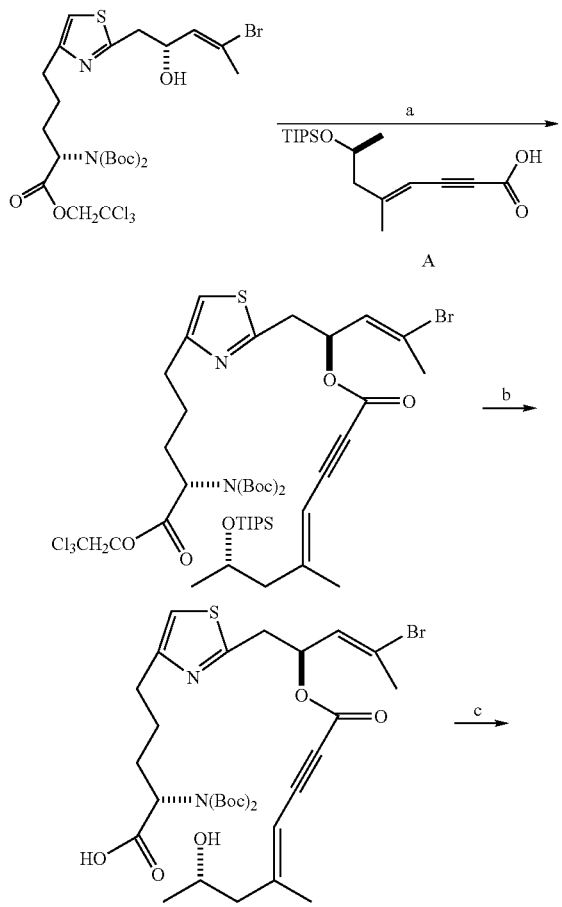

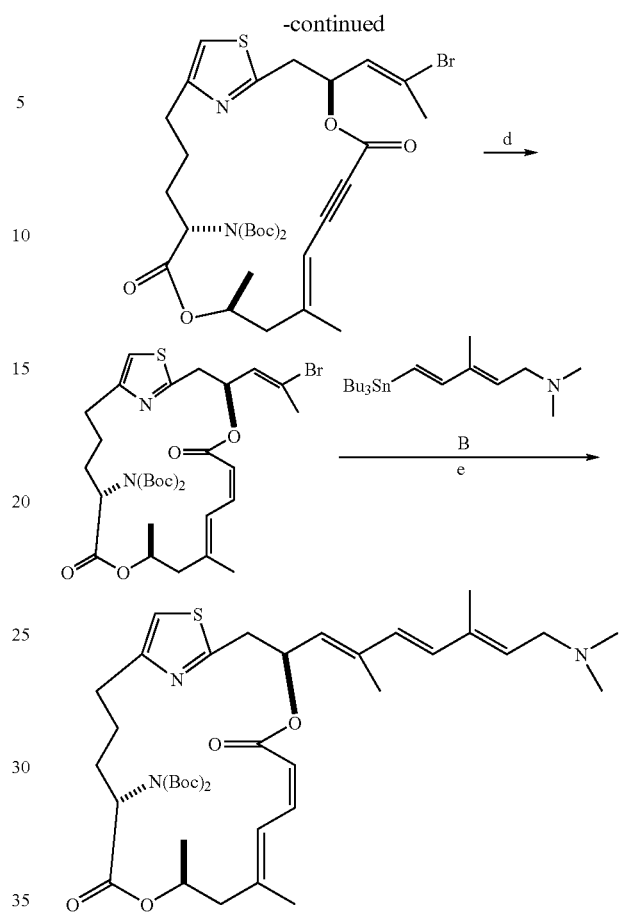

Des-methyl α-amino Pateamine A derivative, 21 a) A, PPh$_3$, DIAD, THF, -20° C., 3 h, 79%;
b) i) TBAF, 20 mol % AcOH, THF, -20° C. to RT, 8 h, 77%; ii) 10% Cd/Pb, THF/1M NH$_4$OAc, 25° C., 14 h 99%;
c) 2,4,6-trichlorobenzoyl chloride, Et$_3$N, DMAP, toluene, THF (0.005 M), 25° C., 2 h, 53%;
d) Pd(CaCO$_3$)/Pb, H$_2$, MeOH 25° C., 12 h, 98%;
e) 10 mol % [Pd$_2$dba$_3$(CHCl$_3$):AsPh$_3$ = 1:8], B, THF, 25° C., 2 h, 49% (based on rec. SM).

Protein synthesis is a fundamental cellular process that is required for decoding the genome to define proteomes of different cell types in a temporally and spatially controlled manner. It is subject to regulation by a multitude of environmental signals during cell proliferation, differentiation and apoptosis. The monumental task of faithfully converting the genetic information in the form of linear sequences of mRNA into the corresponding polypeptide chains is accomplished by sophisticated machinery consisting of both ribonucleic acids and proteins. Among the four major steps of translation in eukaryotes, initiation, elongation, termination and recycling of ribosomes, the rate-determining step is initiation, during which mRNA is recruited to the 43S ribo some particle prior to the formation of an 80S ribosome at the AUG initiation codon. Not surprisingly, translation initiation is the primary site of signal integration for translation control.

At center stage of eukaryotic translation initiation is a eIF4F complex that comprises eIF4E, eIF4G and eIF4A. The eIF4F complex is responsible for recognition of mRNA via 5'-cap, recruitment of mRNA to preloaded 43S complex and possibly subsequent scanning of 5'-UTR to an AUG start codon. The eIF4E factor binds to 5'-m$^7$GpppN (where N is any nucleotide) cap present on a majority of eukaryotic mRNA, recruiting scaffold protein eIF4G, which in turn binds eIF4A and eIF3 that is associated with a 40S ribosomal subunit. The eIF4A component of eIF4F is an RNA-dependent ATPase and an ATP-dependent RNA helicase. Although biochemical function of eIF4A is well defined, its precise role in eukaryotic translation initiation remains unclear.

eIF4A is a founding member of a "DEAD-box" family of ATP-dependent helicases whose activity as an ATPase and RNA helicase have been extensively characterized both biochemically and structurally. eIF4A comprises two distinct domains, with an N-terminal domain serving mainly as a center of ATPase activity and a C-terminus acting primarily for RNA binding. The two domains are connected through a short linker, and residues on both domains are required for function. Enzymatic activities of eIF4A are stimulated by eIF4G, that primarily binds to N-terminal domain of eIF4A. In addition to eIF4G, helicase activity of eIF4A either alone or as part of the eIF4F complex is also stimulated by eIF4B, another protein that participates in eukaryotic translation initiation. Unlike eIF4G, that forms a stable complex with eIF4A, association between eIF4B and eIF4A appears to be transient, as a stable complex between the two has not been observed.

Small chemical ligands have played an important role in facilitating the understanding of translation machinery in prokaryotes. Many prokaryotic translation inhibitors have also become powerful antimicrobial drugs used therapeutically. In contrast, there is a dearth of specific small molecular inhibitors of eukaryotic translation and eukaryotic translation initiation in particular, which is in sharp contrast to the extensive biochemical and genetic insights gained about various components of translation initiation machinery. The accumulation of well-defined biochemical and cellular assays has paved the way to screening for and characterizing small molecular inhibitors of eukaryotic translation.

To elucidate the molecular mechanism of action of a potent antiproliferative and proapoptotic marine natural product, Pateamine A (PatA), eIF4A as described herein is a primary binding protein for PatA. PatA is further found to be a potent inhibitor of translation in mammalian cells. In contrast to its inhibition of eIF4A-dependent translation initiation, PatA was found to stimulate, rather than inhibit, both ATPase and RNA helicase activities of eIF4A. This apparent paradox was resolved upon examination of the integrity of the eIF4F complex and eIF4A-eIF4B association. Upon binding to eIF4A, PatA disrupts eIF4F complex by decreasing an interaction between eIF4A and eIF4G while promoting formation of a stable complex between eIF4A and eIF4B. As a consequence, PatA blocks translation initiation primarily by stalling the 48S complex either in the process of scanning 5'-UTR or by preventing stable binding at an AUG start codon, and causes the formation of stress granules. Indirect immunofluorescence revealed that both eIF4A and eIF4B were colocalized to stress granules (Kedersha and Anderson, 2002), suggesting that eIF4B and possibly eIF4A may be involved in stress granule formation.

Figure 5:
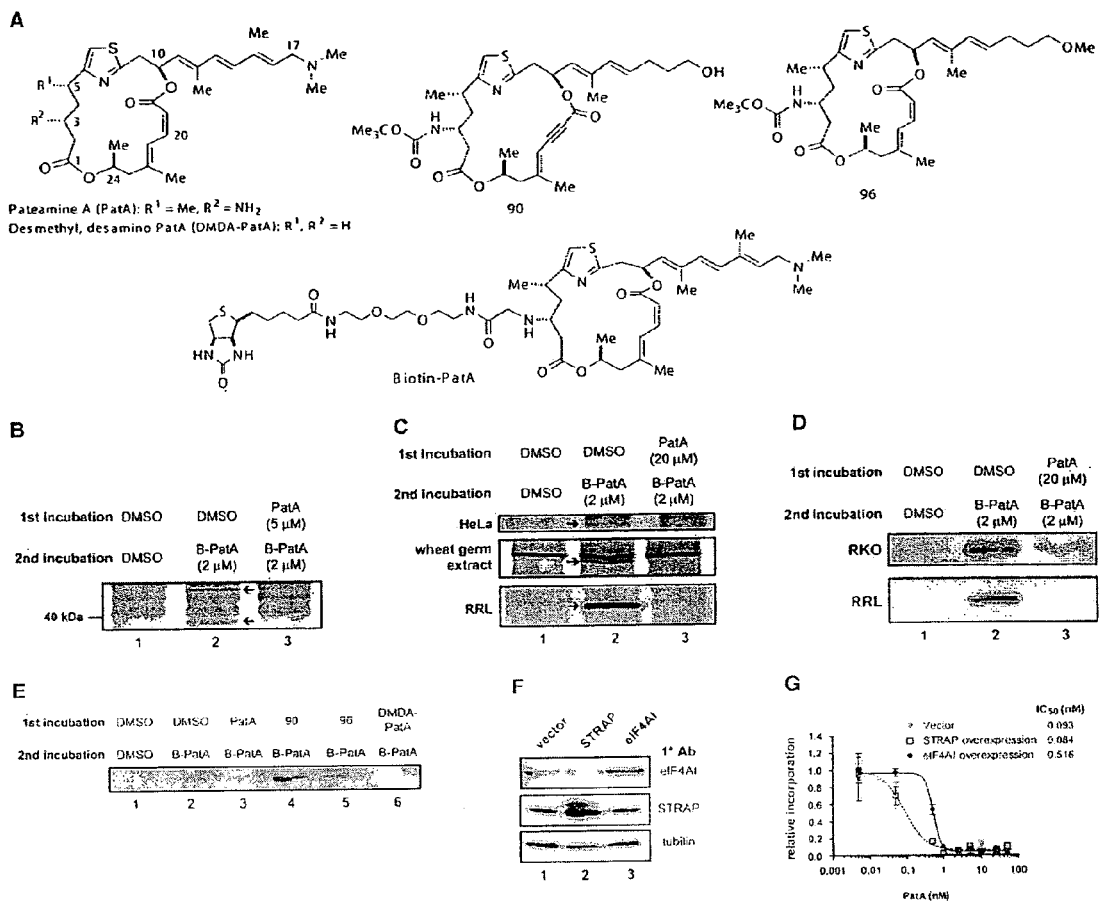
FIGS. 5A-G depict identification of a protein target of PatA, showing (A) representative structures of PatA and analogs, (B) SDS-PAGE analysis of B-PatA bound proteins from RKO cell lysate after silver staining, (C) B-PatA pull-downs performed as in (B) using indicated lysates, (D) confirmation of B-PatA target protein (eIF4A) in RKO and RRL lysates by immunoblotting, (E) B-PatA pull-downs performed as in (B) using RKO cell lysate, including the PatA analogs, 90, 96, and DMDA-PatA, as competitors in the pre-incubation step, (F) target proteins identified by B-Pat (pulldown were individually over-expressed in HeLa cells and (G) cellular proliferation determined by incorporation of [$^3$H]-thymidine), wherein error bars are +/−one standard deviation for quadruplicate readings.
Figure 13:
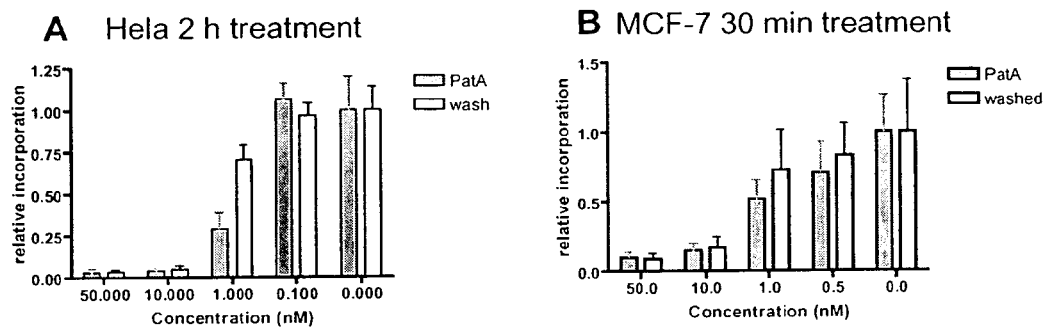
FIGS. 13A-B depict effects of treatment with pateamine A on thymidine incorporation.
Figure 14:
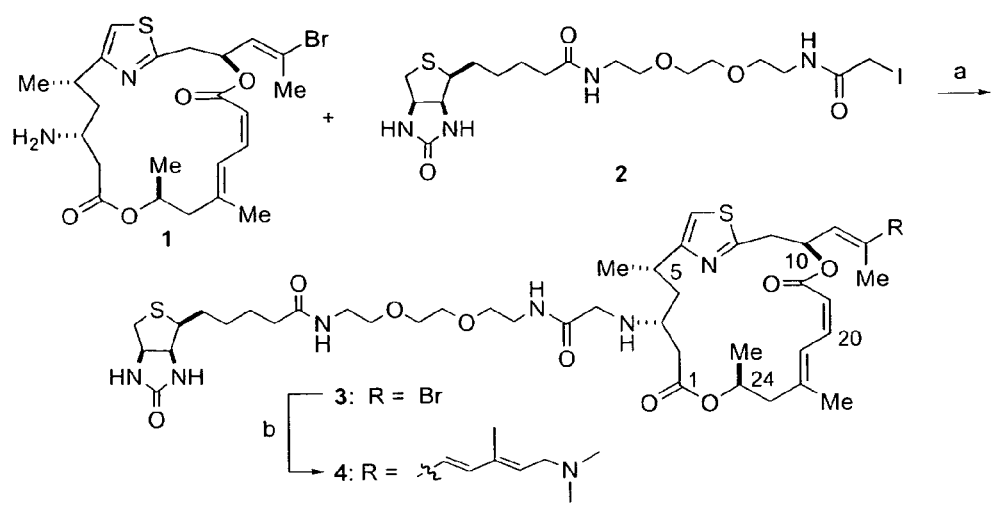
FIG. 14 depicts synthesis of a labeled pateamine A derivative.

Identification of eIF4AI as a PatA Binding Protein and Binding Protein of Suitable Derivatives. PatA (FIG. 5A) was originally found to be cytotoxic in a fast-growing tumor cell line P338 as well as for some fungal species. Subsequently, some of the named inventors found it to be strongly immunosuppressive, blocking a TCR signaling pathway leading to production of interleukin-2. As shown herein PatA has also been found to potently inhibit proliferation of all cancer cell lines with $IC_{50}$ values below 1 nM (FIG. 12) and its effects were irreversible in both HeLa and MCF-7 cells (FIG. 13A-B). As described herein, a number of structural variants of PatA have been synthesized; active and inactive derivatives have been described, two representatives of which are shown in FIG. 5A. Whereas the simplified analog desmethyl, desamino-PatA (a simplified derivative, devoid of the C3-amino and C5-methyl groups; DMDA-PatA) was found to retain most of the activity of PatA, analogs 90 and 96 showed no activity at concentrations up to 100 nM in cell proliferation assays. Furthermore, modifications of a C3 amino group ($R_2$ in FIG. 5A) was tolerated without loss of activity. Thus, a further derivative, as described herein, was used in which a label (e.g., biotin moiety) was linked to PatA through a C3 amino group by total chemical synthesis (FIG. 14). Biotin-PatA (B-PatA) used in proliferation assay with RKO cells provided an $IC_{50}$ of <15 nM, indicating that cellular activity of the parent compound was retained by B-PatA.

B-PatA was then used in conjunction with streptavidin-sepharose in affinity-binding assays with total cell lysates from RKO and other cell lines. Here, at least two putative PatA binding proteins were detected; two discussed further herein had apparent molecular masses of 48 and 38 kDa, respectively (FIG. 5B, Lane 2 vs. 1). Both proteins were effectively competed away by excess free PatA (FIG. 5B, Lane 3), suggesting B-PatA captured such target proteins via interactions similar to PatA. The 48 kDa and the 38 kDa bands were separated by SDS-PAGE and identified by MALDI-TOF mass spectrometry after scaling-up of the binding assay (data not shown). The 48 kDa protein was identified as eIF4AI. The 38 kDa protein was identified as the Serine/Threonine kinase Receptor Associated Protein (STRAP), also known as Upstream of N-Ras Interacting Protein (UN-RIP), which interacts with UNR that is itself implicated in viral internal ribosomal entry, and as an activator of MAP kinase enabling anchorage-independent cell growth.

Binding of eIF4A by B-PatA was reproducibly observed in other cell lysates, including HeLa cells, wheat germ extract and rabbit reticulocyte lysate (RRL), as judged by the molecular mass (FIG. 5C). Binding of STRAP to B-PatA did not appear in all instances (data not shown), likely due to either lower abundance or lack of presence in some lysates. The identity of the 48 kDa protein was confirmed in RKO cell lysate and RRL by Western blot using eIF4A-specific antibodies following the pull-down assay (FIG. 5D). Further demonstration of the specificity of eIF4A binding and its relation to biological activity was observed when the two biologically inactive analogs 90 and 96 were unable to compete with B-PatA for eIF4A binding, whereas active DMDA-PatA analog was competitive, consistent with cellular activities (FIG. 5E).

eIF4A and STRAP were found to perform a role in antiproliferative effects of PatA. Each protein was ectopically overexpressed in HeLa cells and the consequence of overexpression of either protein on the sensitivity of cells to PatA was determined. As shown in FIGS. 5F and G, in comparison with a control (empty vector), overexpression of eIF4AI caused a significant gain in resistance of cells to PatA, with a 5-fold increase in $IC_{50}$ for PatA. Overexpression of STRAP did not alter sensitivity of HeLa cells to PatA. eIF4A is likely a strong mediator of cell proliferation inhibition by PatA.

Figure 6:
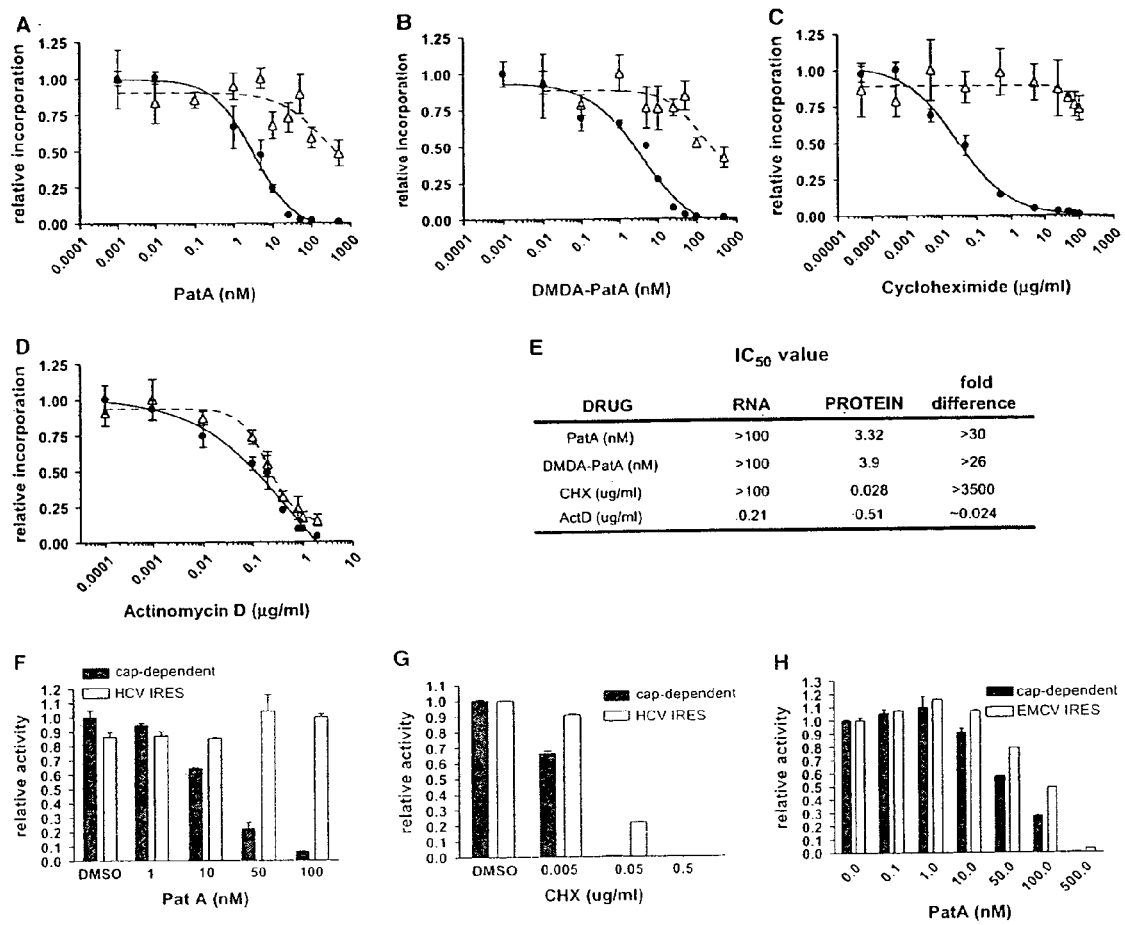
FIGS. 6A-E depict PatA and active analogs as potent inhibitors of protein translation initiation, wherein [$^{35}$S]-methionine and cysteine labeling mix are filled circles and [$^3$H]-uridine are open triangles, (E) IC$_{50}$ values for inhibition.
FIGS. 6F-H depict in vitro protein translation efficiency (solid bars represent cap-dependent [1$^{st}$ cistron] activity and clear bars represent respective IRES [2$^{nd}$ cistron] activity) for (F) cap-dependent vs. HCV IRES-dependent translation under PatA treatment, (G) cap-dependent vs. HCV IRES-dependent translation under CHX treatment, and (H) cap-dependent vs. EMCV IRES-dependent translation under PatA treatment.

PatA and Derivatives Effect Protein Translation. PatA affects protein translation. Such effects of PatA on global protein, and RNA synthesis were examined using [$^{35}$S]-methionine/cysteine and [$^3$H]-uridine labeling respectively, in conditional media and compared with a known protein synthesis inhibitor cycloheximide (CHX) and actinomycin D (ActD), a known inhibitor of transcription. Similar to CHX (FIG. 6C), PatA caused a rapid (1 h treatment) inhibition of protein synthesis with an $IC_{50}$ value of 3.3 nM (FIGS. 6A and E). PatA also exhibited an inhibitory effect on RNA synthesis; however, the difference in $IC_{50}$ values between protein synthesis and RNA synthesis inhibition was greater than 30-fold, which is in stark contrast to the nearly identical $IC_{50}$ values of ActD (FIG. 6D-E). At three hours of treatment with PatA, $IC_{50}$ values for RNA synthesis inhibition approached that of protein synthesis inhibition, likely reflecting a signaling response to loss of translation (data not shown). From a ratio of $IC_{50}$ values in FIG. 6E, PatA lies between CHX and ActD (due primarily to a much lower $IC_{50}$ of CHX for protein synthesis inhibition, as shown in FIG. 6E). Similarly DMDA-PatA also inhibited protein synthesis with a secondary effect on RNA synthesis (FIG. 6B), in agreement with its antiproliferative activity and its ability to compete with B-PatA for binding to eIF4AI (FIG. 5E).

All cap-dependent translation initiation requires eIF4A; however, cap-independent translation initiation using internal ribosomal entry sites may or may not require eIF4A, depending on the specific IRES sequence elements. The effect of PatA in RRL using bicistronic reporters was performed, in which a first cistron (Firefly luciferase) was translated through cap-dependent initiation and a second cistron (Renilla luciferase) was initiated through an IRES element. PatA nearly completely inhibited cap-dependent translation at 100 nM with an $IC_{50}$ of approximately 20 nM (FIG. 6F). HCV IRES-mediated (eIF4A-independent) translation was not inhibited at 100 nM of PatA (FIG. 6F). Treatment with CHX, a known elongation inhibitor, resulted in nearly equal inhibition of both cap- and HCV IRES-dependent translation (FIG. 6G). The second reporter tested, which contained the EMCV IRES (eIF4G and eIF4A-dependent) was inhibited nearly equally at both cistrons with $IC_{50}$ values of approximately 88 nM for cap-dependent and 54 nM for EMCV IRES mediated initiation (FIG. 6H).

Figure 7:
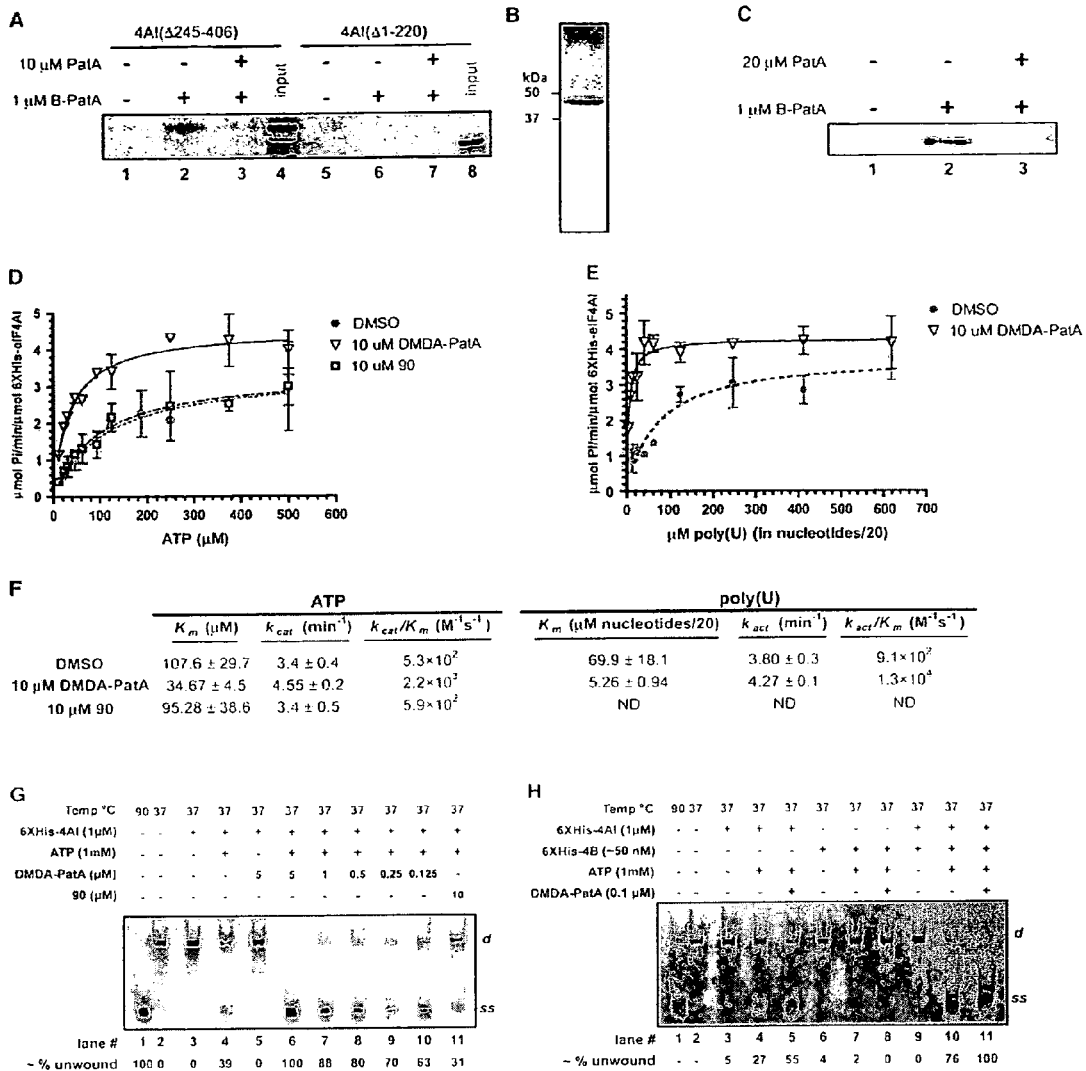
FIGS. 7A-H depict pateamine A modulation of eIF4AI through binding to an N-terminal domain with (A) expressed C-terminal deletion, 4AI(Δ245-406) and N-terminal deletion, 4AI(Δ1-220) mutants, (B) purified 6XHis-eIF4AI, (C) affinity pulldown of purified 6XHis-eIF4AI with detection of target protein by immunoblotting using His tag-specific antibody, (D) ATPase activity of 6XHis-eIF4AI in the presence of indicated analog or DMSO, (E) half-maximal amount of poly (U) RNA for activation of ATPase activity, (F) values for K$_m$ and k$_{cat}$, (G-H) helicase activity of 6XHis-eIF4AI in the presence of DMSO or varying concentrations of DMDA-PatA (G) and in the presence of 6XHis-4B with, or without DMDA-PatA (H)

PatA and Derivatives Stimulate the ATPase and RNA Helicase Activity of eIF4A. eIF4A possesses at least two distinct but coupled enzymatic activities, RNA-dependent ATPase and ATP-dependent RNA helicase activity, residing on both (N- and C-terminal domains, which are joined by a flexible linker region). To determine which domain(s) are bound by PatA, N- and C-terminal deletion mutants of eIF4AI were generated and labeled with [$^{35}$S]-methionine by in vitro transcription/translation and used in a pull-down assay as described in FIG. 5. As shown in FIG. 7A, the N-terminal ATP-binding domain was sufficient for B-PatA binding that was sensitive to competition by free PatA.

Further characterization of the eIF4A-PatA interaction was performed. Recombinant eIF4AI with an N-terminal 6XHis tag was produced and purified from E. coli (FIG. 7B) and its ability to bind to PatA was verified (FIG. 7C). RNA-dependent ATPase activity of recombinant eIF4AI was determined in the presence of DMSO (as a carrier control), DMDA-PatA, or analog 90 under saturating RNA (poly(U)) concentrations. DMDA-PatA marginally increased $k_{cat}$ of the reaction, it caused a significant decrease in $K_m^{ATP}$, leading to an overall increase in $k_{cat}/K_m$ by almost four fold (FIG. 7D). In contrast, the inactive analog 90 had no effect on ATPase activity of eIF4AI. A half-maximal amount of RNA for ATPase activation ($K_m^{RNA}$) was also determined using poly(U) RNA (FIGS. 7E, F). Previous work has demonstrated that $K_m^{RNA}$ accurately represents $K_d$ of dissociation for eIF4A and RNA. Again, $k_{cat}$ was only slightly affected, whereas a significant decrease in $K_m^{RNA}$ was observed. Thus, indicating that PatA stimulates ATPase activity of eIF4A. Because ATPase activity is required for helicase activity, helicase activity for eIF4AI in the presence and absence of DMDA-PatA was determined.

Similar to RNA-dependent ATPase activity, DMDA-PatA dramatically increased the ATP-dependent RNA helicase activity of eIF4AI (FIG. 7G, Lane 6 vs. 4). DMDA-PatA alone did not affect the RNA helicase activity in the absence of ATP (FIG. 7G, Lane 5), affirming that PatA stimulates, rather than inhibits enzymatic activities of eIF4A.

Figure 15:
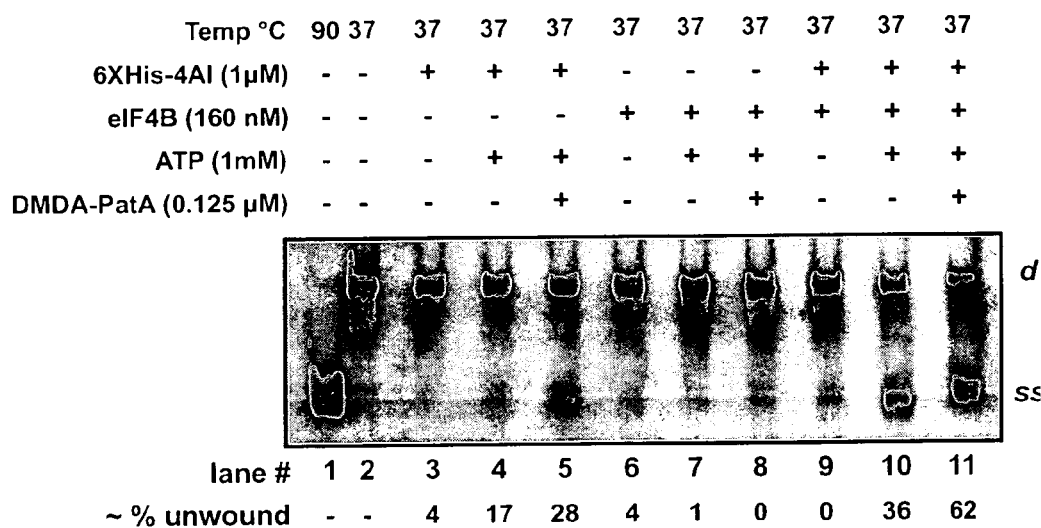
FIG. 15 depicts effect of DMDA-PatA on stimulation of ATP-dependent eIF4A1 helicase activity.

PatA and Derivatives Decrease Association Between eIF4A and eIF4G and Promotes Association Between eIF4A and eIF4B. eIF4A is known to act in concert with several proteins for function in vivo, most notably with eIF4G as part of the eIF4F complex. eIF4A-eIF4G interaction was determined using recombinant His-tagged eIF4AI as bait to capture eIF4G from HeLa lysate in the presence and absence of PatA. As shown in FIG. 8A, stable binding of eIF4A and eIF4G was disrupted in the presence of 100 µM PatA. Because of its ability to increase eIF4A activity and thus its inferred binding, eIF4B was also examined. In contrast to eIF4G, only a small amount of eIF4B was captured by 6XHis-eIF4A in the absence of PatA. However, the presence of PatA led to an increase in amount of eIF4B observed (FIG. 8A, Lane 3). Similar disruption of eIF4A-eIF4G interaction and enhancement of eIF4A-eIF4B interaction was observed with DMDA-PatA in a dose-dependent manner, but not with inactive analog 90 (FIG. 8B). Comparable results were also obtained using Jurkat T cell lysates and RRL (data not shown). Thus there is a PatA-dependent interaction between eIF4A and eEF4B, verified by a Flag-tagged eIF4B overexpressed in 293T cells, which were then treated with 20 nM DMDA-PatA or DMSO for 1 h. In brief, cell lysates were prepared and immunoprecipitation performed using a Flag tag-specific antibody. eIF4A was associated with Flag-eIF4B only in the presence of DMDA-PatA (FIG. 8C, Lanes 4 vs. 5). eIF4G-eIF4A interaction without a requirement for excess protein was determined using m$^7$GTP-Sepharose to capture eIF4F from RRL through its interaction with eIF4E. Under DMDA-PatA treatment, a significantly lower amount of eIF4A was detected compared to DMSO control (FIG. 8D, Lane 1 vs, 2), thus showing a decrease in the eIF4A-eIF4G interaction in the presence of PatA. PatA changes the affinity of eIF4A for its partner proteins, thereby perturbing the eIF4F ternary complex, through weakening of an interaction between eIF4A and eIF4G, and concurrent promotion of an otherwise transient interaction between eIF4A and eIF4B.

eIF4B-stimulated eIF4AI helicase activity in the presence of DMDA-PatA (FIG. 7H). Recombinant eIF4B produced in E. coli (6XHis-4B) was capable of stimulating eIF4AI helicase activity (FIG. 7H, Lane 4 vs. 10). In addition, the presence of DMDA-PatA further stimulated the helicase activity of eIF4A and 4B (FIG. 7H, Lane 10 vs. 11). As eIF4B requires phosphorylation for activity purified eIF4B from RRL was also tested, and produced results similar to the E. coli expressed protein (FIG. 15).

Figure 16:
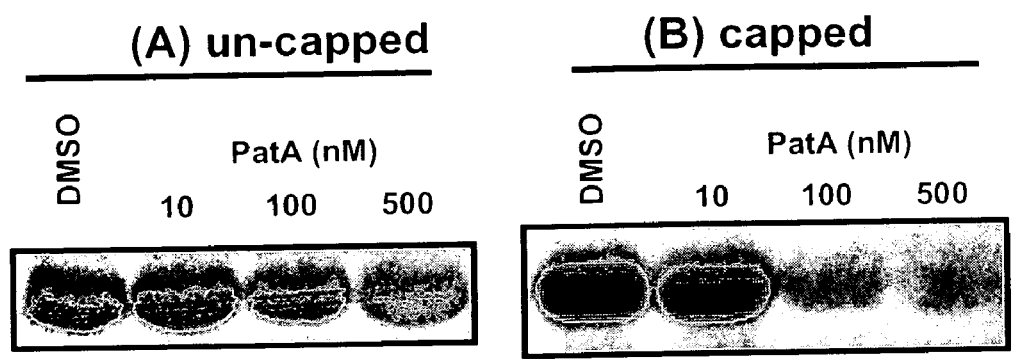
FIGS. 16A-B depict translation sensitivity of capped and uncapped RNA to pateamine A.

Accordingly, as described herein, PatA promotes a complex containing both eIF4A and eIF4B. The effect of PatA on binding of both proteins to radiolabeled β-globin RNA was also determined using UV crosslinking. After incubation of RNA in translation competent RRL treated with DMSO or PatA, samples were exposed to UV radiation. Proteins crosslinked to RNA were identified by molecular weight following SDS-PAGE and autoradiography. In the presence of PatA, the amount of RNA crosslinked to eIF4A was not appreciably changed (FIG. 16). However, the amount of RNA crosslinked to eIF4B was significantly increased; indicating that although PatA bound directly to eIF4A, its presence in RRL adversely affected status of eIF4B.

PatA and Derivatives Stall the Translation Initiation Complexes. Using radiolabeled RNA templates, sucrose gradient analysis was used distinguish between 48S and 80S complexes. With inclusion of GMPPNP (a non-hydrolyzable GTP analog) that inhibits 60S subunit joining, a build-up of 48S complexes should occur. With CHX that blocks the elongation process, an intact 80S complex at the start codon should remain. The analysis involved comparison of PatA treatment alone vs. DMSO, co-treatment of either GMPPNP and PatA vs. GMPPNP alone, or CHX and PatA vs. CHX alone.

Figure 9:
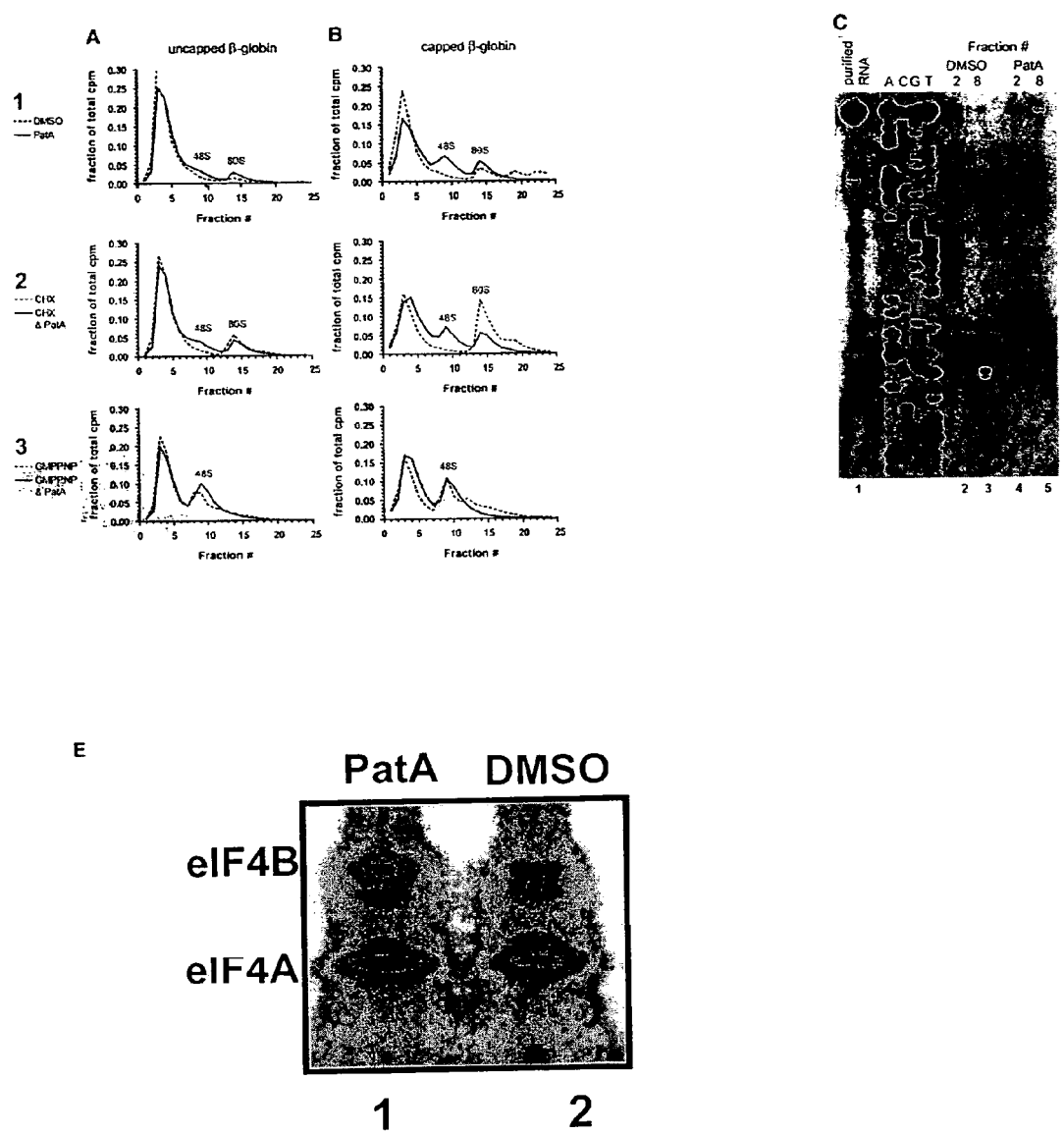
FIGS. 9A-C and 9E depict pateamine A inhibition of translation initiation after 48S complex formation, showing (A-C) 48S and 80S particles bound to radiolabeled uncapped (A), capped β-globin (B), or EMCV IRES RNA (C) in the presence of PatA alone, or in combination with CHX, or GMP-PNP, (E) toeprinting profile for GMPPNP and DMSO treatment, or GMPPNP and PatA treatment, and (D) sequence as determined from sequencing ladder.
Figure 17:
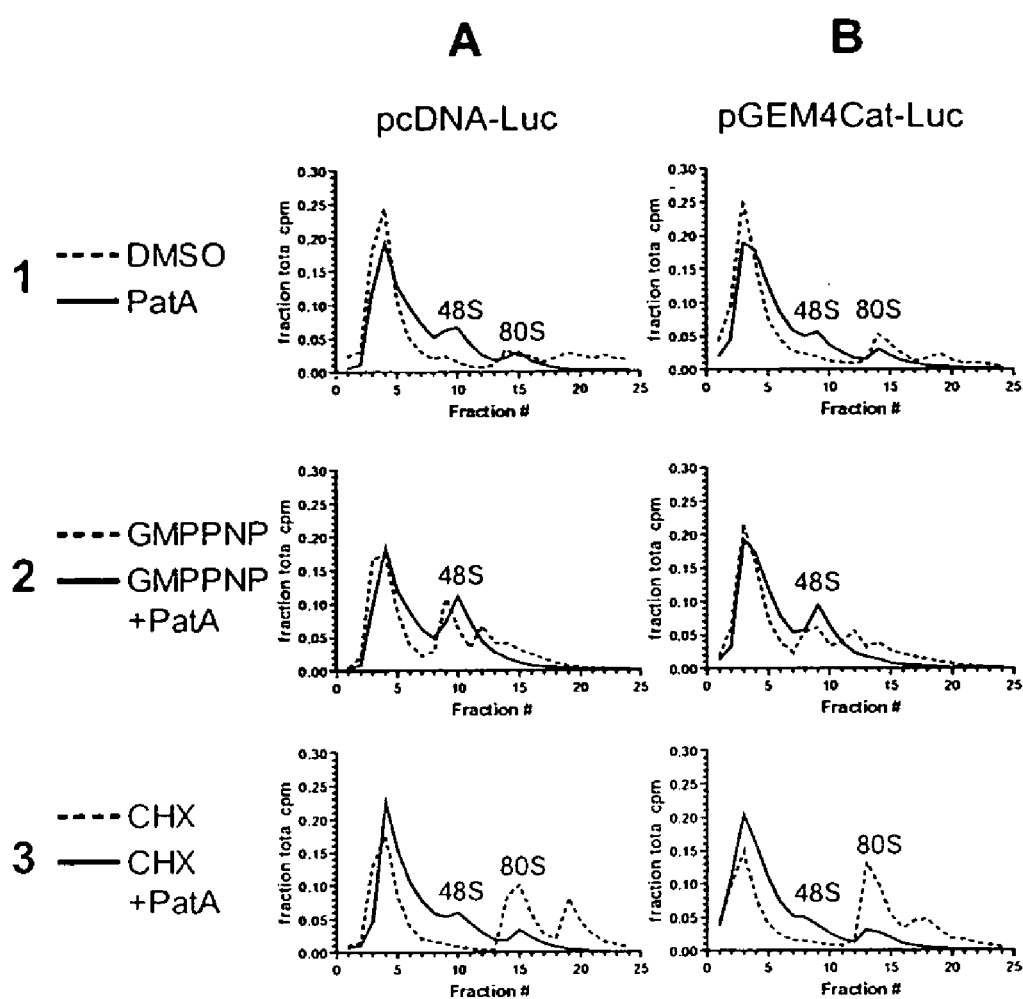
FIG. 17 depicts effects of pateamine A treatment on EMCV IRES RNA (1) alone, or in combination with (3) cyclohexamine or (2) GMPPNP with RINA from vectors pcDNA-Luc (A) and pGEN4Cat-Luc (B)

Two forms of β-globin RNA were the first RNA species analyzed, capped and uncapped, to identify cap-dependent effects of PatA (FIG. 9, A vs. B). Using [$^{35}$S]-methionine labelling, higher levels of translation were achieved with capped RNA, yet translation from capped RNA was much more sensitive to inhibition by PatA than uncapped RNA (FIG. 17). In FIG. 9A, Rows 1 and 2 (A1, A2), only modest differences were observed between the two indicated treatments for uncapped β-globin RNA. Comparing DMSO vs. PatA (FIG. 9, A1) slightly more 48S and 80S complexes were formed, although levels were very close to background. In FIG. 9, A2, results were similar to A1, in that a modest build-up of 48S complexes over CHX alone was observed. In FIG. 9, A3, (co-treatment of PatA and GMPPNP vs. GMPPNP alone) no significant differences were observed. When RNA contained the m$^7$GpppN cap structure, the presence of PatA led to significantly greater amounts of 48S complexes in both the presence of PatA alone (FIG. 9, B1), and in co-treatment with PatA plus CHX (FIG. 9, B2). In FIG. 9, B3, similar to FIG. 9, A3, the presence of PatA with GMPPNP was not significantly different than treatment with GMPPNP alone.

EMCV IRES, which does not rely on the cap structure for assembly of the ribosome, but does require eIF4A and eIF4G, was used to demonstrate 48S build-up under PatA treatment (FIG. 9, C1 and C2). However, for this RNA, only small amounts of 80S were detected compared to the β-globin RNAs. Again, as for both β-globin RNAs, no significant changes were observed between GMPPNP alone and in co-treatment with PatA (FIG. 9, C2).

Two additional RNA templates were included in the sucrose gradient centrifugation analysis, both having UTR sequences distinct from RNAs already described, and distinct from each other. Analysis of these RNA species was identical to that described for β-globin and EMCV RNA. Here (FIG. 17), the presence of PatA produced qualitatively similar profiles to those described for capped β-globin RNA in that PatA alone, or in co-treatment with CHX produced accumulation of 48S complexes in comparison to control. Treatments with CHX or GMPPNP alone did not provide single 48S or 80S peaks, as expected, and may reflect the artificial nature of these reporter plasmid templates. For GMPPNP alone, multiple peaks were observed, which may reflect multiple stalled 48S complexes on the RNAs, and double peaks were observed under CHX alone, possibly indicating multiple stalled 80S complexes. Co-treatment with PatA provided single 48S peaks. Thus, PatA treatment is consistent with that described in FIG. 9; PatA produced accumulation of 48S complexes with varying amounts of 80S complexes observed. Global analysis of all RNA species suggests PatA blocks or inhibits progression of 48S complexes to 80S status.

In FIG. 9 and FIG. 17, co-treatments of PatA with GMPPNP produced profiles similar to GMPPNP alone, which would suggest that PatA inhibition occurs at a step after stable binding of 43S over a AUG start codon. However, sucrose gradient analysis cannot distinguish between species with 43S bound at different locations of the RNA. To understand the 48S complexes accumulation in the presence of GMPPNP alone and in co-treatment with PatA, toeprinting experiments were performed using β-globin RNA under identical conditions as described for FIG. 9, B3. The presence of GMPPNP led to the protection of nucleotides up to position +17, similar to that previously described (FIG. 9E). Treatment with a combination of GMPPNP and PatA led to extension of the entire RNA template, suggesting the 48S complex stalled by PatA is an earlier intermediate than that resulting from the GMPPNP blockage. Under conditions of FIG. 9, B2 (PatA and CHX co-treatment) full-length transcripts were observed by toeprinting, however data was more variable than for co-treatment with GMPPNP (data not shown). As toeprinting relies on processivity of reverse transcriptase along a template, less stably bound 43S complexes should potentially be displaced during extension. The precise location of the ribosome on mRNA remains unclear. The 43S may be stalled at the 5'-cap prior to scanning, in a position between the 5'-cap and the start AUG codon, or it may have failed to stably bind to the AUG sequence.

PatA and Derivatives Deplete Polysomes and Cause Redistribution of eIF4 Factors. Cellular polysome profiles of lysates prepared from 293T cells treated with DMSO, CHX, PatA or analog 90 were determined by sucrose gradient centrifugation, followed by determination of absorption at 254 nm. Here, absorption at 254 nm identifies all RNA, which is dominated by ribosomal RNA. Thus, direct observations of all ribosomal particles may be made, but cannot distinguish between bound mRNA and free ribosomal species. Yet, polysomes can clearly be identified, as observed in DMSO-treated cells (FIG. 10A). Treatment with PatA led to the depletion of polysomes and a significant increase in a peak consistent with 80S particles (FIG. 10B) in contrast to treatment with CHX, which did not perturb the sucrose gradient profile, as CHX inhibits translation elongation and does not allow stalled 80S complexes to proceed to termination (FIG. 10C). The inactive analog 90 gave a similar profile as DMSO (FIG. 10D). Transcription initiation process is inhibited by PatA in vivo, as elongating 80S complexes (polysomes) appear to complete their cycle and become free 80S complexes.

Because PatA appears to be affecting the initiation process, the distribution of initiation factors in HeLa cells was examined by sucrose gradient centrifugation after PatA treatment. Compared to DMSO treatment, PatA caused redistribution of subpopulations of eIF4A, B, E and G to the higher molecular mass fractions around the apparent 80S peak, which did not occur for a control protein tubulin (FIG. 10E vs. F). Furthermore, the apparent 80S coincided with congregation of S6 small ribosomal subunit and L28 subunit from large 60S ribosomal particle (data not shown). For eIF4A and eIF4G, the peak values of proteins detected did not coincide with each under both treatment conditions, and it also is noteworthy that significant amounts of eIF4B, as well as eIF4A, E and G remained in low-density fractions (FIG. 10F).

Figure 11:
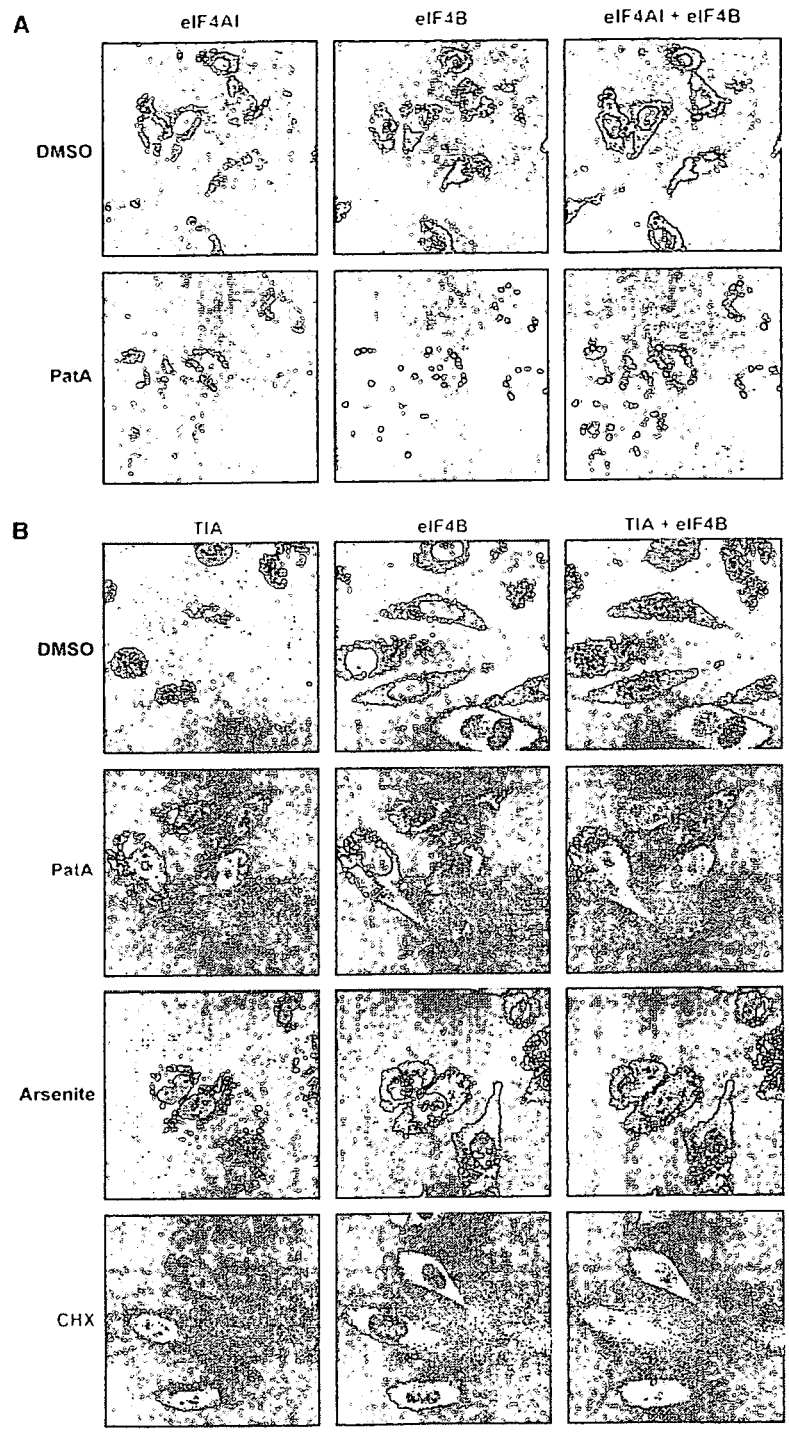
FIGS. 11A-B depict induction of stress granules by PatA showing (A) 10 nM PatA treatment or DMSO and (B) 25 nM PatA, 0.5 mM arsenite, 100 μg/ml CHX.
Figure 18:
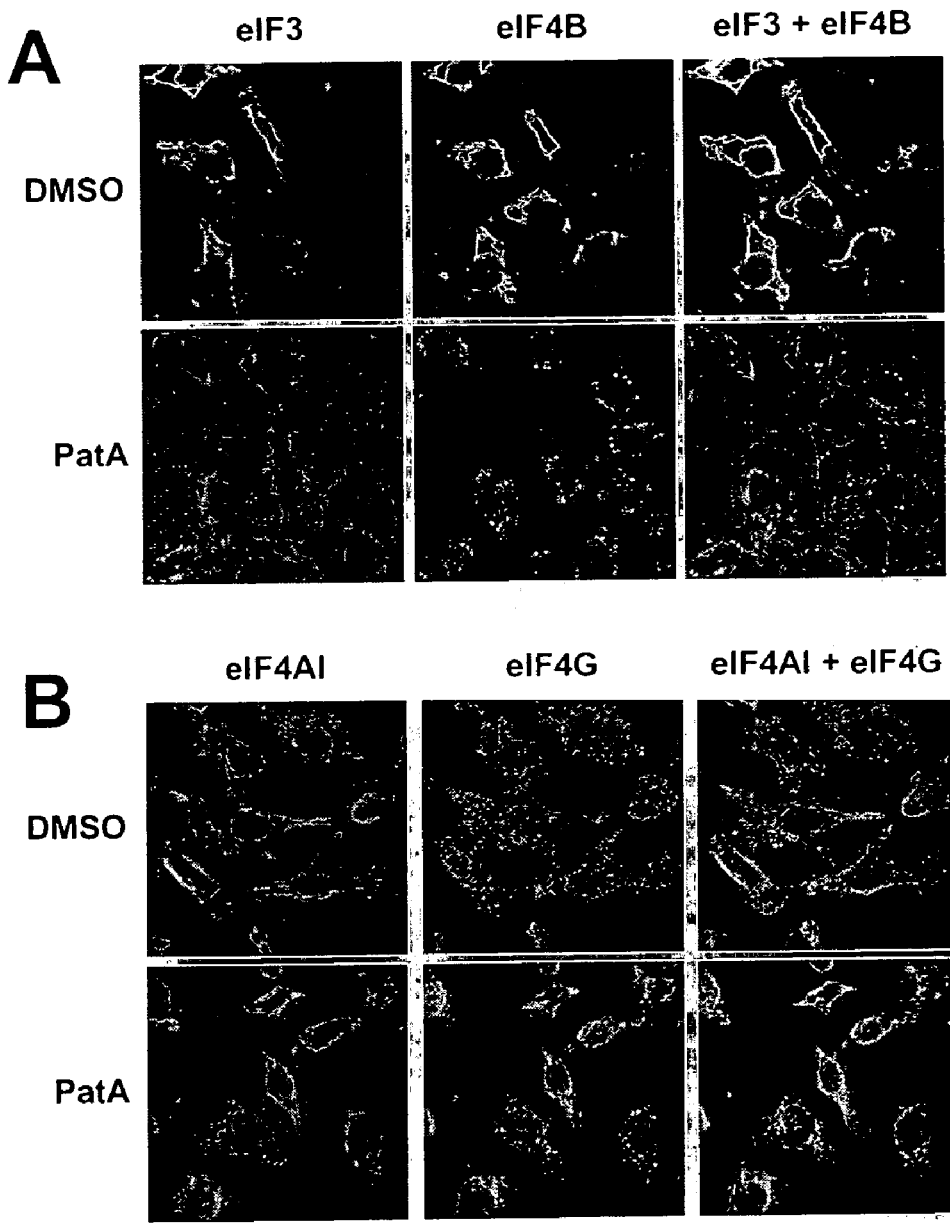
FIGS. 18A-B depict subcellular localization of pateamine A targets after treatment of pateamine A.

PatA and Derivatives Induce the Formation of Stress Granules in vivo. The redistribution of the eIF4 family into the apparent 80S peak in sucrose gradient fractions prompted an investigation of subcellular localization of different eIF4 initiation factors in vivo using indirect immunofluorescence (FIG. 11). Upon treatment with PatA, a population of eIF4A converged into the perinuclear region (FIG. 11A). In comparison with eIF4A, eIF4B underwent a more dramatic change in its subcellular distribution (FIG. 11A, B). In the absence of PatA, eIF4B was dispersed throughout the cytoplasm. Upon PatA treatment, eIF4B redistributed into a small number of cytosolic foci, akin to stress granules-aggregates of protein and RNA formed under heat shock or other stress conditions. One hallmark of stress granules is a relocalization of RNA binding protein T cell internal antigen (TIA)-1 from the nucleus into the cytosolic stress granules. Co-localization of eIF4B with TIA-1 upon treatment with PatA (FIG. 11B) confirmed that cytosolic foci were stress granules. Treatment of cells with arsenite, which is known to induce stress granule formation, also demonstrated eIF4B co-localized with TIA-1 in stress granules (FIG. 11B). CHX did not induce stress granule formation (FIG. 7B). Like eIF4A, a portion of eIF3 also colocalized with eIF4B in stress granules under PatA treatment (FIG. 18A), and eIF4G distribution appeared similar to eIF4A upon PatA treatment (FIG. 18B). As such, PatA is capable of inducing stress granule formation in vivo, likely due to its inhibition of translation initiation. Stress granules are further described in publication "Eukaryotic Initiation Factor 2α Independent Pathway of Stress Granule Induction by the Natural Product Patemine A" by Dang et al. published on Sep. 2, 2006 in Journal of Biological Chemistry, which is incorporated herein by reference to the extent not inconsistent with the description and claimed aspects herein.

A primary binding target for PatA and active derivatives, such as DMDA PatA and tagged versions of such derivatives is the ATP-dependent RNA helicase eIF4A. Given the significant sequence similarity and functional redundancy of eIF4AI and eIF4AII, both eIF4AI and II are likely targeted by PatA. PatA and active derivatives, such as DMDA PatA and tagged versions of such derivatives, stimulat RNA-dependent ATPase and ATP-dependent helicase activities of eIF4AI. In addition, such compositions weaken the interaction between eIF4A and eIF4G, thus affecting the integrity of the eIF4F complex, while simultaneously enhancing the interaction between eIF4A and eIF4B. The cause of the inhibition of translation initiation by such compositions is possibly not directly related to effects on the intrinsic enzymatic activities of eIF4A, but rather by perturbation of protein complexes required for initiation. These changes in the protein complexes are mediated through eIF4A, and are transmitted to the other initiation factors that interacts with eIF4G and eIF4B, thus also perturbing the function of the eIF4F complex.

Activity of eIF4A requires a series of ligand-induced conformational changes and the fact that PatA increases the affinity for ATP and RNA suggests that PatA and compositions described herein may stabilize a specific conformation. This may preclude eIF4A from adopting another required conformation, which may affect its binding affinities for eIF4B/G, leading to changes in eIF4A-containing protein complexes. Like PatA, eIF4B has also been shown to stimulate the ATP-dependent RNA helicase activity of eIF4A either alone or within the eIF4F complex. The inferred interaction is likely transient in nature. The presence of PatA may be stabilizing this transient interaction thereby causing adverse effects on initiation.

Molecular of inhibition of translation initiation by PatA includes disruption of the integrity of eIF4F, inhibition of eIF4B function through the formation of the complex containing both eIF4A and eIF4B, or gain of function of the newly formed eIF4A-PatA-eIF4B complex. A simplest model is where PatA manifests its inhibitory effect through perturbation of the eIF4F complex, as it is well established that eIF4F plays a key role in translation initiation. Additionally eIF4B may be involved. Phosphorylation of eIF4B is known to be required for activity in vivo, and over-expression of eIF4B caused inhibition of translation in cell culture. Given that exposure to PatA led to the enhancement of RNA binding by eIF4B (FIG. 16), it is possible that the complex containing eIF4A, PatA and eIF4B may bind to mRNA with much higher affinity than free eIF4B, leading to a blockage of 43S movement along the 5'-UTR of mRNA that results in the accumulation of the 48S complexes observed in sucrose gradient analysis.

A simplistic model of eukaryotic translation initiation may now include 43S binding to a cap structure, scanning of the 5'-UTR, AUG recognition and stable binding of the 43S, and initiation factor release and 60S subunit joining (data now shown). From ribosome assembly studies described herein (FIG. 9), PatA predominantly causes an accumulation of 48S complexes stalled on mRNA, similar to GMPPNP which is known to block 60S subunit joining, indicating that inhibition occurs prior to this step. Furthermore, accumulation of 48S particles and the identical profiles of co-treatments of PatA and GMPPNP suggest that binding of the 43S to RNA is not affected by PatA. Unlike GMPPNP, however, toeprinting analysis of PatA and GMPPNP co-treatments indicated that the 43S formed in the presence of PatA is not identical to those in the presence of GMPPNP alone (FIG. 9E). Thus, PatA appears to adversely affect either scanning of the 5'-UTR or AUG start codon recognition and stable 43S binding.

Upon stalling of ribosome on mRNA in a cellular context, a signaling cascade is likely to be initiated that eventually leads to stress granule formation. Cell signalling effects would likely amplify the cytotoxic effects of PatA. This may account, in part, for the much lower concentrations of PatA required to inhibit translation and cell proliferation in vivo than in vitro.

Stress granules form under a variety of stress signals; the granules include protein and mRNA aggregates, mediated by the auto-aggregation of TIA-1, that contain several proteins involved in translation initiation, including PABP, eIF3, eIF4E, and eIF4G, as well as several small ribosomal subunits. Stress granules also appear to co-fractionate with free 80S particles when analyzed by sucrose gradient sedimentation. Similar to arsenite, PatA caused a depletion of polysome and a dramatic accumulation of the 80S peak into which both eIF4A and eIF4G were redistributed (FIG. 10). Using indirect immunofluorescence, eIF4B was demonstrated to redistribute into stress granules in response to PatA in vivo (FIG. 11; additional data now shown). Unlike eIF4A and eIF4G, however, only a small fraction of eIF4B redistributed into the 80S peak in the sucrose gradient fractions (FIG. 10). In this respect, eIF4B is more similar to the well-established marker and a key initiator of stress granule formation, TIA-1, that accumulates quantitatively in stress granules, but does not co-fractionate in the 80S region of sucrose gradients. It is interesting that eIF4B, unlike eIF4A and eIF4G, behaves in a manner that is quite similar to TIA-1.

The mechanism of action by PatA as described herein is unprecedented. Its ability to promote formation of a ternary complex between eIF4A and eIF4B is reminiscent of a mode of action by immunosuppressive drugs cyclosporin A, FK506 and rapamycin. Thus, PatA may be a new member of this unique family of natural products that function by bringing two proteins into a complex, thereby blocking the function of both proteins. However, unlike these other compounds, instead of inhibiting the activity of its target (as in the case with cyclosporin A, FK506 and rapamycin), PatA acts on an agonist of eIF4A's activity. Furthermore, binding of PatA to eIF4A has profound secondary effects on its interaction with other eIF4 proteins, making PatA a unique small ligand that has significant effects on multiple protein-protein interactions.

Unlike other known anticancer and antiproliferative drugs, PatA and its analogs as described herein, provide a completely novel mechanism of action through inhibition of eIF4A-dependent translation initiation. They can cause either cell cycle arrest or induce apoptosis in transformed cells. In contrast, toxicity of such compounds to slow growing normal cells is low. Arsenite, which acts in part by inhibiting protein translation and causing stress granule formation, has been used for the treatment of acute promyelocytic leukemia for decades. Unlike arsenite, PatA and its analog compositions described herein specifically target translation initiation factors. PatA and its analogs and derivatives described herein are therefore suitable as anticancer and antiproliferative agents. PatA and its derivatives are also valuable molecular probes for continued evalutaion of eukaryotic translation initiation and as lead compounds for development of novel anticancer agents.

Cell Culture and transient overexpression. HeLa, RKO, and 293T cells were cultured in DMEM (10% FBS), and Hela S3 and MCF-7 cells in RPMI1640 (10% FBS) in a water jacket cell culture incubator with 5% $CO_2$. Transient transfection was performed using kit as described by the manufacturer. Ectopic overexpression of indicated proteins was performed using pSG5-myc-STRAP, pSG5-eIF4AI, and pcDNA-Flag-4B(wt)

Streptavidin-agarose Pulldown with B-PatA. Cell lysates from RKO cells were prepared as previously described (Griffith et al., 1997). HeLa lysates were prepared in buffer: 10 mM HEPES-OH, pH 7.6, 10 mM $KC_2H_3O_2$, and 0.5 mM $MgC_2H_3O_2$. RRL and WGE were diluted about 12 fold using HeLa lysate buffer. All pulldowns included protease inhibitors. Streptavidin-beads were pre-incubated with 10 mg/ml BSA in buffer for 1 h at 4° C. with mixing. Equal aliquots of lysate (200 μl) were incubated with DMSO or PatA analog for 1 h at 4° C. with mixing, followed by addition of DMSO or B-PatA and incubation for 2 h. Each sample was combined with equal amounts of pre-blocked beads and incubated for 1 h at 4° C. Beads were washed with 3 ml of buffer, boiled in SDS-PAGE loading buffer and analyzed by SDS-PAGE and silver-staining or immunoblotting.

6XHis-eIF4AI pulldown, Co-immunoprecipitation, and $m^7$GTP-Sepharose pulldown. For 6XHis-eIF4AI pulldowns, HeLa lysates were prepared as described above. Equal aliquots (200 μl) of lysate were incubated with PatA analogs or DMSO and 8.5 μg of 6XHis-eIF4AI overnight at 4° C., followed by addition of Ni-NTA resin for 1 h, then resin was washed with 3 ml buffer, and boiled in SDS-PAGE loading buffer followed by SDS-PAGE and immunoblotting with indicated antibodies. For co-immunoprecipitation, 293T cells with vector control or pcDNA3-Flag-4B lysates were prepared by pipetting in: 20 mM HEPES, pH 7.4, 100 mM KCl, 0.5% Triton-X-100, 20% glycerol, protease inhibitor and 15 μg/ml RNAse A followed by clearing at 13 000 g (10 min). For DMDA-PatA treated samples, lysis and wash buffers also contained 100 nM DMDA-PatA. Anti-Flag antibody was incubated overnight at 4° C., followed by addition of Protein G beads for 4 h. Beads were washed 3× with 500 μl buffer, boiled in SDS-PAGE loading buffer followed by SDS-PAGE and immunoblotting. $m^7$GTP-Sepharose was performed as described (Yoder-Hill et al., 1993) with modifications. 30 μl RRL was incubated with DMSO or DMDA-PatA at room temperature for 30 min, diluted with buffer supplemented with DMSO or DMDA-PatA (20 nM), then combined with 50 μl beads for 3 h at 4° C. followed by 4 washes with 1 ml buffer. Captured proteins were visualized by SDS-PAGE and immunoblotting following boiling of beads in SDS-PAGE loading buffer.

Cell Proliferation Assay. $1 \times 10^5$ of indicated cells in each well of a 96-well plate were treated with indicated compounds for 24 h followed by addition of 0.11 μCi of [$^3$H]-thymidine (6.7 Ci/mmol) per well for 6 h, followed by harvesting to GF/C filtermats using a cell harvester. Filtermats were air-dried and scintillation counted. $IC_{50}$s were determined from quadruplicate data readings and curve-fitting analysis.

Metabolic Labelling. About 5000 HeLa S3 cells per well in 96-well plates were cultured overnight in duplicate. One set of plates were washed twice with, then incubated for 20 min in Met and Cys free medium, then exchanged for labeling medium (RPMI 1640 with 10% FBS dialyzed in PBS overnight, and 0.15 mCi/ml [$^{35}$S]-Met and [$^{35}$S]-Cys) with indicated compounds and final volume of 100 μl per well. After 1 h or 3 h incubation, and two washes with ice-cold PBS, cells were lysed in RIPA buffer, under agitation for 30 min at 4° C. 5 μl of lysate from each well was combined with 25 μl of 1 mg/ml BSA, and added to 96 well plates, followed by addition of 150 μl of 5% TCA in ethanol and incubated at 4° C. for 30 min. Filtration was performed on a vacuum manifold as per manufacturer's instructions with 2 washes of 5% TCA in ethanol, then twice with 100% ethanol. After air-drying, scintillation counting was performed. For the second set, replacement media contained 10 mCi/ml [$^3$H]-uridine and indicated compound, and incubated for 1 or 3 h. Remaining procedure was identical to cell proliferation assay.

In vitro Translation and Transcription. pSP/(CAG)$_{33}$/FF/HCV/Ren●pA$_{51}$ and pKS/FF/EMC/Ren were linearized by BamHI, then purified by phenol:chloroform extraction and ethanol precipitation, and dissolved in water. pSP/(CAG)$_{33}$/FF/HCV/Ren●pA$_{51}$ and pKS/FF/EMC/Ren were individually transcribed using a large scale RNA production system in the presence of m7Gppp cap analog followed by incubation with DNase as described by the manufacturer. Resulting RNA was purified using a kit as described by the manufacturer. Translation was performed using a rabbit reticulocyte lysate system as per instructions. Briefly, 200 ng of purified RNA was combined in a 20 μl reaction containing 10 μl RRL, 0.2 μl each of minus Met and minus Leu amino acid mixtures, 70 mM KCl, 2 mM DTT, 1× translation buffer, and 10 units of RNasin. Compounds or DMSO were added to a final DMSO concentration of 2%. Reactions were incubated at 30° C. for 1.5 h, then 5 μl of the reaction mixture was assayed for luciferase activity as per instructions of luciferase reporter assay system.

Recombinant proteins. The entire ORF of human eIF4AI was ligated in-frame into the BamHI and HindIII sites of the pET-28a expression vector after PCR amplification from HeLa cells. Protein was produced in BL21(DE3) *E. coli* cultured in LB medium by induction with 1 mM IPTG for 6 h at 37° C. Cells were lysed by sonication and protein was purified using Ni-NTA resin as described by the manufacturer. For pET(His$_6$-eIF4B), induction conditions were for 72 h at 16° C. Purification included a 1 ml Heparin column with a linear KCl gradient (50-500 mM).

Sucrose Gradient Density Centrifugation and Toeprinting. Vector pβ-Hb was digested with HindIII, purified and transcribed as described above with the inclusion 30 μCi [γ-$^{32}$P]-GTP (800 Ci/mmol). Radiolabeled EMCV IRES, and HCV IRES RNA were prepared by PCR amplification of pRΔDE●EMCVF and pRΔDE●HCVF using a suitable forward primer with a T3 promoter and reverse primer. PCR products were purified with a PCR purification kit. Transcription was performed using 160 U of a T3 RNA polymerase in a 20 μl volume with 1 mM each of ATP, CTP, UTP, 0.5 mM GTP, 30 μCi of [γ-$^{32}$P]-GTP, with or without 2 mM m$^7$Gppp cap analog, and one μg of PCR product. Prior to analysis, all radiolabeled RNAs were purified using a suitable kit. 200 ng RNA was combined with 25 μl of RRL, 0.4 μl each of minus Met and minus Leu amino acid mixtures, 10 U RNasin, 70 mM KCl, 2 mM DTT in a total volume of 40 μl. Where indicated, mixtures also contained 1.25 mM GMPPNP, 0.75 mM CHX, and/or DMSO (1%) or 100 μM PatA. Mixtures were incubated at 30° C. for 15 min, then diluted with 160 μl of gradient buffer (20 mM HEPES pH 7.4, 150 mM KC$_2$H$_3$O$_2$, 5 mM MgCl$_2$) and overlaid onto 15-35% (w/v) linear sucrose gradient in a 5 ml volume followed by ultracentrifugation at 50 000 rpm in a suitable rotor for 1 h at 4° C. Fractions (200 μl) were manually collected from the top of the gradient and assayed by scintillation counting.

Toeprinting was performed as described (Anthony and Merrick, 1992) using a capped β-globin RNA. Annealed oligo:template was processed under conditions described for sucrose gradient ultracentrifugation. 10% of fractions were analyzed by scintillation counting. Fractions 2 and 8 from both DMSO or PatA were extracted using phenol:chloroform, followed by reverse transcription using AMV-RT. Sequencing ladder was produced by standard dideoxy-sequencing protocol using AMV-RT, and radio-labeled primer annealed to template RNA.

UV-crosslinking. [α-$^{32}$P]-CTP (3000 Ci/mmol) labeled β-globin RNA was incubated 15 min with RRL under DMSO or PatA (40 μM) with 0.75 mM CHX at 30° C. Protein-RNA complexes were fixed with UV light on ice using a UV linker machine for 5 min then treated with 7.5 μg RNase for 15 min at 37° C. Samples were analyzed by SDS-PAGE and autoradiography.

Immunocytochemistry. Immunocytochemistry and immunofluorescence were performed as described herein. Briefly, HeLa cells were plated in chamber slides and allowed to recover overnight, then treated with either DMSO or 10 nM PatA for 3 h followed by fixing with 4% p-formaldehyde. Following washing, permeabilization, and blocking, cells were incubated with indicated primary antibodies. Mounting was performed using a mounting medium. Immunofluorescence was visualized using a confocal microscope.

ATPase and Helicase. ATPase activity was performed as described (Korneeva et al., 2005) with minor modifications. Reactions contained 2.5% DMSO, 6XHis-eIF4AI concentration was 0.56 μM, and reaction time was 10 min at 37° C. in buffer: 20 mM Tris-HCl, pH 7.5, 0.5 mM MgCl$_2$, 100 mM KCl, 2 mM DTT, 0.1% (v/v) Tween 20, 10% (v/v) glycerol, 1 mg/ml BSA, and reactions were supplemented with 3-5 μCi of [γ-$^{32}$P]-ATP (6000 Ci/mmol). Saturating poly(U) concentrations were 1239 μM (nucleotides/20). Released phosphate was visualized on 15% native TBE polyacrylamide gels followed by autoradiography of wet gels (30 min exposure). Film was aligned with gels and spots were excised and $^{32}$P levels were quantified by scintillation counting. K$_m$ and V$_{max}$ were determined by curve fitting. Helicase assays were performed as described (Rogers et al., 2001a) with minor modifications. RNA substrates were R-11 and R-44; duplex concentration was 5 nM, and reactions contained buffer: 20 mM HEPES, pH 7.5, 70 mM KCl, 2 mM DTT, 1 mg/ml BSA, 1 mM MgC$_2$H$_3$O$_2$, 40-80 U RnaseOUT, and 1 mM ATP. Reactions were incubated at 37° C. for 15 min, followed by quenching and visualization of products by native PAGE (15%) and autoradiography, followed by excision bands from dried gels and scintillation counting.

Cellular polyribosome profiles. 293T cells were treated as indicated for 30 min. Cells were washed twice with ice-cold PBS and pipetted for 5 min in 500 μl of chilled TMK100 buffer (20 mM Tris-HCl pH 7.4, 5 mM MgCl$_2$ 100 mM KCl, 2 mM DTT, 1% Triton X-100 and 100 U/ml RNAsin in DEPC water). After clearing at 10,000×g (10 min) at 4° C., the supernatant (S10) was layered onto 11 ml, 15-45% linear sucrose gradient containing 20 mM HEPES pH 7.4, 100 mM KCl, 5 mM MgCl$_2$ and 2 mM DTT. Ultracentrifugation at 40,000 rpm for 1.5 h at 4° C. was performed in a suitable rotor. Fractions were collected from the top of the gradient by injection of Flurinert FC-40 from bottom of centrifuge tube. Gradient profiles were monitored at 254 nm. For immunoblotting, 7 mg of total protein were processed as described above, followed by collection of 500 μl fractions were collected from the top. 100 μl aliquots of each were boiled in SDS sample buffer, followed by SDS-PAGE and immunoblotting.

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

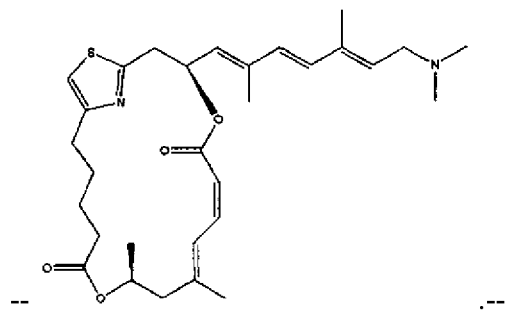

We claim the following:

1. A method of synthesizing a compound of formula (A):

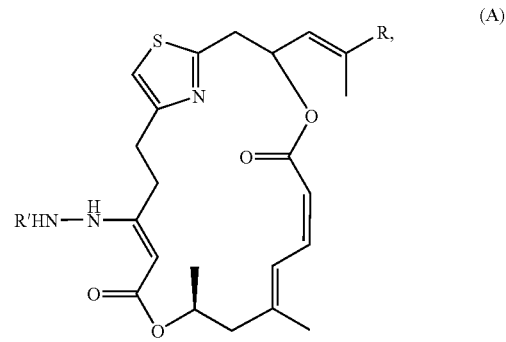

wherein R is Br and R' is —SO$_2$C$_6$H$_4$CH$_2$(CH$_2$)$_n$C≡CSi(CH$_3$)$_3$ wherein n=1-5, comprising reacting a compound of formula (B):

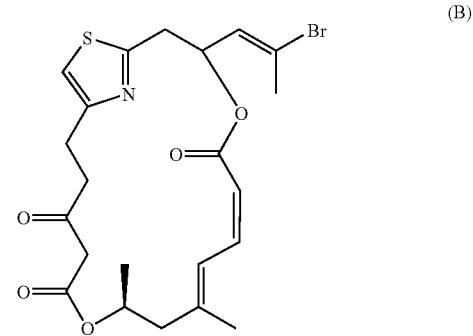

in the presence of NH$_2$NHSO$_2$C$_6$H$_4$CH$_2$(CH$_2$)$_n$C≡CSi(CH$_3$)$_3$, wherein n=1-5, and catalytic Al$_2$O$_3$.

2. A pharmaceutical composition comprising a pateamine A analog of formula (I):

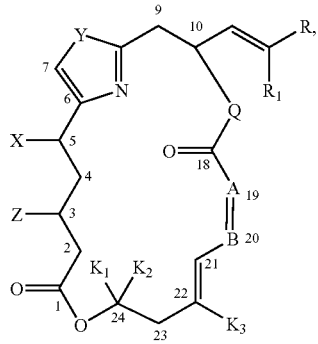

(I)

and its pharmaceutically acceptable salts, wherein:
A-B is ethane, (F) and (Z)-ethene, (F) and (Z)-substituted ethene, or ethyne;
$K_1$, $K_2$ and $K_3$ are hydrogen or alkyl$_{(C=1-3)}$;
Q is NH or O;
X is hydrogen;
Y is S, NH, or O;
Z is hydrogen;
$R_1$ is hydrogen or alkyl$_{(C=1-3)}$; and
R is selected from the following:
(a) an alkene of the formula:

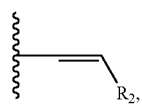

wherein $R_2$ is selected from the group consisting of alkyl, alkylhydroxy, alkylalkoxy, alkylamino, alkylaminoalkyl and alkylaminodialkyl;
(b) an alkenylaryl of the formula:

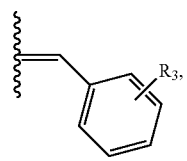

wherein $R_3$ is selected from the group consisting of hydrogen, alkyl, alkenyl, alkynyl, hydroxy, alkoxy, amino, alkylamino, dialkylamino, trifluoromethane and fluoro;
(c) methyldienylpentyl of the formula:

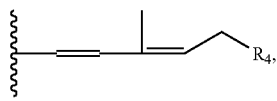

wherein $R_4$ is selected from the group consisting of hydrogen, alkyl, alkenyl, alkynyl, hydroxy, alkoxy, amino, alkylamino and dialkylamino; and (d) methylalkenylpentyl of the formula:

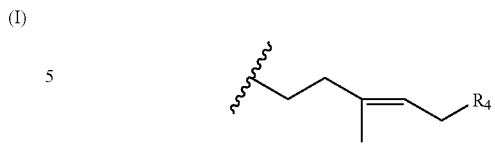

wherein $R_4$ is selected from the group consisting of hydrogen, alkyl, alkenyl, alkynyl, hydroxy, alkoxy, amino, alkylamino and dialkylamino,
and a pharmaceutically acceptable carrier.

3. The pharmaceutical composition of claim 2, wherein the pateamine A analog of formula (I) is further defined as a compound of formula (II), or its pharmaceutically acceptable salts:

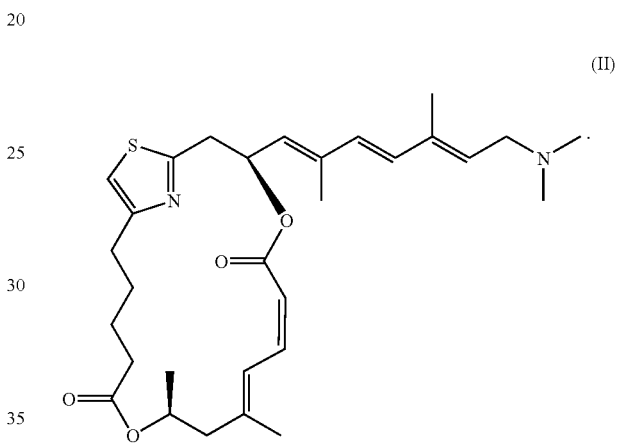

(II)

4. The method of claim 1, further comprising reacting the compound of formula (A) with $Bu_3SnCH=CHC(CH_3)=CHCH_2N(CH_3)_2$, $Pd_2dba_3$ and $AsPh_3$ to form a compound of formula (C):

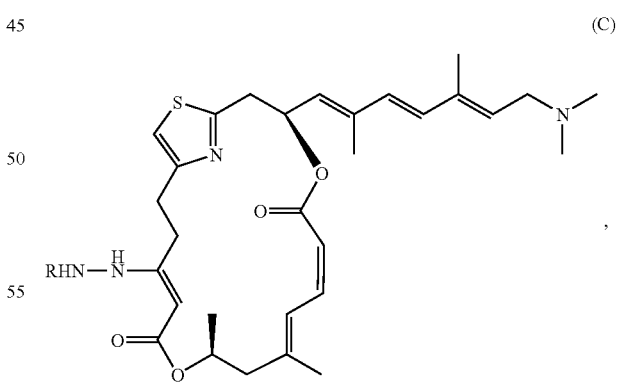

(C)

wherein R is $-SO_2C_6H_4CH_2(CH_2)_nC\equiv CSi(CH_3)_3$ and n=1-5.

5. The method of claim 4, further comprising reacting the compound of formula (C) with a biotinylated azide of formula (B), 5 mol % of CuI, and N,N-diisopropylethylamine to form the compound of formula (D):

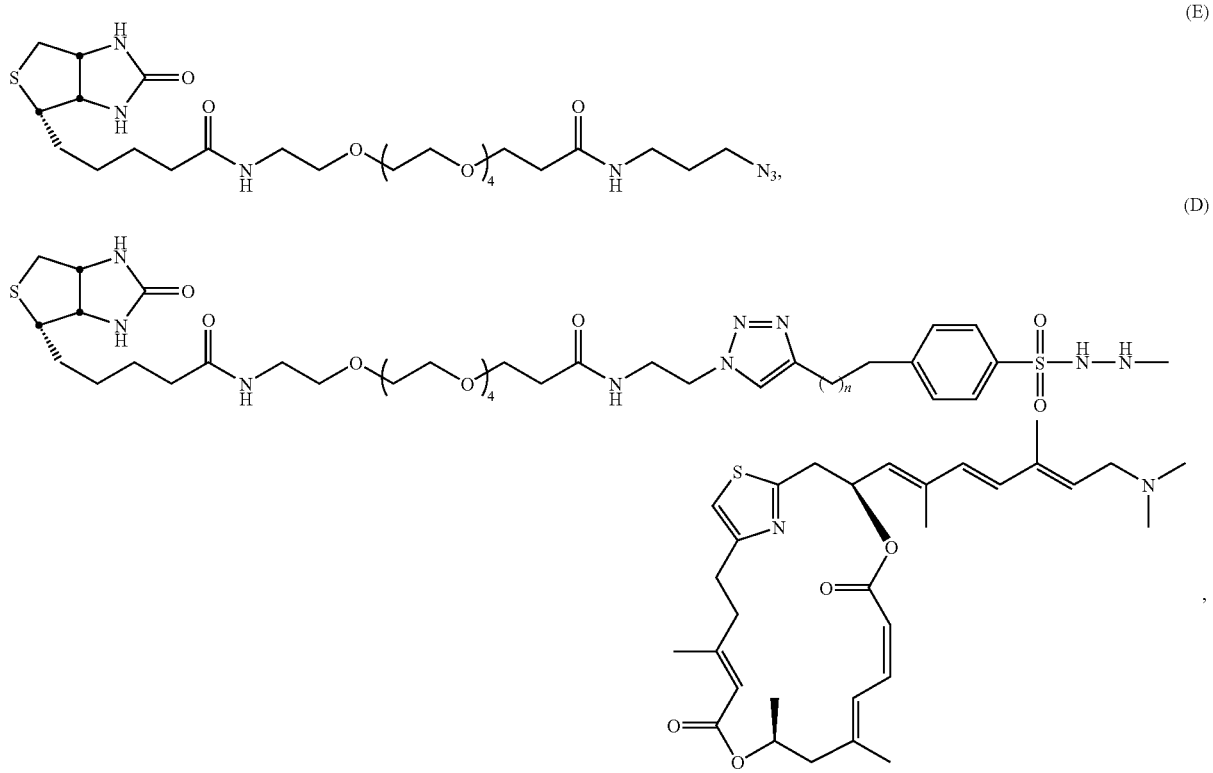

wherein n=1-5.

6. The pharmaceutical composition of claim 2, wherein A-B is ethane.

7. The pharmaceutical composition of claim 2, wherein A-B is (E) and (Z)-ethene.

8. The pharmaceutical composition of claim 2, wherein A-B is (E) and (Z)-substituted ethene.

9. The pharmaceutical composition of claim 2, wherein A-B is ethyne.

10. The pharmaceutical composition of claim 2, wherein $K_1$, $K_2$ and $K_3$ are hydrogen.

11. The pharmaceutical composition of claim 2, wherein $K_1$, $K_2$ and $K_3$ are alkyl$_{(C=1-3)}$.

12. The pharmaceutical composition of claim 2, wherein Q is NH.

13. The pharmaceutical composition of claim 2, wherein Q is O.

14. The pharmaceutical composition of claim 2, wherein $R_1$ is hydrogen.

15. The pharmaceutical composition of claim 2, wherein $R_1$ is alkyl$_{(C=1-3)}$.

16. The pharmaceutical composition of claim 2, wherein R is alkyl, alkylhydroxy or alkylalkoxy.

17. The pharmaceutical composition of claim 2, wherein R is alkylamino, alkylaminoalkyl or alkylaminodialkyl.

18. The pharmaceutical composition of claim 2, wherein $R_3$ is alkyl, alkenyl or alkynyl.

19. The pharmaceutical composition of claim 2, wherein $R_3$ is hydroxy or alkoxy.

20. The pharmaceutical composition of claim 2, wherein $R_3$ is amino, alkylamino or dialkylamino.

21. The pharmaceutical composition of claim 2, wherein $R_3$ is trifluoromethane or fluoro.

22. The pharmaceutical composition of claim 2, wherein R is a methyldienylpentyl of the formula:

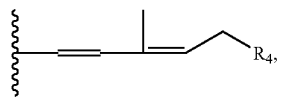

wherein $R_4$ is selected from the group consisting of hydrogen, alkyl, alkenyl and alkynyl.

23. The pharmaceutical composition of claim 2, wherein R is a methyldienylpentyl of the formula:

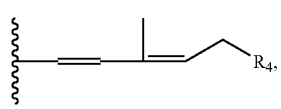

wherein $R_4$ is from the group consisting of hydroxy, alkoxy, amino, alkylamino and dialkylamino.

24. The pharmaceutical composition of claim 2, wherein R is a methylalkenylpentyl of the formula:

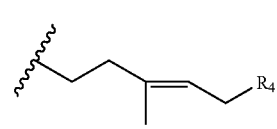

wherein R$_4$ is selected from the group consisting of hydrogen, alkyl, alkenyl, alkynyl, hydroxy, alkoxy, amino, alkylamino and dialkylamino.

25. The pharmaceutical composition of claim 2, wherein R is a methylalkenylpentyl of the formula:

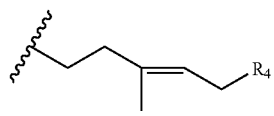

wherein R$_4$ is selected from the group consisting of hydroxy and alkoxy.

26. The pharmaceutical composition of claim 2, wherein R is a methylalkenylpentyl of the formula:

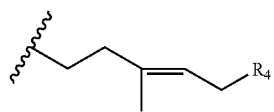

wherein R$_4$ is selected from the group consisting of amino, alkylamino and dialkylamino.

27. A method of treating leukemia in a subject in need of treatment, comprising administering to the subject a compound having the formula:

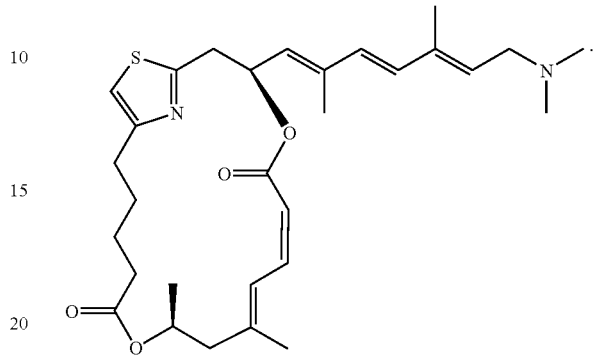

\* \* \* \* \*

UNITED STATES PATENT AND TRADEMARK OFFICE
CERTIFICATE OF CORRECTION

PATENT NO. : 7,737,134 B2  
APPLICATION NO. : 11/544474  
DATED : June 15, 2010  
INVENTOR(S) : Romo et al.

Page 1 of 8

It is certified that error appears in the above-identified patent and that said Letters Patent is hereby corrected as shown below:

| COLUMN | LINE |
|---|---|
| 48 | 30 |

Claim 1,

Formula (A)

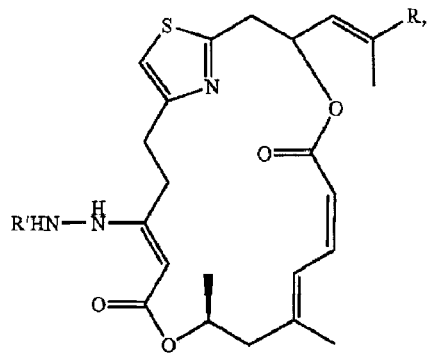

" (A)  
should read

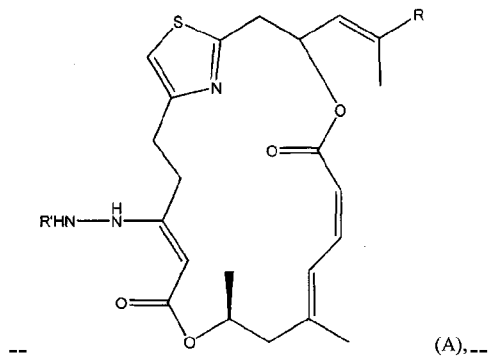

-- 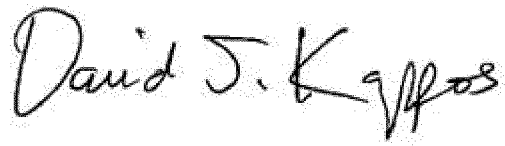 (A),--

Signed and Sealed this  
First Day of May, 2012

David J. Kappos  
*Director of the United States Patent and Trademark Office*

CERTIFICATE OF CORRECTION (continued)
U.S. Pat. No. 7,737,134 B2

| COLUMN | LINE | |
|---|---|---|
| 49<br>Claim 2, | 1 | |

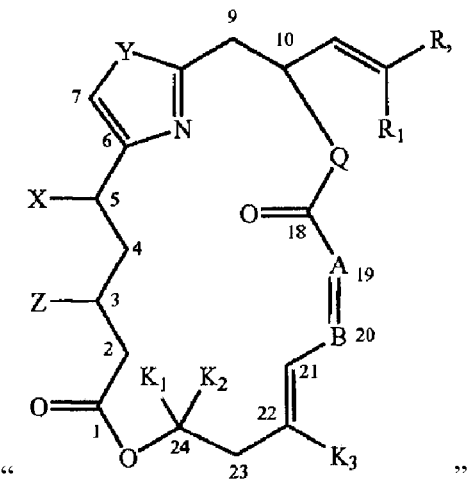

Formula (I) " "

should read

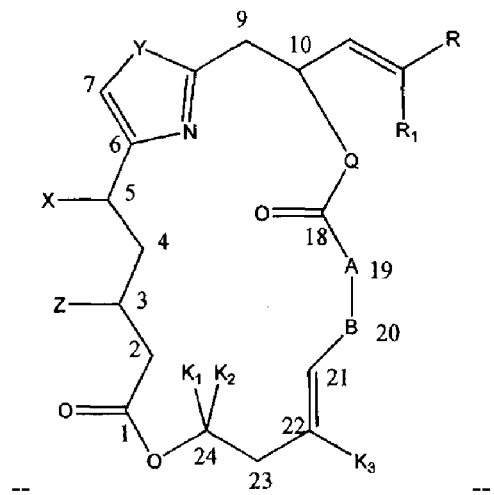

--  --

| 49<br>Claim 2, | 19 | "(F)", first instance, should read --(E)-- |
| 49<br>Claim 2, | 19 | "(F)", second instance, should read --(E)-- |

CERTIFICATE OF CORRECTION (continued)
U.S. Pat. No. 7,737,134 B2

| COLUMN | LINE | |
|---|---|---|
| 49 Claim 2, | 35 | (formula) " 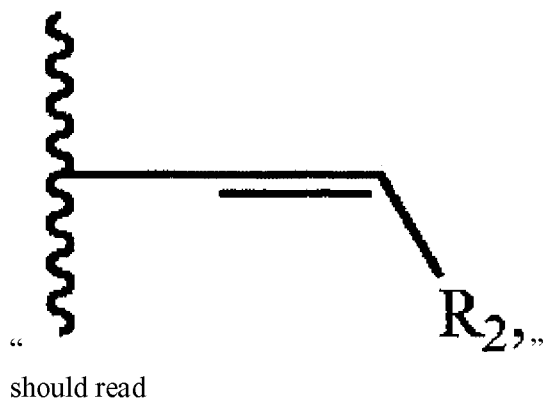 should read 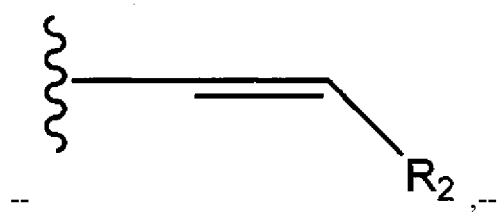 |
| 49 Claim 2, | 39-40 | the term "alky-laminoalkyl", should break as follows --alkyl-aminoalkyl- -- |
| 49 Claim 2, | 42 | (formula) " 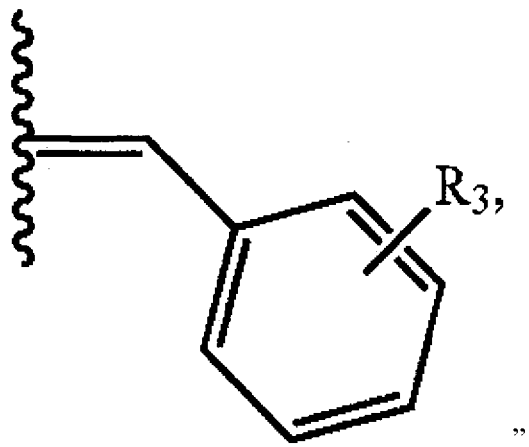 " |

| COLUMN | LINE |
|---|---|
| | should read |
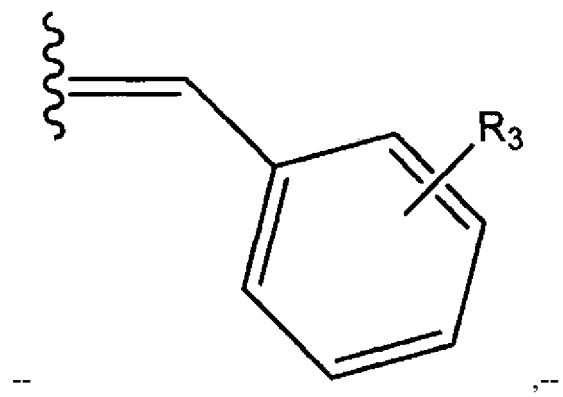
| 49 | 60 |
| Claim 2, | |
| (formula) | " |
should read
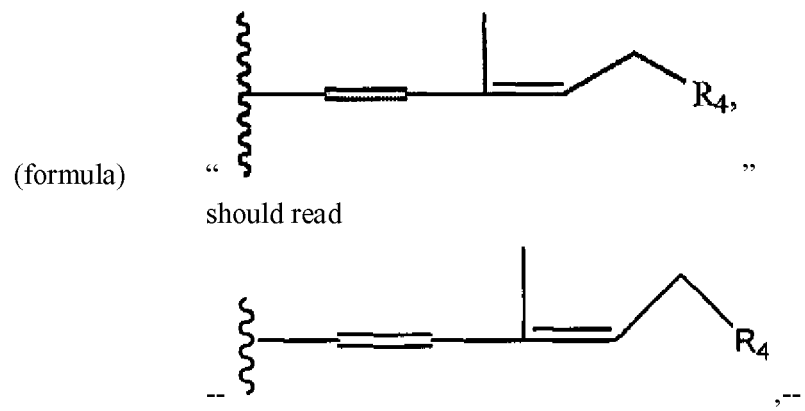
| 50 | 22-23 |
| Claim 3, | |
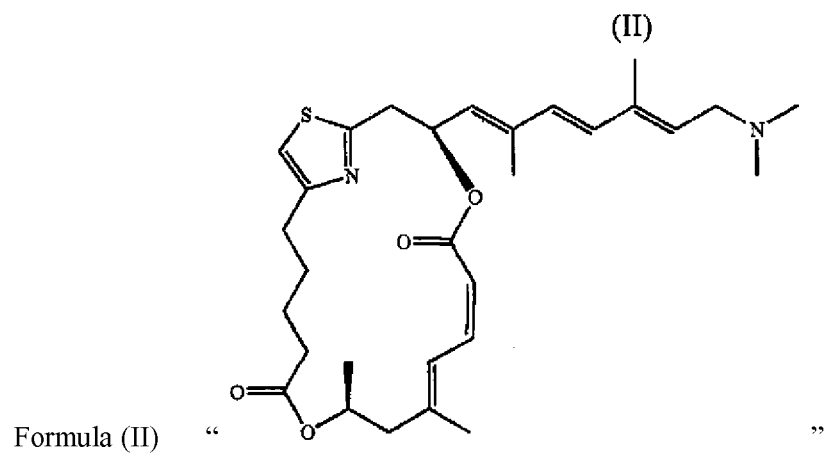
Formula (II) " "

CERTIFICATE OF CORRECTION (continued)
U.S. Pat. No. 7,737,134 B2

COLUMN    LINE should read

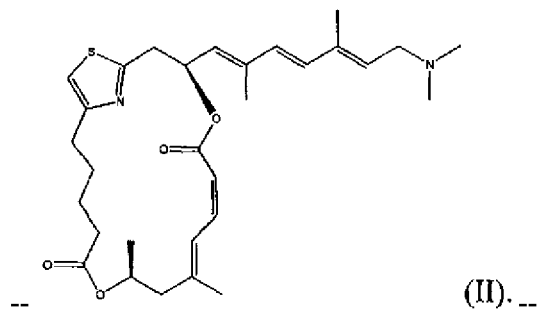

(II).

50        45-46                                          (C)
Claim 4,

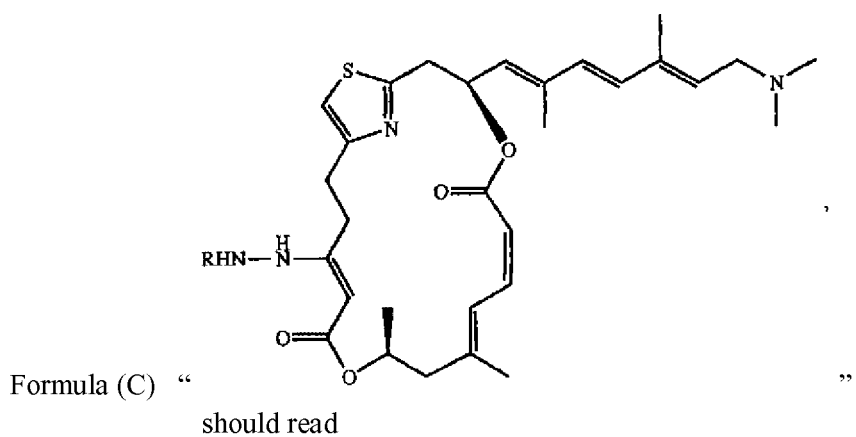

Formula (C) " " should read

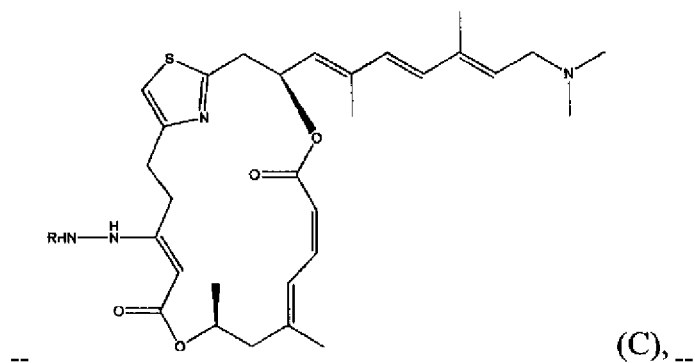

(C), 50        65       "(B), 5 mol%" should read --(E), 5 mol%--
Claim 5,

CERTIFICATE OF CORRECTION (continued)
U.S. Pat. No. 7,737,134 B2

Page 6 of 8

| COLUMN | LINE | |
|---|---|---|
| 51-52 Claim 5, | 1-2 | |

Formula (E) "  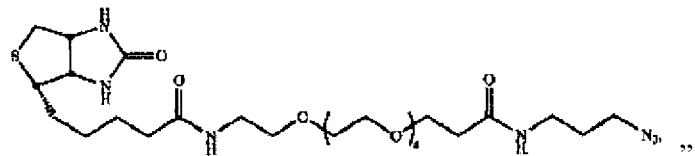

should read

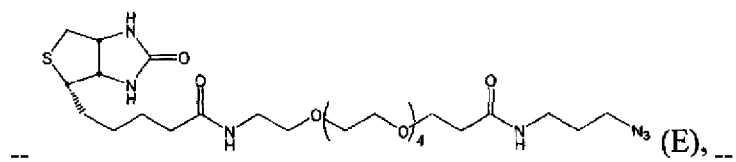

| 51-52 Claim 5, | 3 | in the first part of formula (D), delete "(D)" |

Formula (D)

| 51-52 Claim 5, | 5 | in the second part of formula (D) |

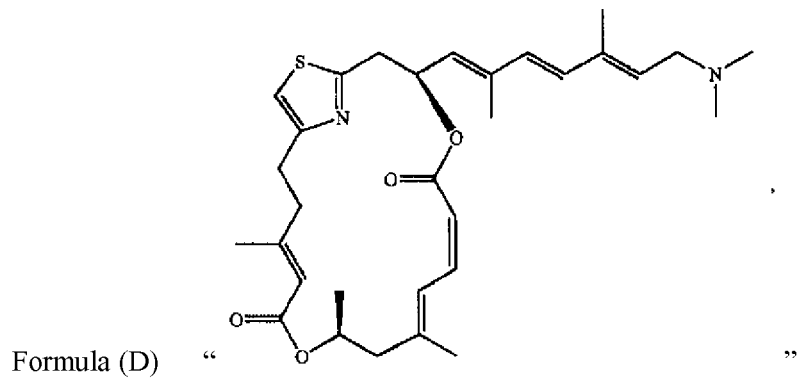

Formula (D)   "                                                                 "

CERTIFICATE OF CORRECTION (continued)
U.S. Pat. No. 7,737,134 B2 should read

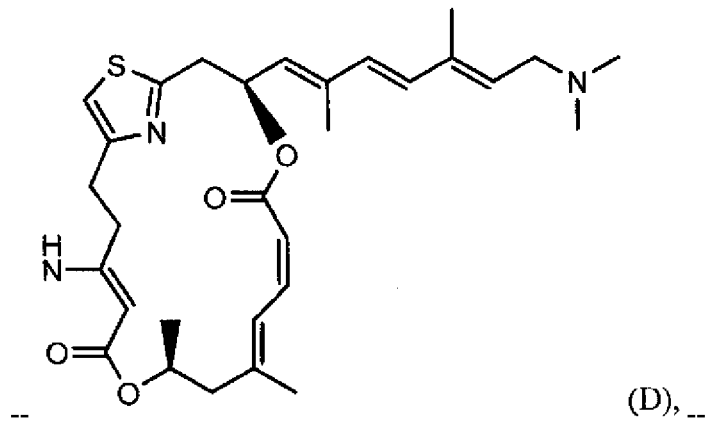

(D), --

| COLUMN | LINE |
|---|---|
| 52 Claim 22, | 40 |

(formula) " 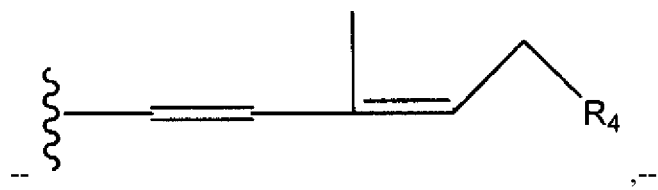 "

should read

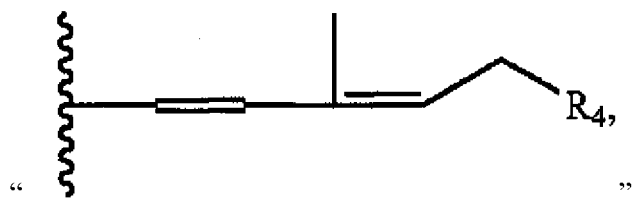
, --

| 52 Claim 23, | 50 |

(formula) "

CERTIFICATE OF CORRECTION (continued)
U.S. Pat. No. 7,737,134 B2

Page 8 of 8

| COLUMN | LINE | |
|---|---|---|
| | | should read |

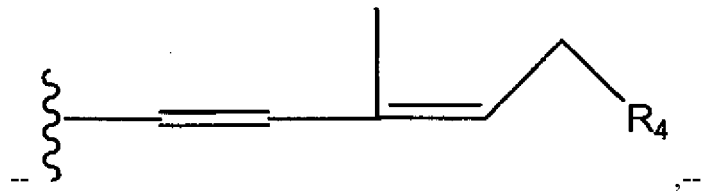

| 52 Claim 23, | 56 | "R4 is from" should read --R4 is selected from-- |

| 54 Claim 27, | 10 | |

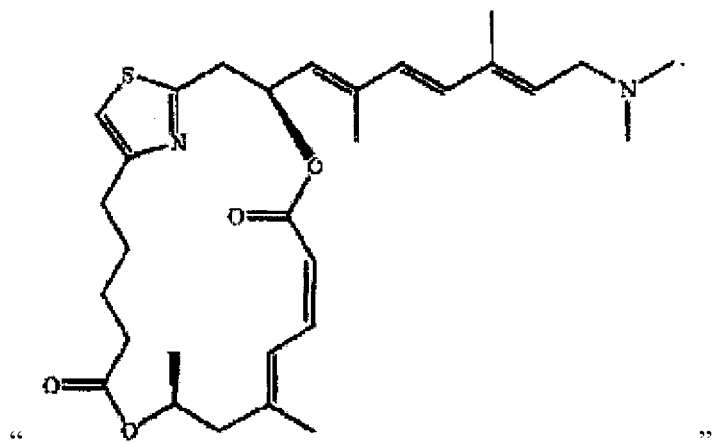

should read